US010837883B2

(12) United States Patent
Kleinschmidt et al.

(10) Patent No.: US 10,837,883 B2
(45) Date of Patent: Nov. 17, 2020

(54) MICROFLUIDIC SYSTEMS AND METHODS FOR REDUCING THE EXCHANGE OF MOLECULES BETWEEN DROPLETS

(75) Inventors: Felix Kleinschmidt, Freiburg (DE); Andrew David Griffiths, Strasbourg (FR); François Caron, Selestat (FR); Abdeslam El Harrak, Bischheim (FR); Eric Brouzes, New York, NY (US); Darren Link, Lexington, MA (US)

(73) Assignees: Bio-Rad Laboratories, Inc., Hercules, CA (US); University of Strasbourg, Strasbourg (FR)

( * ) Notice: Subject to any disclaimer, the term of this patent is extended or adjusted under 35 U.S.C. 154(b) by 1479 days.

(21) Appl. No.: 13/518,619

(22) PCT Filed: Dec. 22, 2010

(86) PCT No.: PCT/US2010/061741
§ 371 (c)(1),
(2), (4) Date: Nov. 29, 2012

(87) PCT Pub. No.: WO2011/079176
PCT Pub. Date: Jun. 30, 2011

(65) Prior Publication Data
US 2013/0109575 A1    May 2, 2013

Related U.S. Application Data

(60) Provisional application No. 61/289,654, filed on Dec. 23, 2009.

(51) Int. Cl.
| *G01N 1/38* | (2006.01) |
| *G01N 33/53* | (2006.01) |
| *B01L 3/00* | (2006.01) |
| *B01L 7/00* | (2006.01) |
| *C12M 1/12* | (2006.01) |

(52) U.S. Cl.
CPC ........... *G01N 1/38* (2013.01); *G01N 33/5302* (2013.01); *B01L 3/502761* (2013.01); *B01L 3/502784* (2013.01); *B01L 7/52* (2013.01); *B01L 2200/0652* (2013.01); *B01L 2200/0673* (2013.01); *B01L 2300/0816* (2013.01); *B01L 2300/0864* (2013.01); *B01L 2300/0867* (2013.01); *B01L 2400/0424* (2013.01); *B01L 2400/0469* (2013.01); *B01L 2400/086* (2013.01); *C12M 25/01* (2013.01)

(58) Field of Classification Search
None
See application file for complete search history.

(56) References Cited

U.S. PATENT DOCUMENTS

| 2,097,692 | A | 11/1937 | Fiegel |
| 2,164,172 | A | 6/1939 | Dalton |
| 2,656,508 | A | 10/1953 | Coulter |
| 2,692,800 | A | 10/1954 | Nichols et al. |
| 2,797,149 | A | 6/1957 | Skeggs |
| 2,879,141 | A | 3/1959 | Skeggs |
| 2,971,700 | A | 2/1961 | Peeps |
| 3,479,141 | A | 11/1969 | Smythe et al. |
| 3,608,821 | A | 9/1971 | Simm et al. |
| 3,698,635 | A | 10/1972 | Sickles |
| 3,816,331 | A | 6/1974 | Brown, Jr. et al. |
| 3,930,061 | A | 12/1975 | Scharfenberger |
| 3,960,187 | A | 6/1976 | Stock et al. |
| 3,980,541 | A | 9/1976 | Aine |
| 3,982,541 | A | 9/1976 | L'Esperance, Jr. |
| 4,014,469 | A | 3/1977 | Sato |
| 4,022,575 | A | 5/1977 | Hansen et al. |
| 4,034,966 | A | 7/1977 | Suh et al. |
| 4,059,552 | A | 11/1977 | Zweigle et al. |
| 4,091,042 | A | 5/1978 | Alexanderson et al. |
| 4,117,550 | A | 9/1978 | Folland et al. |
| 4,130,394 | A | 12/1978 | Negersmith |
| 4,210,809 | A | 7/1980 | Pelavin |
| 4,253,846 | A | 3/1981 | Smythe et al. |
| 4,266,721 | A | 5/1981 | Sickles |
| 4,279,345 | A | 7/1981 | Allred |
| 4,297,345 | A | 10/1981 | Howarth |
| 4,315,754 | A | 2/1982 | Ruzicka et al. |
| 4,378,957 | A | 4/1983 | Malkin et al. |
| 4,383,767 | A | 5/1983 | Jido |
| 4,439,980 | A | 4/1984 | Biblarz et al. |
| 4,470,905 | A * | 9/1984 | Pangburn ........... B01D 17/0208 210/136 |
| 4,508,265 | A | 4/1985 | Jido |
| 4,533,634 | A | 8/1985 | Maldonado et al. |

(Continued)

FOREIGN PATENT DOCUMENTS

| AU | 2004225691 B2 | 6/2010 |
| CA | 2520548 A1 | 10/2004 |

(Continued)

OTHER PUBLICATIONS

Kim et al. (Lab Chip, 2009, vol. 9, pp. 1294-1297).*
Mazutis et al. (Lab on a Chip 9.18 (2009): 2665-2672).*
Frenz et al. (Langmuir 2008, 24, 12073-12076).*
Xu et al. (Langmuir 22.19 (2006): 7943-7946).*
Frenz et al. (Lab on a Chip 9.10 (2009): 1344-1348; published online Dec. 19, 2008) (Year: 2008).*
Baret et al.( Lab on a Chip 9.13 (2009): 1850-1858; published Apr. 23, 2009) (Year: 2009).*
Adang, A.E. et al., The contribution of combinatorial chemistry to lead generation: an interim analysis, Curr Med Chem 8: 985-998 (2001).

(Continued)

*Primary Examiner* — Tracy Vivlemore
*Assistant Examiner* — Sahana S Kaup
(74) *Attorney, Agent, or Firm* — Brown Rudnick LLP; Thomas C. Meyers

(57) ABSTRACT

The present invention generally relates to systems and methods to create stable emulsions with low rates of exchange of molecules between microdroplets.

22 Claims, 9 Drawing Sheets

(56) References Cited

U.S. PATENT DOCUMENTS

| | | |
|---|---|---|
| 4,585,209 A | 4/1986 | Aine et al. |
| 4,618,476 A | 10/1986 | Columbus |
| 4,675,285 A | 6/1987 | Clark et al. |
| 4,676,274 A | 6/1987 | Brown |
| 4,683,195 A | 7/1987 | Mullis et al. |
| 4,683,202 A | 7/1987 | Mullis |
| 4,739,044 A | 4/1988 | Stabinsky |
| 4,757,141 A | 7/1988 | Fung et al. |
| 4,767,515 A | 8/1988 | Scott et al. |
| 4,767,929 A | 8/1988 | Valentine |
| 4,779,805 A | 10/1988 | Jackson et al. |
| 4,801,086 A | 1/1989 | Noakes |
| 4,801,529 A | 1/1989 | Perlman |
| 4,829,996 A | 5/1989 | Noakes et al. |
| 4,853,336 A | 8/1989 | Saros et al. |
| 4,865,444 A | 9/1989 | Green et al. |
| 4,883,750 A | 11/1989 | Whiteley et al. |
| 4,908,112 A | 3/1990 | Pace |
| 4,931,225 A | 6/1990 | Cheng |
| 4,941,959 A | 7/1990 | Scott |
| 4,962,885 A | 10/1990 | Coffee |
| 4,963,498 A | 10/1990 | Hillman et al. |
| 4,981,580 A | 1/1991 | Auer |
| 4,996,004 A | 2/1991 | Bucheler et al. |
| 5,091,652 A | 2/1992 | Mathies et al. |
| 5,096,615 A | 3/1992 | Prescott et al. |
| 5,122,360 A | 6/1992 | Harris et al. |
| 5,180,662 A | 1/1993 | Sitkovsky |
| 5,185,099 A | 2/1993 | Delpuech et al. |
| 5,188,290 A | 2/1993 | Gebauer et al. |
| 5,188,291 A | 2/1993 | Cross |
| 5,204,112 A | 4/1993 | Hope et al. |
| 5,207,973 A | 5/1993 | Harris et al. |
| 5,241,159 A | 8/1993 | Chatteriee et al. |
| 5,260,466 A | 11/1993 | McGibbon |
| 5,262,027 A | 11/1993 | Scott |
| 5,270,163 A | 12/1993 | Gold et al. |
| 5,296,375 A | 3/1994 | Kricka et al. |
| 5,304,487 A | 4/1994 | Wilding et al. |
| 5,310,653 A | 5/1994 | Hanausek-Walaszek et al. |
| 5,313,009 A | 5/1994 | Guenkel et al. |
| 5,344,594 A | 9/1994 | Sheridon |
| 5,378,957 A | 1/1995 | Kelly |
| 5,397,605 A | 3/1995 | Barbieri et al. |
| 5,399,461 A | 3/1995 | Van et al. |
| 5,399,491 A | 3/1995 | Kacian et al. |
| 5,403,617 A | 4/1995 | Haaland |
| 5,413,924 A | 5/1995 | Kosak et al. |
| 5,417,235 A | 5/1995 | Wise et al. |
| 5,427,946 A | 6/1995 | Kricka et al. |
| 5,445,934 A | 8/1995 | Fodor et al. |
| 5,452,878 A | 9/1995 | Gravesen et al. |
| 5,452,955 A | 9/1995 | Lundstrom |
| 5,454,472 A | 10/1995 | Benecke et al. |
| 5,460,945 A | 10/1995 | Springer et al. |
| 5,475,096 A | 12/1995 | Gold et al. |
| 5,480,614 A | 1/1996 | Kamahori |
| 5,486,335 A | 1/1996 | Wilding et al. |
| 5,498,392 A | 3/1996 | Wilding et al. |
| 5,500,415 A | 3/1996 | Dollat et al. |
| 5,503,851 A | 4/1996 | Mank et al. |
| 5,512,131 A | 4/1996 | Kumar et al. |
| 5,516,635 A | 5/1996 | Ekins et al. |
| 5,518,709 A | 5/1996 | Sutton et al. |
| 5,523,162 A | 6/1996 | Franz et al. |
| 5,587,128 A | 12/1996 | Wilding et al. |
| 5,604,097 A | 2/1997 | Brenner |
| 5,612,188 A | 3/1997 | Shuler et al. |
| 5,616,478 A | 4/1997 | Chetverin et al. |
| 5,617,997 A | 4/1997 | Kobayashi et al. |
| 5,635,358 A | 6/1997 | Wilding et al. |
| 5,636,400 A | 6/1997 | Young |
| 5,641,658 A | 6/1997 | Adams et al. |
| 5,643,729 A | 7/1997 | Taniguchi et al. |
| 5,655,517 A | 8/1997 | Coffee |
| 5,656,155 A | 8/1997 | Norcross et al. |
| 5,661,222 A | 8/1997 | Hare |
| 5,662,874 A | 9/1997 | David |
| 5,670,325 A | 9/1997 | Lapidus et al. |
| 5,681,600 A | 10/1997 | Antinone et al. |
| 5,695,934 A | 12/1997 | Brenner |
| 5,726,026 A | 3/1998 | Wilding et al. |
| 5,726,404 A | 3/1998 | Brody |
| 5,733,526 A | 3/1998 | Trevino et al. |
| 5,739,036 A | 4/1998 | Parris |
| 5,744,366 A | 4/1998 | Kricka et al. |
| 5,750,988 A | 5/1998 | Apffel et al. |
| 5,762,775 A | 6/1998 | DePaoli et al. |
| 5,779,868 A | 7/1998 | Parce et al. |
| 5,783,431 A | 7/1998 | Peterson et al. |
| 5,840,506 A | 11/1998 | Giordano |
| 5,846,719 A | 12/1998 | Brenner et al. |
| 5,849,491 A | 12/1998 | Radomski et al. |
| 5,858,187 A | 1/1999 | Ramsey et al. |
| 5,858,655 A | 1/1999 | Arnold |
| 5,858,670 A | 1/1999 | Lam et al. |
| 5,863,722 A | 1/1999 | Brenner |
| 5,868,322 A | 2/1999 | Loucks, Jr. et al. |
| 5,872,010 A | 2/1999 | Karger et al. |
| 5,876,771 A | 3/1999 | Sizer et al. |
| 5,880,071 A | 3/1999 | Parce et al. |
| 5,882,680 A | 3/1999 | Suzuki et al. |
| 5,884,846 A | 3/1999 | Tan |
| 5,887,755 A | 3/1999 | Hood, III |
| 5,888,746 A | 3/1999 | Tabiti et al. |
| 5,888,778 A | 3/1999 | Shuber |
| 5,904,933 A | 5/1999 | Riess et al. |
| 5,921,678 A | 7/1999 | Desai et al. |
| 5,927,852 A | 7/1999 | Serafin |
| 5,928,870 A | 7/1999 | Lapidus et al. |
| 5,932,100 A | 8/1999 | Yager et al. |
| 5,935,331 A | 8/1999 | Naka et al. |
| 5,942,056 A | 8/1999 | Singh |
| 5,942,443 A | 8/1999 | Parce et al. |
| 5,958,203 A | 9/1999 | Parce et al. |
| 5,972,187 A | 10/1999 | Parce et al. |
| 5,980,936 A | 11/1999 | Krafft et al. |
| 5,989,815 A | 11/1999 | Skolnick et al. |
| 5,989,892 A | 11/1999 | Nishimaki et al. |
| 5,995,341 A | 11/1999 | Tanaka et al. |
| 5,997,636 A | 12/1999 | Gamarnik et al. |
| 6,008,003 A | 12/1999 | Haak-Frendscho et al. |
| 6,023,540 A | 2/2000 | Walt et al. |
| 6,028,066 A | 2/2000 | Unger |
| 6,042,709 A | 3/2000 | Parce et al. |
| 6,045,755 A | 4/2000 | Lebl et al. |
| 6,046,056 A | 4/2000 | Parce et al. |
| 6,048,551 A | 4/2000 | Hilfinger et al. |
| 6,068,199 A | 5/2000 | Coffee |
| 6,080,295 A | 6/2000 | Parce et al. |
| 6,086,740 A | 7/2000 | Kennedy |
| 6,096,495 A | 8/2000 | Kasai et al. |
| 6,103,537 A | 8/2000 | Ullman et al. |
| 6,105,571 A | 8/2000 | Coffee |
| 6,105,877 A | 8/2000 | Coffee |
| 6,116,516 A | 9/2000 | Ganan-Calvo |
| 6,118,849 A | 9/2000 | Tanimori et al. |
| 6,119,953 A | 9/2000 | Ganan-Calvo et al. |
| 6,120,666 A | 9/2000 | Jacobson et al. |
| 6,124,388 A | 9/2000 | Takai et al. |
| 6,124,439 A | 9/2000 | Friedman et al. |
| 6,130,052 A | 10/2000 | Van Baren et al. |
| 6,130,098 A | 10/2000 | Handique et al. |
| 6,137,214 A | 10/2000 | Raina |
| 6,138,077 A | 10/2000 | Brenner |
| 6,139,303 A | 10/2000 | Reed et al. |
| 6,140,053 A | 10/2000 | Koster |
| 6,143,496 A | 11/2000 | Brown et al. |
| 6,149,789 A | 11/2000 | Benecke et al. |
| 6,150,180 A | 11/2000 | Parce et al. |
| 6,150,516 A | 11/2000 | Brenner et al. |
| 6,165,778 A | 12/2000 | Kedar |
| 6,171,796 B1 | 1/2001 | An et al. |
| 6,171,850 B1 | 1/2001 | Nagle et al. |

(56) References Cited

U.S. PATENT DOCUMENTS

| | | |
|---|---|---|
| 6,172,214 B1 | 1/2001 | Brenner |
| 6,172,218 B1 | 1/2001 | Brenner |
| 6,174,160 B1 | 1/2001 | Lee et al. |
| 6,174,469 B1 | 1/2001 | Ganan-Calvo |
| 6,180,372 B1 | 1/2001 | Franzen |
| 6,184,012 B1 | 2/2001 | Neri et al. |
| 6,187,214 B1 | 2/2001 | Ganan-Calvo |
| 6,189,803 B1 | 2/2001 | Ganan-Calvo |
| 6,196,525 B1 | 3/2001 | Ganan-Calvo |
| 6,197,335 B1 | 3/2001 | Sherman |
| 6,197,835 B1 | 3/2001 | Ganan-Calvo |
| 6,203,993 B1 | 3/2001 | Shuber et al. |
| 6,210,396 B1 | 4/2001 | MacDonald et al. |
| 6,210,891 B1 | 4/2001 | Nyren et al. |
| 6,210,896 B1 | 4/2001 | Chan |
| 6,214,558 B1 | 4/2001 | Shuber et al. |
| 6,221,654 B1 | 4/2001 | Quake et al. |
| 6,227,466 B1 | 5/2001 | Hartman et al. |
| 6,234,402 B1 | 5/2001 | Ganan-Calvo |
| 6,235,383 B1 | 5/2001 | Hong et al. |
| 6,235,475 B1 | 5/2001 | Brenner et al. |
| 6,241,159 B1 | 6/2001 | Ganan-Calvo et al. |
| 6,243,373 B1 | 6/2001 | Turock |
| 6,248,378 B1 | 6/2001 | Ganan-Calvo |
| 6,251,661 B1 | 6/2001 | Urabe et al. |
| 6,252,129 B1 | 6/2001 | Coffee |
| 6,258,568 B1 | 7/2001 | Nyren |
| 6,258,858 B1 | 7/2001 | Nakajima et al. |
| 6,263,222 B1 | 7/2001 | Diab et al. |
| 6,266,459 B1 | 7/2001 | Walt et al. |
| 6,267,353 B1 | 7/2001 | Friedline et al. |
| 6,267,858 B1 | 7/2001 | Parce et al. |
| 6,268,165 B1 | 7/2001 | O'Brien |
| 6,268,222 B1 | 7/2001 | Chandler et al. |
| 6,274,320 B1 | 8/2001 | Rothberg et al. |
| 6,274,337 B1 | 8/2001 | Parce et al. |
| 6,294,344 B1 | 9/2001 | O'Brien |
| 6,296,673 B1 | 10/2001 | Santarsiero et al. |
| 6,299,145 B1 | 10/2001 | Ganan-Calvo |
| 6,301,055 B1 | 10/2001 | Legrand et al. |
| 6,306,659 B1 | 10/2001 | Parce et al. |
| 6,310,354 B1 | 10/2001 | Hanninen et al. |
| 6,310,653 B1 | 10/2001 | Malcolm, Jr. et al. |
| 6,316,208 B1 | 11/2001 | Roberts et al. |
| 6,316,213 B1 | 11/2001 | O'Brien |
| 6,318,640 B1 | 11/2001 | Coffee |
| 6,336,463 B1 | 1/2002 | Ohta |
| 6,344,325 B1 | 2/2002 | Quake et al. |
| 6,352,828 B1 | 3/2002 | Brenner |
| 6,355,193 B1 | 3/2002 | Stott |
| 6,355,198 B1 | 3/2002 | Kim et al. |
| 6,357,670 B2 | 3/2002 | Ganan-Calvo |
| 6,386,463 B1 | 5/2002 | Ganan-Calvo |
| 6,391,559 B1 | 5/2002 | Brown et al. |
| 6,394,429 B2 | 5/2002 | Ganan-Calvo |
| 6,399,339 B1 | 6/2002 | Wolberg et al. |
| 6,399,389 B1 | 6/2002 | Parce et al. |
| 6,403,373 B1 | 6/2002 | Scanlan et al. |
| 6,405,936 B1 | 6/2002 | Ganan-Calvo |
| 6,408,878 B2 | 6/2002 | Unger et al. |
| 6,409,832 B2 | 6/2002 | Weigl et al. |
| 6,429,025 B1 | 8/2002 | Parce et al. |
| 6,429,148 B1 | 8/2002 | Chu et al. |
| 6,432,143 B2 | 8/2002 | Kubiak et al. |
| 6,432,148 B1 | 8/2002 | Ganan-Calvo |
| 6,432,630 B1 | 8/2002 | Blankenstein |
| 6,439,103 B1 | 8/2002 | Miller |
| 6,440,706 B1 | 8/2002 | Vogelstein et al. |
| 6,450,139 B1 | 9/2002 | Watanabe |
| 6,450,189 B1 | 9/2002 | Ganan-Calvo |
| 6,454,193 B1 | 9/2002 | Busick et al. |
| 6,464,336 B1 | 10/2002 | Sharma |
| 6,464,886 B2 | 10/2002 | Ganan-Calvo |
| 6,475,441 B1 | 11/2002 | Parce et al. |
| 6,481,648 B1 | 11/2002 | Zimmermann |
| 6,489,103 B1 | 12/2002 | Griffiths et al. |
| 6,503,933 B1 | 1/2003 | Moloney et al. |
| 6,506,609 B1 | 1/2003 | Wada et al. |
| 6,508,988 B1 | 1/2003 | Van Dam et al. |
| 6,520,425 B1 | 2/2003 | Reneker |
| 6,524,456 B1 | 2/2003 | Ramsey et al. |
| 6,540,395 B2 | 4/2003 | Muhlbauer et al. |
| 6,540,895 B1 | 4/2003 | Spence et al. |
| 6,551,836 B1 | 4/2003 | Chow et al. |
| 6,553,944 B1 | 4/2003 | Allen et al. |
| 6,553,960 B1 | 4/2003 | Yoshikawa et al. |
| 6,554,202 B2 | 4/2003 | Ganan-Calvo |
| 6,557,334 B2 | 5/2003 | Jager |
| 6,557,834 B2 | 5/2003 | Ganan-Calvo |
| 6,558,944 B1 | 5/2003 | Parce et al. |
| 6,558,960 B1 | 5/2003 | Parce et al. |
| 6,560,030 B2 | 5/2003 | Legrand et al. |
| 6,565,010 B2 | 5/2003 | Anderson et al. |
| 6,569,631 B1 | 5/2003 | Pantoliano et al. |
| 6,576,420 B1 | 6/2003 | Carson et al. |
| 6,591,852 B1 | 7/2003 | McNeely et al. |
| 6,592,321 B2 | 7/2003 | Bonker et al. |
| 6,592,821 B1 | 7/2003 | Wada et al. |
| 6,608,726 B2 | 8/2003 | Legrand et al. |
| 6,610,499 B1 | 8/2003 | Fulwyler et al. |
| 6,614,598 B1 | 9/2003 | Quake et al. |
| 6,627,603 B1 | 9/2003 | Bibette et al. |
| 6,630,006 B2 | 10/2003 | Santarsiero et al. |
| 6,630,353 B1 | 10/2003 | Parce et al. |
| 6,632,619 B1 | 10/2003 | Harrison et al. |
| 6,638,749 B1 | 10/2003 | Beckman et al. |
| 6,645,432 B1 | 11/2003 | Anderson et al. |
| 6,646,253 B1 | 11/2003 | Rohwer et al. |
| 6,653,626 B2 | 11/2003 | Fischer et al. |
| 6,656,267 B2 | 12/2003 | Newman |
| 6,659,370 B1 | 12/2003 | Inoue |
| 6,660,252 B2 | 12/2003 | Matathia et al. |
| 6,670,142 B2 | 12/2003 | Lau et al. |
| 6,679,441 B1 | 1/2004 | Borra et al. |
| 6,680,178 B2 | 1/2004 | Harris et al. |
| 6,682,890 B2 | 1/2004 | Mack et al. |
| 6,717,136 B2 | 4/2004 | Andersson et al. |
| 6,729,561 B2 | 5/2004 | Hirae et al. |
| 6,739,036 B2 | 5/2004 | Koike et al. |
| 6,744,046 B2 | 6/2004 | Valaskovic et al. |
| 6,752,922 B2 | 6/2004 | Huang et al. |
| 6,753,147 B2 | 6/2004 | Vogelstein et al. |
| 6,766,817 B2 | 7/2004 | da Silva |
| 6,767,194 B2 | 7/2004 | Jeon et al. |
| 6,767,704 B2 | 7/2004 | Waldman et al. |
| 6,790,328 B2 | 9/2004 | Jacobson et al. |
| 6,793,753 B2 | 9/2004 | Unger et al. |
| 6,797,056 B2 | 9/2004 | David |
| 6,800,849 B2 | 10/2004 | Staats |
| 6,806,058 B2 | 10/2004 | Jesperson et al. |
| 6,808,382 B2 | 10/2004 | Lanfranchi |
| 6,808,882 B2 | 10/2004 | Griffiths et al. |
| 6,814,980 B2 | 11/2004 | Levy et al. |
| 6,818,395 B1 | 11/2004 | Quake et al. |
| 6,832,787 B1 | 12/2004 | Renzi |
| 6,833,242 B2 | 12/2004 | Quake et al. |
| 6,841,350 B2 | 1/2005 | Ogden et al. |
| 6,872,250 B2 | 3/2005 | David et al. |
| 6,890,487 B1 | 5/2005 | Sklar et al. |
| 6,897,018 B1 | 5/2005 | Yuan et al. |
| 6,905,844 B2 | 6/2005 | Kim |
| 6,918,404 B2 | 7/2005 | Dias da Silva |
| 6,926,313 B1 | 8/2005 | Renzi |
| 6,935,768 B2 | 8/2005 | Lowe et al. |
| 6,936,417 B2 | 8/2005 | Orntoft |
| 6,942,978 B1 | 9/2005 | O'Brien |
| 6,949,342 B2 | 9/2005 | Golub et al. |
| 6,960,437 B2 | 11/2005 | Enzelberger et al. |
| 6,974,667 B2 | 12/2005 | Horne et al. |
| 6,998,232 B1 | 2/2006 | Feinstein et al. |
| 7,022,472 B2 | 4/2006 | Robbins et al. |
| 7,041,481 B2 | 5/2006 | Anderson et al. |
| 7,049,072 B2 | 5/2006 | Seshi |
| 7,056,674 B2 | 6/2006 | Baker et al. |

(56) References Cited

U.S. PATENT DOCUMENTS

| | | |
|---|---|---|
| 7,057,026 B2 | 6/2006 | Barnes et al. |
| 7,066,586 B2 | 6/2006 | da Silva |
| 7,068,874 B2 | 6/2006 | Wang et al. |
| 7,078,180 B2 | 7/2006 | Genetta |
| 7,081,192 B1 | 7/2006 | Wang et al. |
| 7,081,340 B2 | 7/2006 | Baker et al. |
| 7,090,983 B1 | 8/2006 | Muramatsu et al. |
| 7,115,230 B2 | 10/2006 | Sundararajan et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,153,700 B1 | 12/2006 | Pardee et al. |
| 7,156,917 B2 | 1/2007 | Moriyama et al. |
| 7,163,801 B2 | 1/2007 | Reed |
| 7,169,560 B2 | 1/2007 | Lapidus et al. |
| 7,171,311 B2 | 1/2007 | Dai et al. |
| 7,198,899 B2 | 4/2007 | Schleyer et al. |
| 7,204,431 B2 | 4/2007 | Li et al. |
| 7,229,770 B1 | 6/2007 | Price et al. |
| 7,252,943 B2 | 8/2007 | Griffiths et al. |
| 7,267,938 B2 | 9/2007 | Anderson et al. |
| 7,268,167 B2 | 9/2007 | Higuchi et al. |
| 7,282,337 B1 | 10/2007 | Harris |
| 7,291,462 B2 | 11/2007 | O'Brien et al. |
| 7,294,503 B2 | 11/2007 | Quake et al. |
| 7,300,765 B2 | 11/2007 | Patel |
| 7,308,364 B2 | 12/2007 | Shaughnessy et al. |
| 7,314,721 B2 | 1/2008 | Gure et al. |
| 7,316,906 B2 | 1/2008 | Chiorazzi et al. |
| 7,326,529 B2 | 2/2008 | Ali et al. |
| 7,332,280 B2 | 2/2008 | Levy et al. |
| 7,332,590 B2 | 2/2008 | Nacht et al. |
| 7,341,211 B2 | 3/2008 | Ganan Calvo et al. |
| 7,348,142 B2 | 3/2008 | Wang |
| 7,358,231 B1 | 4/2008 | McCaffey et al. |
| 7,361,474 B2 | 4/2008 | Siegler |
| 7,364,862 B2 | 4/2008 | Ali et al. |
| 7,368,255 B2 | 5/2008 | Bae et al. |
| 7,378,233 B2 | 5/2008 | Sidransky et al. |
| 7,378,280 B2 | 5/2008 | Quake et al. |
| 7,390,463 B2 | 6/2008 | He et al. |
| 7,393,665 B2 | 7/2008 | Brenner |
| 7,416,851 B2 | 8/2008 | Davi et al. |
| 7,429,467 B2 * | 9/2008 | Holliger ............... A61K 9/107 435/193 |
| 7,432,064 B2 | 10/2008 | Salceda et al. |
| 7,442,507 B2 | 10/2008 | Polsky et al. |
| 7,449,303 B2 | 11/2008 | Coignet |
| 7,468,271 B2 | 12/2008 | Golovchenko et al. |
| 7,473,530 B2 | 1/2009 | Huttemann |
| 7,473,531 B1 | 1/2009 | Domon et al. |
| 7,476,506 B2 | 1/2009 | Schleyer et al. |
| 7,479,370 B2 | 1/2009 | Coignet |
| 7,479,371 B2 | 1/2009 | Ando et al. |
| 7,479,376 B2 | 1/2009 | Waldman et al. |
| 7,482,129 B2 | 1/2009 | Soyupak et al. |
| 7,501,244 B2 | 3/2009 | Reinhard et al. |
| 7,504,214 B2 | 3/2009 | Erlander et al. |
| 7,507,532 B2 | 3/2009 | Chang et al. |
| 7,507,541 B2 | 3/2009 | Raitano et al. |
| 7,510,707 B2 | 3/2009 | Platica et al. |
| 7,510,842 B2 | 3/2009 | Podust et al. |
| 7,514,209 B2 | 4/2009 | Dai et al. |
| 7,514,210 B2 | 4/2009 | Holliger et al. |
| 7,524,633 B2 | 4/2009 | Sidransky |
| 7,527,933 B2 | 5/2009 | Sahin et al. |
| 7,537,897 B2 | 5/2009 | Brenner et al. |
| 7,541,383 B2 | 6/2009 | Fu et al. |
| 7,544,473 B2 | 6/2009 | Brenner |
| 7,556,776 B2 | 7/2009 | Fraden et al. |
| 7,582,446 B2 | 9/2009 | Griffiths et al. |
| 7,622,081 B2 | 11/2009 | Chou et al. |
| 7,632,562 B2 | 12/2009 | Nair et al. |
| 7,635,562 B2 | 12/2009 | Harris et al. |
| 7,638,276 B2 | 12/2009 | Griffiths et al. |
| 7,655,435 B2 | 2/2010 | Holliger et al. |
| 7,655,470 B2 | 2/2010 | Ismagilov et al. |
| 7,666,593 B2 | 2/2010 | Lapidus |
| 7,691,576 B2 | 4/2010 | Holliger et al. |
| 7,698,287 B2 | 4/2010 | Becker et al. |
| 7,708,949 B2 | 5/2010 | Stone et al. |
| 7,718,578 B2 | 5/2010 | Griffiths et al. |
| 7,736,890 B2 | 6/2010 | Sia et al. |
| 7,741,130 B2 | 6/2010 | Lee, Jr. et al. |
| 7,814,175 B1 | 10/2010 | Chang et al. |
| 7,824,889 B2 | 11/2010 | Vogelstein et al. |
| 7,888,017 B2 | 2/2011 | Quake et al. |
| 7,897,044 B2 | 3/2011 | Hoyos et al. |
| 7,897,341 B2 | 3/2011 | Griffiths et al. |
| 7,901,939 B2 | 3/2011 | Ismagilov et al. |
| 7,968,287 B2 | 6/2011 | Griffiths et al. |
| 8,012,382 B2 | 9/2011 | Kim et al. |
| 8,153,402 B2 | 4/2012 | Holliger et al. |
| 2001/0010338 A1 | 8/2001 | Ganan-Calvo |
| 2001/0020011 A1 | 9/2001 | Mathiowitz et al. |
| 2001/0023078 A1 | 9/2001 | Bawendi et al. |
| 2001/0029983 A1 | 10/2001 | Unger et al. |
| 2001/0034031 A1 | 10/2001 | Short et al. |
| 2001/0041343 A1 | 11/2001 | Pankowsky |
| 2001/0041344 A1 | 11/2001 | Sepetov et al. |
| 2001/0042793 A1 | 11/2001 | Ganan-Calvo |
| 2001/0048900 A1 | 12/2001 | Bardell et al. |
| 2001/0050881 A1 | 12/2001 | Depaoli et al. |
| 2002/0004532 A1 | 1/2002 | Matathia et al. |
| 2002/0005354 A1 | 1/2002 | Spence et al. |
| 2002/0008028 A1 | 1/2002 | Jacobson et al. |
| 2002/0012971 A1 | 1/2002 | Mehta |
| 2002/0022038 A1 | 2/2002 | Biatry et al. |
| 2002/0022261 A1 | 2/2002 | Anderson et al. |
| 2002/0033422 A1 | 3/2002 | Ganan-Calvo |
| 2002/0036139 A1 | 3/2002 | Becker et al. |
| 2002/0058332 A1 | 5/2002 | Quake et al. |
| 2002/0067800 A1 | 6/2002 | Newman et al. |
| 2002/0119459 A1 | 8/2002 | Griffiths |
| 2002/0143437 A1 | 10/2002 | Handique et al. |
| 2002/0155080 A1 | 10/2002 | Glenn et al. |
| 2002/0158027 A1 | 10/2002 | Moon et al. |
| 2002/0164271 A1 | 11/2002 | Ho |
| 2002/0164629 A1 | 11/2002 | Quake et al. |
| 2003/0012586 A1 | 1/2003 | Iwata et al. |
| 2003/0015425 A1 | 1/2003 | Bohm et al. |
| 2003/0017579 A1 | 1/2003 | Corn et al. |
| 2003/0039169 A1 | 2/2003 | Ehrfeld et al. |
| 2003/0059764 A1 | 3/2003 | Ravkin et al. |
| 2003/0061687 A1 | 4/2003 | Hansen et al. |
| 2003/0064414 A1 | 4/2003 | Benecky et al. |
| 2003/0082795 A1 | 5/2003 | Shuler et al. |
| 2003/0124586 A1 | 7/2003 | Griffiths et al. |
| 2003/0144260 A1 | 7/2003 | Gilon |
| 2003/0148544 A1 | 8/2003 | Nie et al. |
| 2003/0183525 A1 | 10/2003 | Elrod et al. |
| 2003/0224509 A1 | 12/2003 | Moon et al. |
| 2003/0229376 A1 | 12/2003 | Sandhu |
| 2003/0230486 A1 | 12/2003 | Chien et al. |
| 2003/0232356 A1 | 12/2003 | Dooley et al. |
| 2004/0005582 A1 | 1/2004 | Shipwash |
| 2004/0005594 A1 | 1/2004 | Holliger et al. |
| 2004/0018525 A1 | 1/2004 | Wirtz et al. |
| 2004/0027915 A1 | 2/2004 | Lowe et al. |
| 2004/0037813 A1 | 2/2004 | Simpson et al. |
| 2004/0041093 A1 | 3/2004 | Schultz et al. |
| 2004/0050946 A1 | 3/2004 | Wang et al. |
| 2004/0053247 A1 | 3/2004 | Cordon-Cardo et al. |
| 2004/0068019 A1 | 4/2004 | Higuchi et al. |
| 2004/0071781 A1 | 4/2004 | Chattopadhyay et al. |
| 2004/0079881 A1 | 4/2004 | Fischer et al. |
| 2004/0096515 A1 | 5/2004 | Bausch et al. |
| 2004/0136497 A1 | 7/2004 | Meldrum et al. |
| 2004/0146921 A1 | 7/2004 | Eveleigh et al. |
| 2004/0159633 A1 | 8/2004 | Whitesides et al. |
| 2004/0181131 A1 | 9/2004 | Maynard et al. |
| 2004/0181343 A1 | 9/2004 | Wigstrom et al. |
| 2004/0182712 A1 | 9/2004 | Basol |
| 2004/0188254 A1 | 9/2004 | Spaid |

(56) References Cited

U.S. PATENT DOCUMENTS

| | | |
|---|---|---|
| 2004/0224419 A1 | 11/2004 | Zheng et al. |
| 2004/0253731 A1 | 12/2004 | Holliger et al. |
| 2004/0258203 A1 | 12/2004 | Yamano et al. |
| 2005/0032238 A1 | 2/2005 | Karp et al. |
| 2005/0032240 A1 | 2/2005 | Lee et al. |
| 2005/0037392 A1 | 2/2005 | Griffiths et al. |
| 2005/0042648 A1 | 2/2005 | Griffiths et al. |
| 2005/0048467 A1 | 3/2005 | Sastry et al. |
| 2005/0064460 A1 | 3/2005 | Holliger et al. |
| 2005/0069920 A1 | 3/2005 | Griffiths et al. |
| 2005/0079510 A1 | 4/2005 | Berka et al. |
| 2005/0084923 A1 | 4/2005 | Mueller et al. |
| 2005/0087122 A1 | 4/2005 | Ismagliov et al. |
| 2005/0095611 A1 | 5/2005 | Chan et al. |
| 2005/0100895 A1 | 5/2005 | Waldman et al. |
| 2005/0129582 A1 | 6/2005 | Breidford et al. |
| 2005/0152908 A1 | 7/2005 | Liew et al. |
| 2005/0164239 A1 | 7/2005 | Griffiths et al. |
| 2005/0170431 A1 | 8/2005 | Ibrahim et al. |
| 2005/0172476 A1 | 8/2005 | Stone et al. |
| 2005/0183995 A1 | 8/2005 | Deshpande et al. |
| 2005/0207940 A1 | 9/2005 | Butler et al. |
| 2005/0221339 A1 | 10/2005 | Griffiths et al. |
| 2005/0226742 A1 | 10/2005 | Unger et al. |
| 2005/0227264 A1 | 10/2005 | Nobile et al. |
| 2005/0260566 A1 | 11/2005 | Fischer et al. |
| 2005/0272159 A1 | 12/2005 | Ismagilov et al. |
| 2006/0003347 A1 | 1/2006 | Griffiths et al. |
| 2006/0003429 A1 | 1/2006 | Frost et al. |
| 2006/0003439 A1 | 1/2006 | Ismagilov et al. |
| 2006/0036348 A1 | 2/2006 | Handique et al. |
| 2006/0046257 A1 | 3/2006 | Pollock et al. |
| 2006/0051329 A1 | 3/2006 | Lee et al. |
| 2006/0078888 A1 | 4/2006 | Griffiths et al. |
| 2006/0078893 A1 | 4/2006 | Griffiths et al. |
| 2006/0094119 A1 | 5/2006 | Ismagilov et al. |
| 2006/0108012 A1 | 5/2006 | Barrow et al. |
| 2006/0110759 A1 | 5/2006 | Paris et al. |
| 2006/0115821 A1 | 6/2006 | Einstein et al. |
| 2006/0147909 A1 | 7/2006 | Rarbach et al. |
| 2006/0153924 A1 | 7/2006 | Griffiths et al. |
| 2006/0154298 A1 | 7/2006 | Griffiths et al. |
| 2006/0160762 A1 | 7/2006 | Zetter et al. |
| 2006/0163385 A1 | 7/2006 | Link et al. |
| 2006/0169800 A1 | 8/2006 | Rosell et al. |
| 2006/0195269 A1 | 8/2006 | Yeatman et al. |
| 2006/0223127 A1 | 10/2006 | Yip et al. |
| 2006/0234254 A1 | 10/2006 | An et al. |
| 2006/0234259 A1 | 10/2006 | Rubin et al. |
| 2006/0252057 A1 | 11/2006 | Raponi et al. |
| 2006/0258841 A1 | 11/2006 | Michl et al. |
| 2006/0263888 A1 | 11/2006 | Fritz et al. |
| 2006/0269558 A1 | 11/2006 | Murphy et al. |
| 2006/0269971 A1 | 11/2006 | Diamandis |
| 2006/0281089 A1 | 12/2006 | Gibson et al. |
| 2007/0003442 A1 | 1/2007 | Link et al. |
| 2007/0026439 A1 | 2/2007 | Faulstich et al. |
| 2007/0053896 A1 | 3/2007 | Ahmed et al. |
| 2007/0054119 A1 | 3/2007 | Garstecki et al. |
| 2007/0056853 A1 | 3/2007 | Aizenberg et al. |
| 2007/0077572 A1 | 4/2007 | Tawfik et al. |
| 2007/0077579 A1 | 4/2007 | Griffiths et al. |
| 2007/0092914 A1 | 4/2007 | Griffiths et al. |
| 2007/0120899 A1 | 5/2007 | Ohnishi et al. |
| 2007/0154889 A1 | 7/2007 | Wang |
| 2007/0166705 A1 | 7/2007 | Milton et al. |
| 2007/0184439 A1 | 8/2007 | Guilford et al. |
| 2007/0184489 A1 | 8/2007 | Griffiths et al. |
| 2007/0195127 A1 | 8/2007 | Ahn et al. |
| 2007/0259351 A1 | 11/2007 | Chinitz et al. |
| 2007/0259368 A1 | 11/2007 | An et al. |
| 2007/0259374 A1 | 11/2007 | Griffiths et al. |
| 2007/0292869 A1 | 12/2007 | Becker et al. |
| 2008/0003142 A1* | 1/2008 | Link ............... B01F 3/0807 422/82.08 |
| 2008/0009005 A1 | 1/2008 | Kruk |
| 2008/0014589 A1 | 1/2008 | Link et al. |
| 2008/0014590 A1 | 1/2008 | Dahary et al. |
| 2008/0020940 A1 | 1/2008 | Stedronsky et al. |
| 2008/0021330 A1 | 1/2008 | Hwang et al. |
| 2008/0023330 A1 | 1/2008 | Viovy et al. |
| 2008/0038754 A1 | 2/2008 | Farias-Eisner et al. |
| 2008/0044828 A1 | 2/2008 | Kwok |
| 2008/0050378 A1 | 2/2008 | Nakamura et al. |
| 2008/0050723 A1 | 2/2008 | Belacel et al. |
| 2008/0053205 A1 | 3/2008 | Pollack et al. |
| 2008/0057514 A1 | 3/2008 | Goldenring |
| 2008/0058432 A1 | 3/2008 | Wang et al. |
| 2008/0063227 A1 | 3/2008 | Rohrseitz |
| 2008/0064047 A1 | 3/2008 | Zetter et al. |
| 2008/0081330 A1 | 4/2008 | Kahvejian |
| 2008/0081333 A1 | 4/2008 | Mori et al. |
| 2008/0092973 A1 | 4/2008 | Lai |
| 2008/0113340 A1 | 5/2008 | Schlegel |
| 2008/0118462 A1 | 5/2008 | Alani et al. |
| 2008/0138806 A1 | 6/2008 | Chow et al. |
| 2008/0166772 A1 | 7/2008 | Hollinger et al. |
| 2008/0171078 A1 | 7/2008 | Gray |
| 2008/0176211 A1 | 7/2008 | Spence et al. |
| 2008/0176236 A1 | 7/2008 | Tsao et al. |
| 2008/0181850 A1 | 7/2008 | Thaxton et al. |
| 2008/0206756 A1 | 8/2008 | Lee et al. |
| 2008/0222741 A1 | 9/2008 | Chinnaiyan |
| 2008/0234138 A1 | 9/2008 | Shaughnessy et al. |
| 2008/0234139 A1 | 9/2008 | Shaughnessy et al. |
| 2008/0236258 A1* | 10/2008 | Oddie ............... G01N 1/38 73/64.56 |
| 2008/0268473 A1 | 10/2008 | Moses et al. |
| 2008/0269157 A1 | 10/2008 | Srivastava et al. |
| 2008/0274908 A1 | 11/2008 | Chang |
| 2008/0280302 A1 | 11/2008 | Kebebew |
| 2008/0286199 A1 | 11/2008 | Livingston et al. |
| 2008/0286801 A1 | 11/2008 | Arjol et al. |
| 2008/0286811 A1 | 11/2008 | Moses et al. |
| 2008/0293578 A1 | 11/2008 | Shaugnessy et al. |
| 2008/0311570 A1 | 12/2008 | Lai |
| 2008/0311604 A1 | 12/2008 | Elting et al. |
| 2009/0004687 A1 | 1/2009 | Mansfield et al. |
| 2009/0005254 A1 | 1/2009 | Griffiths et al. |
| 2009/0012187 A1 | 1/2009 | Chu et al. |
| 2009/0017463 A1 | 1/2009 | Bhowmick |
| 2009/0021728 A1 | 1/2009 | Heinz et al. |
| 2009/0023137 A1 | 1/2009 | Van Der Zee et al. |
| 2009/0026082 A1 | 1/2009 | Rothberg et al. |
| 2009/0029372 A1 | 1/2009 | Wewer |
| 2009/0042737 A1 | 2/2009 | Katz et al. |
| 2009/0053700 A1 | 2/2009 | Griffiths et al. |
| 2009/0053732 A1 | 2/2009 | Vermesh et al. |
| 2009/0060797 A1 | 3/2009 | Mathies et al. |
| 2009/0062144 A1 | 3/2009 | Guo |
| 2009/0068170 A1 | 3/2009 | Weitz et al. |
| 2009/0075265 A1 | 3/2009 | Budiman et al. |
| 2009/0075307 A1 | 3/2009 | Fischer et al. |
| 2009/0075311 A1 | 3/2009 | Karl |
| 2009/0081237 A1 | 3/2009 | D'Andrea et al. |
| 2009/0081685 A1 | 3/2009 | Beyer et al. |
| 2009/0087849 A1 | 4/2009 | Malinowski et al. |
| 2009/0092973 A1 | 4/2009 | Erlander et al. |
| 2009/0098542 A1 | 4/2009 | Budiman et al. |
| 2009/0098543 A1 | 4/2009 | Budiman et al. |
| 2009/0118128 A1 | 5/2009 | Liu et al. |
| 2009/0124569 A1 | 5/2009 | Bergan et al. |
| 2009/0127454 A1 | 5/2009 | Ritchie et al. |
| 2009/0127589 A1 | 5/2009 | Rothberg et al. |
| 2009/0131353 A1 | 5/2009 | Insel et al. |
| 2009/0131543 A1 | 5/2009 | Weitz et al. |
| 2009/0191565 A1 | 7/2009 | Lapidus et al. |
| 2009/0197248 A1 | 8/2009 | Griffiths et al. |
| 2009/0197772 A1 | 8/2009 | Griffiths et al. |
| 2009/0246788 A1 | 10/2009 | Albert et al. |
| 2009/0325236 A1 | 12/2009 | Griffiths et al. |
| 2010/0003687 A1 | 1/2010 | Simen et al. |
| 2010/0009353 A1 | 1/2010 | Barnes et al. |
| 2010/0022414 A1 | 1/2010 | Link et al. |

(56) References Cited

U.S. PATENT DOCUMENTS

| | | |
|---|---|---|
| 2010/0035252 A1 | 2/2010 | Rothberg et al. |
| 2010/0075436 A1 | 3/2010 | Urdea et al. |
| 2010/0105112 A1 | 4/2010 | Holtze et al. |
| 2010/0111768 A1 | 5/2010 | Banerjee et al. |
| 2010/0124759 A1 | 5/2010 | Wang et al. |
| 2010/0136544 A1 | 6/2010 | Agresti et al. |
| 2010/0137143 A1 | 6/2010 | Rothberg et al. |
| 2010/0137163 A1 | 6/2010 | Link et al. |
| 2010/0159592 A1 | 6/2010 | Holliger et al. |
| 2010/0172803 A1 | 7/2010 | Stone et al. |
| 2010/0188073 A1 | 7/2010 | Rothberg et al. |
| 2010/0197507 A1 | 8/2010 | Rothberg et al. |
| 2010/0210479 A1 | 8/2010 | Griffiths et al. |
| 2010/0213628 A1 | 8/2010 | Bausch et al. |
| 2010/0233026 A1 | 9/2010 | Ismagliov et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0000560 A1 | 1/2011 | Miller et al. |
| 2011/0142734 A1 | 6/2011 | Ismagliov et al. |
| 2011/0174622 A1 | 7/2011 | Ismagliov et al. |
| 2011/0176966 A1 | 7/2011 | Ismagliov et al. |
| 2011/0177494 A1 | 7/2011 | Ismagliov et al. |
| 2011/0177586 A1 | 7/2011 | Ismagliov et al. |
| 2011/0177609 A1 | 7/2011 | Ismagliov et al. |
| 2011/0188717 A1 | 8/2011 | Baudry et al. |
| 2011/0190146 A1 | 8/2011 | Boehm et al. |
| 2011/0244455 A1 | 10/2011 | Larson et al. |
| 2011/0250597 A1 | 10/2011 | Larson et al. |
| 2011/0275063 A1 | 11/2011 | Weitz et al. |
| 2012/0010098 A1 | 1/2012 | Griffiths et al. |
| 2012/0015382 A1 | 1/2012 | Weitz et al. |
| 2012/0015822 A1 | 1/2012 | Weitz et al. |

FOREIGN PATENT DOCUMENTS

| | | |
|---|---|---|
| CH | 563807 A5 | 7/1975 |
| DE | 4308839 C2 | 4/1997 |
| EP | 0047130 B1 | 2/1985 |
| EP | 0249007 A3 | 3/1991 |
| EP | 0476178 A1 | 3/1992 |
| EP | 0540281 B1 | 7/1996 |
| EP | 0528580 B1 | 12/1996 |
| EP | 0895120 | 2/1999 |
| EP | 1741482 | 1/2007 |
| EP | 2127736 | 12/2009 |
| GB | 0114854.3 | 4/1969 |
| GB | 1446998 | 8/1976 |
| GB | 2005224 | 4/1979 |
| GB | 2047880 | 12/1980 |
| GB | 2062225 | 5/1981 |
| GB | 2064114 | 6/1981 |
| GB | 2097692 A | 11/1982 |
| GB | 0221053.2 | 6/1989 |
| JP | 3-232525 | 10/1998 |
| JP | 2000271475 | 10/2000 |
| WO | WO-84/02000 | 5/1984 |
| WO | WO-91/05058 A1 | 4/1991 |
| WO | WO-91/07772 | 5/1991 |
| WO | WO-92/03734 | 3/1992 |
| WO | WO-92/21746 | 12/1992 |
| WO | WO-93/03151 | 2/1993 |
| WO | WO-93/08278 | 4/1993 |
| WO | WO-93/22053 | 11/1993 |
| WO | WO-93/22054 | 11/1993 |
| WO | WO-93/22055 | 11/1993 |
| WO | WO-93/22058 | 11/1993 |
| WO | WO-93/22421 | 11/1993 |
| WO | WO-94/16332 | 7/1994 |
| WO | WO-94/23738 | 10/1994 |
| WO | WO-94/24314 | 10/1994 |
| WO | WO-94/26766 | 11/1994 |
| WO | WO-98/00705 | 1/1995 |
| WO | WO-95/11922 | 5/1995 |
| WO | WO-95/19922 | 7/1995 |
| WO | WO-95/24929 | 9/1995 |
| WO | WO-95/33447 | 12/1995 |
| WO | WO-96/34112 | 10/1996 |
| WO | WO-96/38730 | 12/1996 |
| WO | WO-96/40062 | 12/1996 |
| WO | WO-96/40723 | 12/1996 |
| WO | WO-97/00125 | 1/1997 |
| WO | WO-97/00442 | 1/1997 |
| WO | WO-97/04297 | 2/1997 |
| WO | WO-97/04748 | 2/1997 |
| WO | WO-97/23140 | 7/1997 |
| WO | WO-97/28556 | 8/1997 |
| WO | WO-97/39814 | 10/1997 |
| WO | WO-97/40141 | 10/1997 |
| WO | WO-97/45644 | 12/1997 |
| WO | WO-97/47763 | 12/1997 |
| WO | WO-98/00231 | 1/1998 |
| WO | WO-98/02237 | 1/1998 |
| WO | WO-98/10267 | 3/1998 |
| WO | WO-98/13502 | 4/1998 |
| WO | WO-98/23733 | 6/1998 |
| WO | WO-98/31700 | 7/1998 |
| WO | WO-98/33001 | 7/1998 |
| WO | WO-98/34120 | 8/1998 |
| WO | WO-98/37186 | 8/1998 |
| WO | WO-98/41869 | 9/1998 |
| WO | WO-98/52691 | 11/1998 |
| WO | WO-98/58085 | 12/1998 |
| WO | WO-99/02671 | 1/1999 |
| WO | WO-99/22858 | 5/1999 |
| WO | WO-99/28020 | 6/1999 |
| WO | WO-99/31019 | 6/1999 |
| WO | WO-99/54730 | 10/1999 |
| WO | WO-99/61888 | 12/1999 |
| WO | WO-00/04139 A1 | 1/2000 |
| WO | WO-00/47322 | 2/2000 |
| WO | WO-00/52455 | 2/2000 |
| WO | WO-00/40712 | 6/2000 |
| WO | WO-00/61275 | 10/2000 |
| WO | WO-00/70080 | 11/2000 |
| WO | WO-00/76673 | 12/2000 |
| WO | WO-01/12327 | 2/2001 |
| WO | WO-01/14589 | 3/2001 |
| WO | WO-01/18244 | 3/2001 |
| WO | WO-01/64332 | 9/2001 |
| WO | WO-01/68257 | 9/2001 |
| WO | WO-01/69289 | 9/2001 |
| WO | WO-01/72431 | 10/2001 |
| WO | WO-01/80283 | 10/2001 |
| WO | WO-02/18949 | 3/2002 |
| WO | WO-02/22869 | 3/2002 |
| WO | WO-02/022869 | 3/2002 |
| WO | WO-02/23163 | 3/2002 |
| WO | WO-02/31203 | 4/2002 |
| WO | WO-02/031203 | 4/2002 |
| WO | WO-02/047665 | 6/2002 |
| WO | WO-02/47665 | 8/2002 |
| WO | WO-02/060275 | 8/2002 |
| WO | WO-02/078845 | 10/2002 |
| WO | WO-02/103011 | 12/2002 |
| WO | WO-02/103363 | 12/2002 |
| WO | WO-03/011443 | 2/2003 |
| WO | WO-03/037302 | 5/2003 |
| WO | WO-03/044187 | 5/2003 |
| WO | WO-03/078659 | 9/2003 |
| WO | WO-03/099843 | 12/2003 |
| WO | WO-2004/002627 | 1/2004 |
| WO | WO-2004/018497 | 3/2004 |
| WO | WO-2004/024917 | 3/2004 |
| WO | WO-2004/038363 | 5/2004 |
| WO | WO-2004/069849 | 8/2004 |
| WO | WO-2004/074504 | 9/2004 |
| WO | WO-2004/083443 | 9/2004 |
| WO | WO-2004/087308 | 10/2004 |
| WO | WO-2004/088314 | 10/2004 |
| WO | WO-2004/091763 | 10/2004 |
| WO | WO-2004/102204 | 11/2004 |

(56) References Cited

FOREIGN PATENT DOCUMENTS

| WO | WO-2004/103565 | | 12/2004 | | |
|---|---|---|---|---|---|
| WO | WO-2005/000970 | | 1/2005 | | |
| WO | WO-2005/002730 | | 1/2005 | | |
| WO | WO-2005/021151 | | 3/2005 | | |
| WO | WO-2005/103106 | | 11/2005 | | |
| WO | WO-2005/118138 | | 12/2005 | | |
| WO | WO-2006/002641 | | 1/2006 | | |
| WO | WO-2006/009657 | | 1/2006 | | |
| WO | WO-2006/027757 | | 3/2006 | | |
| WO | WO-2006/038035 | | 4/2006 | | |
| WO | WO-2006/040551 | | 4/2006 | | |
| WO | WO-2006/040554 | | 4/2006 | | |
| WO | WO-2006/078841 | | 7/2006 | | |
| WO | WO-2006/096571 | | 9/2006 | | |
| WO | WO-2006/101851 | | 9/2006 | | |
| WO | WO-2007/021343 | | 2/2007 | | |
| WO | WO-2007/030501 | | 3/2007 | | |
| WO | WO-2007/081385 | | 7/2007 | | |
| WO | WO-2007/081387 | | 7/2007 | | |
| WO | WO-2007081385 | A2 * | 7/2007 | .......... | B01F 13/0071 |
| WO | WO-2007/089541 | | 8/2007 | | |
| WO | WO-2007/114794 | | 10/2007 | | |
| WO | WO-2007/123744 | | 11/2007 | | |
| WO | WO-2007/133710 | | 11/2007 | | |
| WO | WO-2007/138178 | | 12/2007 | | |
| WO | WO-2008/021123 | | 2/2008 | | |
| WO | WO-2008/063227 | | 5/2008 | | |
| WO | WO-2008/097559 | | 8/2008 | | |
| WO | WO2008097559 | * | 8/2008 | | |
| WO | WO-2008/121342 | | 10/2008 | | |
| WO | WO-2008/130623 | | 10/2008 | | |
| WO | WO-2009/029229 | | 3/2009 | | |
| WO | WO-2010/056728 | | 5/2010 | | |
| WO | WO-2010/040006 | | 8/2010 | | |
| WO | WO-2010/151776 | | 12/2010 | | |
| WO | WO-2011/042564 | | 4/2011 | | |
| WO | WO-2011/079176 | | 6/2011 | | |

OTHER PUBLICATIONS

Advisory Action for U.S. Appl. No. 11/360,845, dated Jun. 14, 2010.
Advisory Action for U.S. Appl. No. 11/698,298 dated May 20, 2011.
Affholter and F. Arnold, Engineering a Revolution, Chemistry in Britain, Apr. 1999, p. 48.
Agrawal and Tang, Site-specific functionalization of oligodeoxynucleotides for non-radioactive labelling, Tetrahedron Letters 31:1543-1546 (1990).
Aharoni et al., High-Throughput screens and selections of enzyme-encoding genes, Curr Opin Chem Biol, 9(2): 210-6 (2005).
Ahn et al., Dielectrophoretic manipulation of drops for high-speed microluidic sorting devices, Applied Phys Lett 88, 024104 (2006).
Allen et al., High throughput fluorescence polarization: a homogeneous alternative to radioligand binding for cell surface receptors J Biomol Screen. 5(2):63-9 (2000).
Altman et al., Solid-state laser using a rhodamine-doped silica gel compound, IEEE Photonics technology letters 3(3):189-190 (1991).
Amstutz, P. et al., in vitro display technologies: novel developments and applications. Curr Opin Biotechnol, 12, 400-405 (2001).
Anarbaev et al., Klenow fragment and DNA polymerase alpha-primase fromserva calf thymus in water-in-oil microemulsions, Biochim Biophy Acta 1384:315-324 (1998).
Anderson et al., Preparation of a cell-free protein-synthesizing system from wheat germ, Methods Enzymol 101:635-44 (1983).
Anderson, J.E., Restriction endonucleases and modification methylases, Curr. Op. Struct. Biol., 3:24-30 (1993).
Ando, S. et al., PLGA microspheres containing plasmid DNA: preservation of supercoiled DNA via cryopreparation and carbohydrate stabilization, J Pharm Sci, 88(1):126-130 (1999).
Angell et al., Silicon micromechanical devices, Scientific American 248:44-55 (1983).

Anhuf et al., Determination of SMN1 and SMN2 copy number using TaqMan technology, Hum Mutat 22(1):74-78 (2003).
Anna et al., Formation of dispersions using flow focusing in microchannels, Applied Physics Letters,82(3): 364-366 (2003).
Arkin, M.R. et al., Probing the importance of second sphere residues in an esterolytic antibody by phage display, J Mol Biol 284(4):1083-94 (1998).
Armstrong et al., Multiple-Component Condensation Strategies for Combinatorial Library Synthesis, Acc. Chem. Res. 29(3):123-131 (1996).
Ashkin and Dziedzic, Optical trapping and manipulation of viruses and bacteria, Science 235(4795):1517-20 (1987).
Ashkin et al., Optical trapping and manipulation of single cells using infrared laser beams, Nature 330:769-771 (1987).
Atwell, S. & Wells, J.A., Selection for Improved Subtiligases by Phage Display, PNAS 96: 9497-9502(1999).
Auroux, Pierre-Alain et al., Micro Total Analysis Systems. 2. Analytical Standard Operations and Applications, Analytical Chemistry, vol. 74, No. 12, 2002, pp. 2637-2652.
Baccarani et al., *Escherichia coli* dihydrofolate reductase: isolation and characterization of two isozymes, Biochemistry 16(16):3566-72 (1977).
Baez et al., Glutathione transferases catalyse the detoxication of oxidized metabolites (o-quinones) of catecholamines and may serve as an antioxidant system preventing degenerative cellular processes, Biochem. J 324:25-28 (1997).
Bagwe et al, Improved drug delivery using microemulsions: rationale, recent progress, and new horizons, Crit Rev Ther Drug Carr Sys 18(1):77-140 (2001).
Baker, M., Clever PCR: more genotyping, smaller volumes, Nature Methods 7:351-356 (2010).
Ball and Schwartz, CMATRIX: software for physiologically based pharmacokinetic modeling using a symbolic matrix representation system, Comput Biol Med 24(4):269-76 (1994).
Ballantyne and Nixon, Selective Area Metallization by Electron-Beam Controlled Direct Metallic Deposition, J. Vac. Sci. Technol. 10:1094 (1973).
Barany F., The ligase chain reaction in a PCR World, PCR Methods and Applications 1(1):5-16 (1991).
Barony, F. Genetic disease detection and DNA amplification using cloned thermostable ligase, PNAS 88(1): 189-93 (1991).
Baret et al., Fluorescence-activated droplet sorting (FADS): efficient microfluidic cell sorting based on enzymatic activity, Lab on a Chip 9:1850-1858 (2009).
Baret et al., Kinetic aspects of emulsion stabilization by surfactants: a microfluidic analysis, Langmuir 25:6088-6093 (2009).
Bass et al., Hormone Phage: An Enrichment Method for Variant Proteins With Altered Binding Properties, Proteins 8:309-314(1990).
Bauer, J., Advances in cell separation: recent developments in counterflow centrifugal elutriation and continuous flow cell separation, J Chromatography, 722:55-69 (1999).
Beebe et al., Functional hydrogel structures for autonomous flow control inside microfluidic channels, Nature 404:588-590 (2000).
Beer et al., On-Chip, Real-Time, Single-Copy Polymerase Chain Reaction in Picoliter Droplets, Anal. Chem., 2007, v. 79, pp. 847-8475.
Bein, Thomas, Efficient Assays for Combinatorial methods for the Discovery of Catalysts, Agnew. Chem. Int. Ed. 38:3, 323-26 (1999).
Benichou et al., Double Emulsions Stabilized by New Molecular Recognition Hybrids of Natural Polymers, Polym. Adv. Tehcnol 13:1019-1031 (2002).
Benner, S.A., Expanding the genetic lexicon: incorporating non-standard amino acids into proteins by ribosome-based synthesis, Trends Biotechnol 12:158-63 (1994).
Benning, M.M. et al., The binding of substrate analogs to phosphotriesterase. J Biol Chem, 275, 30556-30560 (2000).
Berman et al., An agarose gel electrophoresis assay for the detection of DNA-binding activities in yeast cell extracts, Methods Enzymol 155:528-37 (1987).
Bernath et al, In Vitro Compartmentalization by Double Emulsions: Sorting and Gene Enrichment by Fluorescence Activated Cell Sorting, Anal. Biochem 325:151-157 (2004).

(56) References Cited

OTHER PUBLICATIONS

Bernath et al., Directed evolution of protein inhibitors of DNA-nucleases by in vitro compartmentalization (IVC) and nano-droplet delivery, J. Mol. Biol 345(5):1015-26 (2005).
Betlach, L. et al., A restriction endonuclease analysis of the bacterial plasmid controlling the EcoRI restriction and modification of DNA. Federation Proceedings, 35, 2037-2043 (1976).
Bibette et al., Emulsions: basic principles, Rep. Prog. Phys. 62: 969-1033 (1999).
Bico, Jose et al., Rise of Liquids and Bubbles in Angular Capillary Tubes, Journal of Colloid and Interface Science, 247:162-166 (2002).
Bico, Jose et al., Self-Propelling Slugs, J. Fluid Mech., 467:101-127 (2002).
Blattner and Dahlberg, RNA synthesis startpoints in bacteriophage lambda: are the promoter and operator transcribed, Nature New Biol 237(77):227-32 (1972).
Boder et al., Yeast surface display for screening combinatorial polypeptide libraries, Nat Biotechnol 15(6):553-7 (1997).
Bougueleret, L. et al., Characterization of the gene coding for the EcoRV restriction and modification system of *Escherichia coli*, Nucleic Acids Res, 12(8):3659-76 (1984).
Boyum, A., Separation of leukocytes from blood and bone marrow. Introduction, Scand J Clin Lab Invest Suppl 97:7 (1968).
Branebjerg et al., Fast mixing by lamination, MEMS Proceedings 9th Ann WO rkshop, San Diego, Feb. 11-15, 1996, 9:441-446 (1996).
Braslaysky et al., Sequence information can be obtained from single DNA molecules, PNAS 100(7):3960-3964 (2003).
Bringer et al., Microfluidic Systems for Chemical Kinetics That Rely on Chaotic Mixing in Droplets, Philos Transact A Math Phys Eng Sci 362:1-18 (2004).
Brody et al., A self-assembled microlensing rotational probe, Applied Physics Letters, 74:144-46 (1999).
Brown et al., Chemical synthesis and cloning of a tyrosine tRNA gene, Methods Enzymol 68:109-151 (1979).
Bru, R. et al., Catalytic activity of elastase in reverse micelles, Biochem Mol Bio Int, 31(4):685-92 (1993).
Bru, R. et al., Product inhibition of alpha-chymotrypsin in reverse micelles. Eur J Biochem 199(1): 95-103 (1991).
Brummelkamp et al., A system for stable expression of short interfering RNAs in mammalian cells, Science 296(5567):550-3 (2002).
Buckpitt et al., Hepatic and pulmonary microsomal metabolism of naphthalene to glutathione adducts: factors affecting the relative rates of conjugate formation, J. Pharmacol. Exp. Ther. 231:291-300 (1984).
Buican et al., Automated single-cell manipulation and sorting by light trapping, Applied Optics 26(24):5311-5316 (1987).
Burbaum, J., Miniaturization technologies in HTS: how fast, how small, how soon Drug Discov Today 3:313-322 (1998).
Burns et al., Microfabricated structures for integrated DNA analysis, Proc. Natl. Acad. Sci. USA, 93:5556-5561(1996).
Burns, J.R. et al., The Intensification of Rapid Reactions in Multiphase Systems Using Slug Flow in Capillaries, Lab on a Chip, 1:10-15 (2001).
Burns, Mark et al., An Integrated Nanoliter DNA Analysis Device, Science, 282:484-487(1998).
Byrnes, P.J. et al., Sensitive fluorogenic substrates for the detection of trypsin-like proteases and pancreatic elastase, Anal Biochem, 126:447 (1982).
Cahill et al., Polymerase chain reaction and Q beta replicase amplification, Clin Chem 37(9):1482-5 (1991).
Caldwell, S.R. et al., Limits of diffusion in the hydrolysis of substrates by the phosphodiesterase from Pseudomonas diminuta, Biochemistry, 30: 7438-7444 (1991).
Calvert, P., Inkjet printing for materials and devices, Chem Mater 13: 3299-3305 (2001).
Caruthers, Gene synthesis machines: DNA chemistry and its uses, Science 230:281-285 (1985).

Chakrabarti, A.C. et al., Production of Rna by a polymerase protein encapsulated within phospholipid vesicles, J Mol Evol, 39(6):555-9 (1994).
Chamberlain and Ring, Characterization of T7-specific ribonucleic acid polymerase. 1. General properties of the enzymatic reaction and the template specificity of the enzyme, J Biol Chem 248:2235-44 (1973).
Chan, Emory M. et al., Size-Controlled Growth of CdSe Nanocrystals in Microfluidic Reactors, Nano Letters, 3(2):199-201(2003).
Chang and Su, Controlled double emulsification utilizing 3D PDMS microchannels, Journal of Micromechanics and Microengineering 18:1-8 (2008).
Chang, T.M., Recycling of NAD(P) by multienzyme systems immobilized by microencapsulation in artifical cells, Methods Enzymol, 136(67):67-82 (1987).
Chao et al., Control of Concentration and Volume Gradients in Microfluidic Droplet Arrays for Protein Crystallization Screening, 26th Annual International Conference of the IEEE Engineering in Medicine and Biology Society, San Francisco, California Sep. 1-5, (2004).
Chao et al., Droplet Arrays in Microfluidic Channels for Combinatorial Screening Assays, Hilton Head 2004: A Solid State Sensor, Actuator and Microsystems Workshop, Hilton Head Island, South Carolina, Jun. 6-10, 2004.
Chapman et al., In vitro selection of catalytic RNAs, Curr. op. Struct. Biol., 4:618-22 (1994).
Chayen, Crystallization with oils: a new dimension in macromolecular crystal growth Journal of Crystal Growth,196:434-441(1999).
Chen et al., Capturing a Photoexcited Molecular Structure Through Time-Domain X-ray Absorption Fine Structure, Science 292(5515):262-264 (2001).
Chen et al., Microfluidic Switch for Embryo and Cell Sorting the 12th International Conference on Solid State Sensors, Actuators, and Microsystems, Boston, MA Jun. 8-12, 2003 Transducers, 1: 659-662 (2003).
Chen-Goodspeed et al., Structural Determinants of the substrate and stereochemical specificity of phosphotriesterase, Biochemistry, 40(5):1325-31 (2001).
Chen-Goodspeed, M. et al., Enhancement, relaxation, and reversal of the stereoselectivity for phosphotriesterase by rational evolution of active site residues, Biochemistry, 40: 1332-1339 (2001b).
Cheng, Z.,et al, Electro flow focusing in microfluidic devices, Microfluidics Poster, presented at DBAS, Frontiers in Nanoscience, presented Apr. 10, 2003.
Chetverin and Spirin, Replicable RNA vectors: prospects for cell-free gene amplification, expression, and cloning, Prog Nucleic Acid Res Mol Biol, 51:225-70 (1995).
Chiang, C.M. et al., Expression and purification of general transcription factors by FLAG epitope-tagging and peptide elution, Pept Res, 6: 62-64 (1993).
Chiba et al., Controlled protein delivery from biodegradable tyrosino-containing poly(anhydride-co-imide) microspheres, Biomaterials, 18(13): 893-901 (1997).
Chiou et al., A closed-cylce capillary polymerase chain reaction machine, Analytical Chemistry, American Chemical Society, 73:2018-21 (2001).
Chiu et al., Chemical transformations in individual ultrasmall biomimetic containers, Science, 283: 1892-1895 (1999).
Chou et al., A mirofabricated device for sizing and sorting DNA molecules 96:11-13(1998).
Clackson, T. et al., In vitro selection from protein and peptide libraries, Trends Biotechnol, 12:173-84 (1994).
Clausell-Tormos et al., Droplet-based microfluidic platforms for the encapsulation and screening of Mammalian cells and multicellular organisms, Chem Biol 15(5):427-437 (2008).
Cohen, S. et al., Controlled delivery systems for proteins based on poly(lactic/glycolic acid) microspheres, Pharm Res, 8(6):713-720 (1991).
Collins et al., Optimization of Shear Driven Droplet Generation in a Microluidic Device, ASME International Mechanical Engineering Congress and R&D Expo, Washington (2003).
Collins, J. et al., Microfluidic flow transducer based on the measurements of electrical admittance, Lab on a Chip, 4:7-10 (2004).

(56) References Cited

OTHER PUBLICATIONS

Compton, J., Nucleic acid sequence-based amplification, Nature, 350(6313):91-2 (1991).
Cormack, B.P. et al., FACS-optimized mutants of the green fluorescent protein (GFP), Gene 173(1):33-38 (1996).
Cortesi et al., Production of lipospheres as carriers for bioactive compounds, Biomateials, 23(11): 2283-2294 (2002).
Courrier et al., Reverse water-in-fluorocarbon emulsions and microemulsions obtained with a fluorinated surfactant, Colloids and Surfaces A: Physicochem. Eng. Aspects 244:141-148 (2004).
Craig, D. et al., Fluorescence-based enzymatic assay by capillary electrophoresis laser-induced fluoresence detection for the determinination of a few alpha-galactosidase molecules, Anal. Biochem. 226: 147 (1995).
Creagh, A.L. et al., Structural and catalytic properties of enzymes in reverse micelles, Enzyme Microb Technol 15(5): 383-92 (1993).
Crosland-Taylor, A Device for Counting Small Particles suspended in a Fluid through a Tube, Nature 171:37-38 (1953).
Crowley, J. M., Electrical breakdown of bimolecular lipid membranes as an electromechanical instability, Biophys J. 13(7):711-724 (1973).
Cull, M.G. et al., Screening for receptor ligands using large libraries of peptides linked to the C terminus of the lac repressor, PNAS 89:1865-9 (1992).
Curran, D.P., Strategy-level separations in organic synthesis: from planning to practice. Angew Chem Int Ed, 37: 1174-11-96 (1998).
Czarnik, A.W., Encoding methods for combinatorial chemistry, Curr Opin Chem Biol 1:60-66 (1997).
Dankwardt et al., Combinatorial synthesis of small-molecule libraries using 3-amino-5-hydroxybenzoic acid, 1:113-120 (1995).
Davis, J.A. et al., Deterministic hydrodynamics: Taking blood apart, PNAS 103:14779-14784 (2006).
Davis, S.S. et al., Multiple emulsions as targetable delivery systems, Methods in Enzymology, 149: 51-64 (1987).
De Gans, B.J. et al., Inkjet printing of polymers: state of the art and future developments, Advanced materials, 16: 203-213 (2004).
De-Bashan, L. E. et al., Removal of ammonium and phosphorus ions from synthetic wastewater by the microalgae *Chlorella vulgaris* coimmobilized in alginate beads with the microalgae growth-promoting bacterium *Azospirillum brasilense*, Water Research 36:2941-2948 (2002).
Delagrave, S. et al., Red-shifted excitation mutants of the green fluorescent protein, Biotechnology 13(2):151-4 (1995).
DelRaso, In vitro methodologies for enhanced toxicity testing, Toxicol. Lett. 68:91-99 (1993).
Demartis et al., A strategy for the isolation of catalytic activities from repertoires of enzymes displayed on phage, J. Mol. Biol 286:617-633 (1999).
Dickinson, E., Emulsions and droplet size control, Wedlock, D.J., Ed., in Controlled Particle Droplet and Bubble Formulation, ButterWO rth-Heine-mann, 191-257 (1994).
DiMatteo, et al., Genetic conversion of an SMN2 gene to SMN1: A novel approach to the treatment of spinal muscular atrophy, Exp Cell Res. 314(4):878-886 (2008).
Dinsmore et al., Colioidosomes: Selectively Permeable Capsules Composed of Colloidal Particles, Science 298(5595):1006-1009. (2002).
Dittrich et al., A new embedded process for compartmentalized cell-free protein expression and on-line detection in microfluidic devices, Chembiochem 6(5):811-814 (2005).
Doi et al., In vitro selection of restriction endonucleases by in vitro compartmentilization, Nucleic Acids Res, 32(12): e95 (2004).
Doi, N. and Yanagawa, H. STABLE: protein-DNA fusion system for screening of combinatorial protein libraries in vitro, FEBS Lett., 457: 227-230 (1999).
Doman, T.N. et al., Molecular docking and high-throughput screening for novel inhibitors of protein tyrosine phosphatase-1B, J Med Chem, 45: 2213-2221 (2002).
Domling A., Recent advances in isocyanide-based multicomponent chemistry, Curr Opin Chem Biol, 6(3):306-13 (2002).
Domling and Ugi, Multicomponent Reactions with Isocyanides, Angew Chem Int Ed 39(18):3168-3210 (2000).
Dove et al., In Brief, Nature Biotechnology 20:1213 (2002).
Dower et al., High efficiency transformation of *E. coli* by high voltage electroporation, Nucleic Acids Res 16:6127-6145 (1988).
Dressman et al., Transforming single DNA molecules into fluorescent magnetic particles for detection and enumeration of genetic variations, PNAS 100:8817-22 (2003).
Dreyfus et al., Ordered and disordered patterns in two phase flows in microchannels, Phys Rev Lett 90(14):144505-1-144505-4 (2003).
Drmanac et al., Sequencing by hybridization: towards an automated sequencing of one million M13 clones arrayed on membranes, Elctrophoresis 13:566-573 (1992).
Dubertret et al., In vivo imaging of quantum dots encapsulated in phospholipid micelles, Science, 298: 1759-1762 (2002).
Duffy et al., Rapid Protyping of Microfluidic Systems and Polydimethylsiloxane, Anal Chem 70:474-480 (1998).
Duggleby, R. G. Enzyme Kinetics and Mechanisms, Pt D. Academic Press 249:61-90 (1995).
Dumas, D.P., Purification and properties of the phosphotriesterase from Psuedomonas diminuta, J Biol Chem 264: 19659-19665 (1989).
Eckert and Kunkel, DNA polymerase fidelity and the polymerase chain reaction, Genome Res 1:17-24 (1991).
Edd et al., Controlled encapsulation of single-cells into monodisperse picolitre drops, Lab Chip 8(8):1262-1264 (2008).
Edel, Joshua B. et al., Microfluidic Routes to the Controlled Production of Nanopaticles, Chemical Communications, 1136-1137 (2002).
Edris et al., Encapsulation of orange oil in a spray dried double emulsion, Nahrung/Food, 45(2):133-137 (2001).
Effenhauser et al., Glass chips for high-speed capillary electrophoresis separations with submicrometer plate heights, Anal Chem 65:2637-2642 (1993).
Eggers, Jens et al., Coalescence of Liquid Drops, J. Fluid Mech.,401 : 293-310 (1999).
Ehrig, T. et al., Green-fluorescent protein mutants with altered fluorescence excitation spectra, Febs Lett, 367(2):163-66 (1995).
Eigen et al., hypercycles and compartments: compartments assists— but does not replace—hypercyclic organization of early genetic information, J Theor Biol, 85:407-11 (1980).
Eigen et al., The hypercycle: coupling of RNA and protein biosynthesis in the infection cycle of an RNA bacteriophage, Biochemistry, 30:11005-18 (1991).
Eigen, Wie entsteht information Prinzipien der selbstorganisation in der biologie, Berichte der punsen-gesellschaft fur physikalische chemi, 80:1059-81 (1976).
Ellington and Szostak, in vitro selection of RNA molecules that bind specific ligands, Nature, 346:818-822 (1990).
Ellman et al., Biosynthetic method for introducing unnatural amino acids site-specifically into proteins, Methods Enzymol, 202:301-36 (1991).
Endo et al. Kinetic determination of trace cobalt by visual autocatalytic indication, Talanta 47:349-353 (1998).
Endo et al., Autocatalytic decomposition of cobalt complexes as an indicator system for the determination of trace amounts of cobalt and effectors, Analyst 121:391-394 (1996).
Eow et al., Electrocoalesce-separators for the separation of aqueous drops from a flowing dielectric viscous liquid, Separation and Purification Tech 29:63-77 (2002).
Eow et al., Electrostatic enhancement of coalescence of water droplets in oil: a review of the technology, Chemical Engineeing Journal 85:357-368 (2002).
Eow et al., Motion, deformation and break-up of aqueous drops in oils under high electric field strengths, Chemical Eng Proc 42:259-272 (2003).
Eow et al., The behavior of a liquid-liquid interface and drop-interface coalescence under the influence of an electric field, Colloids and Surfaces A: Physiochem. Eng. Aspects 215:101-123 (2003).
Eow, et al. Electrostatic and hydrodynamic separation of aqueous drops in a flowing viscous oil, Chemical Eng Proc 41:649-657 (2002).

(56) References Cited

OTHER PUBLICATIONS

Extended European Search Report for EP 10181911.8 dated Jun. 1, 2011 (7 pages).
Extended European Search Report for EP 10184514.7 dated Dec. 20, 2010 (5 pages).
Faca et al., A mouse to human search for plasma proteome changes associated with pancreatic tumor development, PLoS Med 5(6):e123 (2008).
Fahy et al., Self-sustained sequence replication (3SR): an isothermal transcription-based amplification system alternative to PCR, PCR Methods Appl 1:25-33 (1991).
Fan and Harrison, Micromachining of capillary electrophoresis injectors and separators on glass chips and evaluation of flow at capillary intersections, Anal Chem 66:177-184 (1994).
Fastrez, J., In vivo versus in vitro screening or selection for catalytic activity in enzymes and abzymes, Mol Biotechnol 7(1):37-55 (1997).
Fettinger et al., Stacked modules for micro flow systems in chemical analysis: concept and studies using an enlarged model, Sens Actuat B. 17:19-25 (1993).
Fiedler et al., Dielectrophoretic sorting of particles and cells in a microsystem, Anal Chem 70(9):1909-1915 (1998).
Field, J. et al., Purification of a RAS-responsive adenylyl cyclase complex from *Saccharomyces cervisiae* by use of an epitope addition method. Mol Cell Biol, 8: 2159-2165 (1988).
Fields, S. and Song, O., A novel genetic system to detect protein-protein interactions, Nature 340(6230): 245-6 (1989).
Filella et al., TAG-72, CA 19.9 and CEA as tumor markers in gastric cancer, Acta Oncol. 33(7):747-751 (1994).
Finch, C.A., Encapsulation and controlled release, Spec Publ R Soc Chem, 138:35 (1993).
Finch, C.A., Industrial Microencapsulation: Polymers for Microcapsule Walls, 1-12 in Encapsulation and Controlled Release, Woodhead Publishing (1993).
Fire & Xu, Rolling replication of short DNA circles, PNAS 92(10):4641-5 (1995).
Firestine, S.M. et al., Using an AraC-based three hybrid system to detect biocatalysts in vivo, Nat Biotechnol 18: 544-547 (2000).
Fisch et al., A strategy of exon shuffling for making large peptide repertoires displayed on filamentous bacteriophage, PNAS 93:7761-6 (1996).
Fisher et al., Cell Encapsulation on a Microfluidic Platform, The Eighth International Conference on Miniaturised Systems for Chemistry and Life Scieces, MicroTAS 2004, Sep. 26-30, Malmo, Sweden.
Fletcher et al., Micro reactors: principles and applications in organic synthesis, Tetrahedron 58:4735-4757 (2002).
Fluri et al., Integrated capillary electrophoresis devices with an efficient postcolumn reactor in planar quartz and glass chips, Anal Chem 68:4285-4290 (1996).
Fornusek, L. et al., Polymeric microspheres as diagnostic tools for cell surface marker tracing, Crit Rev Ther Drug Carrier Syst, 2:137-74 (1986).
Fowler, Enhancement of Mixing by Droplet-Based Microfluidics, Int Conf MEMS 97-100 (2002).
Freese, E., The specific mutagenic effect of base analogues on Phage T4, J Mol Biol, 1: 87 (1959).
Frenz et al., Reliable microfluidic on-chip incubation of droplets in delay-lines, Lab on a Chip 9:1344-1348 (2008).
Fu et al., A microfabricated fluorescence-activated cell sorter, Nature Biotechnology, 17(11):1109-1111 (1999).
Fu et al., An Integrated Microfabricated Cell Sorter, Anal. Chem., 74: 2451-2457 (2002).
Fulton et al., Advanced multiplexed analysis with the FlowMetrix system, Clin Chem 43:1749-1756 (1997).
Fulwyler, Electronic Separation of Biological Cells by Volume, Science 150(3698):910-911 (1965).
Gallarate et al., On the stability of ascorbic acid in emulsified systems for topical and cosmetic use, Int J Pharm 188(2):233-241 (1999).

Ganan-Calvo, A.M., Perfectly Monodisperse Microbubbling by Capillary Flow Focusing, Phys Rev Lett 87(27): 274501-1-4 (2001).
Ganan-Calvo, Generation of Steady Liquid Microthreads and Micron-Sized Monodisperse Sprays and Gas Streams, Phys Rev Lett 80(2):285-288 (1998).
Garcia-Ruiz et al. A super-saturation wave of protein crystallization, J. Crystal Growth, 232:149-155(2001).
Garcia-Ruiz et al., Investigation on protein crystal growth by the gel acupuncture method{, Acta, Cryst., 1994, D50, 99. pp. 484-490.
Garstecki, et al., Formation of monodisperse bubbles in a microfluidic flow-focusing device, Appl Phys Lett 85(13):2649-2651 (2004).
Gasperlin et al., The structure elucidation of semisolid w/o emulsion systems containing silicone surfactant, Intl J Pharm, 107:51-6 (1994).
Gasperlin et al., Viscosity prediction of lipophillic semisolid emulsion systems by neural network modeling, Intl J Pharm, 196:37-50 (2000).
Georgiou et al., Display of heterologous proteins on the surface of microorganisms: from the screenign of combinatiorial libraires to live recombinant vaccines. Nat Biotechnol 15(1), 29-34 (1997).
Georgiou, G., Analysis of large libraries of protein mutants using flow cytometry, Adv Protein Chem, 55: 293-315 (2000).
Gerdts et al., A Synthetic Reaction NetWork: Chemical Amplification Using Nonequilibrium Autocatalytic Reactions Coupled in Time, J. Am. Chem. Soc 126:6327-6331 (2004).
Ghadessy et al., Directed Evolution of Polymerase Function by Compartmentalized Self-Replication, PNSAS 98(8): 4552-4557 (2001).
Gibbs et al., Detection of single DNA base differences by competitive oligonucleotide priming, Nucleic Acids Res. 17(7): 2437-48 (1989).
Gilliland, G., Analysis of cytokine mRNA and DNA: Detection and quantitation by competitive polymerase chain reaction, PNAS, 87(7):2725-9 (1990).
Giusti et al., Synthesis and characterization of 5' fluorescent dye labeled oligonucleotides, Genome Res 2:223-227 (1993).
Gold et al., Diversity of Oligonucleotide Functions Annu Rev Biochem, 64: 763-97 (1995).
Goodall, J. L. et al., Operation of Mixed-Culture Immobilized Cell Reactors for the Metabolism of Meta- and Para-Nitrobenzoate by *Comamonas* Sp. JS46 and *Comamonas* Sp. JS47, Biotechnology and Bioengineering, 59 (1): 21-27 (1998).
Gordon and Balasubramanian, Solid phase synthesis—designer linkers for combinatorial chemistry: a review, J. Chem. Technol. Biotechnol., 74(9):835-851 (1999).
Grasland-Mongrain et al., Droplet coalescence in microfluidic devices, 30 pages (Jul. 2003) From internet: http://www.eleves.ens.fr/home/grasland/rapports/stage4.pdf.
Green, R. and Szostak, J.W., Selection of a Ribozyme That Functions as a Superior Template in a Self Copying Reaction, Science, 258: 1910-5 (1992).
Gregoriadis, G., Enzyme entrapment in liposomes, Methods Enzymol 44:218-227 (1976).
Griffiths et al., Directed evolution of an extremely fast phosphotriesterase by in vitro compartmentalization, EMBO J, 22:24-35 (2003).
Griffiths et al., Isolation of high affinity human antibodies directly from large synthetic repertoires, Embo J 13(14):3245-60 (1994).
Griffiths et al., Man-made enzymes-from design to in vitro compartmentalisation, Curr Opin Biotechnol 11:338-353 (2000).
Griffiths, A., and Tawfik, D., Miniaturising the laboratory in emulsion droplets, Trend Biotech 24(9):395-402 (2006).
Griffiths, A.D. et al., Strategies for selection of antibodies by phage display, Curr Opin Biotechnol, 9:102-8 (1998).
Guatelli, J.C. et al., Isothermal, in vitro amplification of nucleic acids by a multienzyme reaction modeled after retroviral replication, PNAS, 87(5):1874-8 (1990).
Guixe et al., Ligand-Induced Conformational Transitions in *Escherichia coli* Phosphofructokinase 2: Evidence for an Allosteric Site for MgATP2n, Biochem., 37: 13269-12375 (1998).
Gupta, K.C., et al., A general method for the synthesis of 3'-sulfhydryl and phosphate group containing oligonucleotides, Nucl Acids Res 19 (11): 3019-3026 (1991).

(56) References Cited

OTHER PUBLICATIONS

Haber et al., Activity and spectroscopic properties of bovine liver catalase in sodium bis(2-ethylhexyl) sulfosuccinate/isooctane reverse micelles, Eur J Biochem 217(2): 567-73 (1993).
Habig and Jakoby, Assays for differentiation of glutathione S-transferases, Methods in Enzymology, 77: 398-405 (1981).
Hadd et al., Microchip Device for Performing Enzyme Assays, Anal. Chem 69(17): 3407-3412 (1997).
Haddad et al., A methodology for solving physiologically based pharmacokinetic models without the use of simulation software, Toxicol Lett. 85(2): 113-26 (1996).
Hagar and Spitzer, The effect of endotoxemia on concanavalin A induced alterations in cytoplasmic free calcium in rat spleen cells as determined with Fluo-3, Cell Calcium 13:123-130 (1992).
Hai et al., Investigation on the release of fluorescent markers from the w/o/w emulsions by fluorescence-activated cell sorter, J Control Release, 96(3): 393-402 (2004).
Haies et al., Morphometric study of rat lung cells. I. Numerical and dimensional characteristics of parenchymal cell population, Am. Rev. Respir. Dis. 123:533-54 (1981).
Hall, Experimental evolution of Ebg enzyme provides clues about the evolution of catalysis and to evolutionary potential, FEMS Microbiol Lett, 174(1):1-8 (1999).
Hall, The EBG system of *E. coli*: origin and evolution of a novel beta-galactosidase for the metabolism of lactose, Genetica 118(2-3):143-56 (2003).
Han et al., Quantum-dot-tagged Microbeads for Multiplexed Optical Coding of Biomolecules, Nat Biotech 19(7): 631-635 (2001).
Handen, J.S., High-throughput screening—challenges for the future, Drug Discov World, 47-50 (2002).
Handique, K. et al., On-Chip Thermopneumatic Pressure for Discrete Drop Pumping, Analytical Chemistry, 73:1831-1838 (2001).
Hanes et al., Degradation of porous poly(anhydide-co-imide) microspheres and implication for controlled macromolecule delivery, Biomaterials, 19(1-3): 163-172(1998).
Hanes et al., In vitro selection and evolution of functional proteins by using ribosome display, PNAS 94:4937-42 (1997).
Hansen et al., A robust and scalable microfluidic metering method that allows protein crystal growth by free interface diffusion, PNAS 99(26):16531-16536 (2002).
Harada et al., Monoclonal antibody G6K12 specific for membrane-associated differentiation marker of human stratified squamous epithelia and squamous cell carcinoma, J. Oral Pathol. Med 22(4):145-152 (1993).
Harder, K.W. et al., Characterization and kinetic analysis of the intracellular domain of human protein tyrosine phosphatase beta (HPTP beta) using synthetic phosphopeptides, Biochem J 298 (Pt 2): 395-401 (1994).
Harries et al., A Numerical Model for Segmented Flow in a Microreactor, Int J of Heat and Mass Transfer, 46:3313-3322 (2006).
Harris et al., Single-molecule DNA sequencing of a viral genome, Science 320(5872):106-109 (2008).
Harrison et al., Micromachining a miniaturized capillary electrophoresis-based chemical analysis system on a chip, Science 261(5123):895-897 (1993).
Hasina et al., Plasminogen activator inhibitor-2: a molecular biomarker for head and neck cancer progression, Cancer Research 63:555-559 (2003).
Haynes Principles of Digital PCR and Measurement IssueOct. 15, 2012.
Hayward et al., Dewetting Instability during the Formation of Polymersomes from BloceCopolymer-Stabilized Double Emulsions, Langmuir, 22(10): 4457-4461 (2006).
He et al., Selective encapsulation of single cells and subcellular organelles into picoliter- and femtoliter-volume droplets, Anal Chem 77(6):1539-1544 (2005).
Heim et al., Engineering Green Fluorescent Protein for Improved Brightness, Longer Wavelengths and Fluorescence Response Energy Transfer, Carr. Biol, 6(2): 178-182 (1996).
Hellman et al., Differential tissue-specific protein markers of vaginal carcinoma, Br J Cancer, 100(8): 1303-131 (2009).
Hergenrother et al., Small-Molecule Microarrays: Covalent Attachment and Screening of Alcohol-Containing Small Molecules on Glass Slides, J. Am. Chem. Soc, 122: 7849-7850 (2000).
Hildebrand et al., Liquid-Liquid Solubility of Perfluoromethylcyclohexane with Benzene, Carbon Tetrachloride, Chlorobenzene, Chloroform and Toluene, J. Am. Chem. Soc, 71:22-25 (1949).
Hjelmfelt et al, Pattern-Recognition in Coupled Chemical Kinetic Systems, Science, 260(5106):335-337 (1993).
Ho, S.N. et al., Site-directed mutageneiss by overlap extension using the polymerase chain reaction, Gene, 77(1):51-9 (1989).
Hoang, Physiologically based pharmacokinetic models: mathematical fundamentals and simulation implementations, Toxicol Lett 79(1-3):99-106 (1995).
Hochuli et al., New metal chelate adsorbent selective for proteins and peptides containing neighbouring histidine residues, J Chromatogr 411: 177-84 (1987).
Holmes et al., Reagents for Combinatorial Organic Synthesis: Development of a New O-Nitrobenzyl Photolabile Linder for Solid Phase Synthesis, J. OrgChem., 60: 2318-2319(1995).
Hong, S.B. et al., Stereochemical constraints on the substrate specificity of phosphodiesterase, Biochemistry, 38: 1159-1165 (1999).
Hoogenboom et al., Multi-subunit proteins on the surface of filamentous phage: methodologies for displaying antibody (Fab) heavy and light chains, Nucl Acids Res., 91: 4133-4137 (1991).
Hoogenboom, H.R., Designing and optimizing library selection strategies for generating high-affinity antibodies, Trends Biotechnol, 15:62-70 (1997).
Hopfinger & Lasheras, Explosive Breakup of a Liquid Jet by a Swirling Coaxial Jet, Physics of Fluids 8(7):1696-1700 (1996).
Hopman et al., Rapid synthesis of biotin-, digoxigenin-, trinitrophenyl-, and fluorochrome-labeled tyramides and their application for In situ hybridization using CARD amplification, J of Histochem and Cytochem, 46(6):771-77 (1998).
Horton et al., Engineering hybrid genes without the use of restriction enzymes: gene splicing by overlap extension, Gene 77(1), 61-8 (1989).
Hosokawa, Kazuo et al., Handling of Picoliter Liquid Samples in a Poly(dimethylsiloxane)-Based Microfluidic Device, Analytical Chemistry, 71(20):4781-4785 (1999).
Hsu et al., Comparison of process parameters for microencapsulation of plasmid DNA in poly(D, L-lactic-co-glycolic acid microspheres, J Drug Target, 7:313-23 (1999).
Huang L. R. et al., Continuous particle separation through deterministic lateral displacement, Science 304(5673):987-990 (2004).
Huang, Z. et al., A sensitive competitive ELISA for 2,4-dinitrophenol using 3,6-fluoresein diphosphate as a fluorogenic substrate, J Immunol Meth, 149:261 (1992).
Huang, Z.J., Kinetic assay of fluorescein mono-beta-D-galactosidase hydrolysis by beta-galactosidase: a front-face measurement for strongly absorbing fluorogenic substrates, Biochemistry, 30:8530-4 (1991).
Hubert et al. Data Concordance from a Comparison between Filter Binding and Fluorescence Polarization Assay Formats for Identification of RUOCK-II Inhibitors, J biomol Screen 8(4):399-409 (2003).
Huebner, A. et al., Quantitative detection of protein expression in single cells using droplet microfluidics, Chem Com 12:1218-1220 (2007).
Hung et al., Optimization of Droplet Generation by controlling PDMS Surface Hydrophobicity, 2004 ASME International Mechanical Engineering Congress and RD&D Expo, Nov. 13-19, Anaheim, CA (2004).
Hung, et al, Controlled Droplet Fusion in Microfluidic Devices, MicroTAS 2004, Sep. 26-30, Malmo, Sweden (2004).
Hutchison et al., Cell-free cloning using Phi29 polymerase, PNAS 102(48):17332-17336 (2005).
Ibrahim, S.F. et al., High-speed cell sorting: fundamentals and recent advances, Curr Opin Biotechnol, 14(1):5-12 (2003).

(56) References Cited

OTHER PUBLICATIONS

Ikeda et al., Bioactivation of tegafur to 5-fluorouracil is catalyzed by cytochrome P-450 2A6 in human liver microsomes in vitro, Clin Cancer Res 6(11):4409-4415 (2000).
Inai et al., Immunohistochemical detection of an enamel protein-related epitope in rat bone at an early stage of osteogenesis, Histochemistry 99(5):335-362 (1993).
International Preliminary Report of Patentability for PCTUS2010061741 dated Sep. 16, 2011(4 pages).
International Preliminary Report on Patentability dated Sep. 20, 2007, for PCT/US2006/007772.
International Search Report and Written Opinion for PCT/US2009/050931 dated Nov. 26, 2009 (3 pages).
International Search Report and Written Opinion for PCTUS1154353 dated Apr. 20, 2012 (34 pages).
International Search Report and Written Opinion for PCTUS12024745 dated May 11, 2012 (21 pages).
International Search Report and Written Opinion for PCTUS1224741 dated Jun. 12, 2012 (12 pages).
International Search Report and Written Opinion for PCTUS125499 dated May 29, 2012 (10 pages).
International Search Report and Written Opinion in PCT/EP2010/065188 dated Jan. 12, 2011 (7 pages).
International Search Report and Written Opinion in PCT/US11/24615 dated Jul. 25, 2011 (37 pages).
International Search Report and Written Opinion in PCT/US2004/010903 dated Dec. 20, 2004 (16 pages).
International Search Report and Written Opinion in PCT/US2006/021286 dated Sep. 14, 2007 (16 pages).
International Search Report and Written Opinion in PCT/US2007/002063 dated Nov. 15, 2007 (20 pages).
International Search Report in PCT/US01/18400 dated Jan. 28, 2005 ( 37 pages).
Ismagilov, Integrated Microfluidic Systems, Angew. Chem. Int. Ed 42:4130-4132 (2003).
Janda, et al, Chemical selection for catalysis in combinatorial antibody libraries, Science, 275:945-948 (1997).
Jang et al., Controllable delivery of non-viral DNA from porous scaffold, J Controlled Release 86(1):157-168 (2003).
Japanese Office Action for JP 2006-509830 dated Jun. 1, 2011 (4 pages).
Jermutus et al., Recent advances in producing and selecting functional proteins by using cell-free translation, Curr Opin Biotechnol 9(5): 534-48 (1998).
Jestin et al., A Method for the Selection of Catalytic Activity Using Phage Display and Proximity Coupling, Agnew. Chem. Int. Ed. Engi. 38(8):1124-1127 (1999).
Jo, et al, Encapsulation of Bovine Serum Albumin in Temperature-Programmed Shell-in-Shell Structures, Macromol. Rapid Comm 24:957-962 (2003).
Joerger et al., Analyte detection with DNA-labeled antibodies and polymerase chain reaction, Clin. Chem. 41(9):1371-7 (1995).
Johannsson et al., Amplification by Second Enzymes, In ELISA and Other Solid Phase Immunoassays, Kemeny et al (ed.), Chapter 4, pp. 85-106 John Wiley (1988).
Johannsson, A., Heterogeneous Enzyme Immunoassays, In Principles and Practice of Immunoassay, pp. 295-325 Stockton Press (1991).
Johnson, T.O. et al., Protein tyrosine phosphatase 1B inhibitors for diabetes, Nature Review Drug Discovery 1, 696-709 (2002).
Jones et al. Glowing jellyfish, luminescence and a molecule called coelenterazine, Trends Biotechnol. 17(12):477-81 (1999).
Jones, L.J. et al., Quenched BODIPY dye-labeled casein substrates for the assay of protease activity by direct fluorescence measurement, Anal Biochem, 251:144 (1997).
Joo et al., Laboratory evolution of peroxide-mediated cytochrome P450 hydroxylaion, Nature 399:670 (1999).
Joos et al., Covalent attachment of hybridizable oligonucleotides to glass supports, Analytical Biochemistry 247:96-101 (1997).
Joyce, G.F., In vitro Evolution of Nucleic Acids, Curr. Opp. Structural Biol, 4: 331-336 (1994).
Kadir and Moore, Haem binding to horse spleen ferritin, Febs Lett, 276: 81-4 (1990).
Kallen, R.G. et al., The mechanism of the condensation of formaldehyde with tetrahydrofolic acid, J. Biol. Chem., 241:5851-63 (1966).
Kambara et al., Optimization of Parameters in a DNA Sequenator Using Fluorescence Detection, Nature Biotechnology 6:816-821 (1988).
Kamensky et al., Spectrophotometer: new instrument for ultrarapid cell analysis, Science 150(3696):630-631 (1965).
Kanouni et al., Preparation of a stable double emulsion (W1/0/W2): role of the interfacial films on the stability of the system, Adv. Collid. Interf. Sci., 99(3): 229-254 (2002).
Katanaev et al., Viral Q beta RNA as a high expression vector for mRNA translation in a cell-free system, Febs Lett, 359:89-92 (1995).
Katsura et al., Indirect micromanipulation of single molecules in water-in-oil emulsion, Electrophoresis, 22:289-93 (2001).
Kawakatsu et al., Regular-sized cell creation in microchannel emulsification by visual microprocessing method, Journal of the American Oil ChemistS Society, 74:317-21 (1997).
Keana J. & Cai, S. X., New reagents for photoaffinity labeling: synthesis and photolysis of functionalized perfluorophenyl azides, J. Org. Chem.55(11):3640-3647 (1990).
Keefe, A.D. et al., Functional proteins from a random-sequence library, Nature, 410: 715-718 (2001).
Keij et al., High-Speed Photodamage Cell Selection Using a Frequency-Doubled Argon Ion Laser, Cytometry, 19(3): 209-216 (1995).
Keij, J.F., et al., High-speed photodamage cell sorting: An evaluation of the ZAPPER prototype, Methods in cell biology, 42: 371-358 (1994).
Kelly et al., Miniaturizing chemistry and biology in microdroplets, Chem Commun 18:1773-1788 (2007).
Kerker, M., Elastic and inelastic light scattering in flow cytometry, Cytometry, 4:1-10 (1983).
Khandjian, UV crosslinking of RNA to nylon membrane enhances hybridization signals, Mol. Bio. Rep. 11: 107-115 (1986).
Kim et al., Comparative study on sustained release of human growth hormone from semi-crystalline poly(L-lactic acid) and amorphous poly(D,L-lactic-co-glycolic acid) microspheres: morphological effect on protein release, Journal of Controlled Release, 98(1):115-125 (2004).
Kim S. et al, Type II quantum dots: CdTe/CdSe (core/shell) and CdSe/ZnTe (core/shell) heterostructures, J. Am Chem Soc. 125:11466-11467 (2003).
Kircher et al., High-throughput DNA sequencing-concepts and limitations, Bioessays 32(6):524-536 (2010).
Kiss et al., High-throughput quantitative polymerase chain reaction in picoliter droplets, Anal. Chem 80:8975-8981 (2008).
Kitagawa et al., Manipulation of a single cell with microcapillary tubing based on its electrophoretic mobility, Electrophoresis 16:1364-1368 (1995).
Klug and Famulok, All you wanted to know about selex, Molecular Biology Reports, 20:97-107 (1994).
Klug and Schwabe, Protein motifs 5. Zinc fingers, FASEB J 9(8):597-604 (1995).
Klug, A., Gene Regulatory Proteins and Their Interaction with DNA, Ann NY Acad Sci, 758:143-60 (1995).
Knaak et al., Development of partition coefficients, Vmax and Km values, and allometric relationships, Toxicol Lett. 79(I-3):87-98 (1995).
Knight, James B., Hydrodynamic Focusing on a Silicon Chip: Mixing Nanoliters in Microseconds, Physical Review Lett 80(17):3863-3866 (1998).
Kojima et al. PCR amplification from single DNA molecules on magnetic beads in emulsion: application for high-throughput screening of transcription factor targets. Nucleic Acids Res. 33:e150 (2005).
Kolb et al., Cotranslational folding of proteins, Biochem Cell Biol, 73:1217-20 (1995).

(56) References Cited

OTHER PUBLICATIONS

Komatsu et al., Roles of cytochromes P450 1A2, 2A6, and 2C8 in 5-fluorouracil formation rom tegafur, an anticancer prodrug, in human liver microsomes. Drug Met. Disp., 28:1457-1463 (2001).

Kopp et al., Chemical amplification: continuous flow PCR on a chip, Science, 280:1046-48 (1998).

Koster et al., Drop-based microfluidic devices for encapsulation of single cells, Lab on a Chip 8:1110-1115 (2008).

Kowalczykowski et al., Biochemistry of homologous recombination in *Escherichia coli*, Microbiol Rev 58(3):401-65 (1994).

Krafft et al., Emulsions and microemulsions with a fluorocarbon phase, Colloid and Interface Science 8(3):251-258 (2003).

Krafft, Fluorocarbons and fluorinated amphiphiles in drug delivery and biomedical research, Adv Rev Drug Disc 47:209-228 (2001).

Krafft et al., Synthesis and preliminary data on the biocompatibility and emulsifying properties of perfluoroalkylated phosphoramidates as injectable surfactants, Eur. J. Med. Chem., 26:545-550 (1991).

Kralj et al., Surfactant-enhanced liquid-liquid extraction in microfluidic channels with inline electric-field enhanced coalescence, Lab Chip 5:531-535 (2005).

Kricka and Wilding, Microchip PCR, Anal Bioanal Chem 377(5):820-825 (2003).

Kricka and Wilding, Micromachining: a new direction for clinical analyzers, Pure and Applied Chemistry 68(10):1831-1836 (1996).

Krumdiek, C.L. et al., Solid-phase synthesis of pteroylpolyglutamates, Methods Enzymol, 524-29 (1980).

Kumar, A. et al., Activity and kinetic characteristics of glutathione reductase in vitro in reverse micellar waterpool, Biochem Biophys Acta, 996(1-2):1-6 (1989).

Lage et al., Whole genome analysis of genetic alterations in small DNA samples using hyperbranched strand displacement amplification and array-CGH. Genome Res. 13: 294-307 (2003).

Lamprecht et al., pH-sensitive microsphere delivery increases oral bioavailability of calcitonin, Journal of Controlled Release, 98(1):1-9(2004).

Lancet, D. et al., Probability model for molecular recognition in biuological receptor repertoirs: significance to the olfactory system, PNAS, 90(8):3715-9 (1993).

Landergren et al., a ligase mediated gene detection technique. Science 241(4869):1077-80 (1988).

Lasheras, et al., Breakup and Atomization of a Round Water Jet by a High Speed Annular Air Jet, J Fluid Mechanics 357:351-379 (1998).

Leary et al., Application of Advanced Cytometric and Molecular Technologies to Minimal Residual Disease Monitoring, Proceedings of SPIE 3913:36-44 (2000).

Lee et al, Investigating the target recognition of DNA cytosine-5 methyltransferase HhaI by library selection using in vitro compartmentalisation (IVC), Nucleic Acids Res 30:4937-4944 (2002).

Lee et al., Circulating flows inside a drop under time-periodic non-uniform electric fields, Phys Fuilds 12(8):1899-1910 (2000).

Lee, et al, Effective Formation of Silicone-in-Fluorocarbon-in-Water Double Emulsions: Studies on Droplet Morphology and Stability, Journal of Dispersion Sci Tech 23(4):491-497(2002).

Lee, et al, Preparation of Silica Paticles Encapsulating Retinol Using O/W/O Multiple Emulsions, Journal of Colloid and Interface Science, 240(1): 83-89 (2001).

Lemof, et al, An AC Magnetohydrodynamic Microfluidic Switch for Micro Total Analysis Systems, Biomedical Microdevices, 5(I):55-60 (2003).

Lesley et al., Use of in vitro protein synthesis from PCR-generated templates to study interaction of *E coli* transcription factors with core RNA polymerase, J Biol Chem 266(4):2632-8 (1991).

Lesley, S.A., Preparation and use of *E. coli* S-30 extracts, Methods Mol Biol, 37:265-78 (1995).

Leung et al., A method for random mutagenesis of a defined DNA segment using a modified polymerase chain reaction. Technique 1:11-15 (1989).

Li and Harrison, Transport, Manipulation, and Reaction of Biological Cells On-Chip Using Electrokinetic Effects, Analytical Chemistry 69(8):1564-1568 (1997).

Li et al., Nanoliter microfluidic hybrid method for simultaneous screening and optimization validated with crystallization of membrane proteins, PNAS 103: 19243-19248 (2006).

Li et al., Single-step procedure for labeling DNA strand breaks with fllourescein-or BODIPY-conjugated deoxynucleotides: detection of apoptosis and bromodeoxyuridine incorporation. Cytometry 20:172-180 (1995).

Liao et al., Isolation of a thermostable enzyme variant by cloning and selection in a thermophile, PNAS 83:576-80 (1986).

Lim et al., Microencapsulated islets as bioartificial endocrine pancreas, Science 210(4472):908-10 (1980).

Link et al, Geometrically Mediated Breakup of Drops in Microfluidic Devices, Phys. Rev. Lett., 92(5): 054503-1 thru 054503-4 (2004).

Link et al., Electric control droplets in microfluidic devices, Angew Chem Int Ed 45:2556-2560 (2006).

Lipinski et al., Experimental and Computational Approaches to Estimate Solubility and Permeability in Drug Discovery and Development Settings ,Adv. Drug Deliv. Rev., 46:3-26 (2001).

Lipkin et al., Biomarkers of increased susceptibility to gastreointestinal cancer: new application to studies of cancer prevention in human subjects, Cancer Research 48:235-245 (1988).

Liu et al., Fabrication and characterization of hydrogel-based microvalves, Mecoelectromech. Syst.11:45-53 (2002).

Liu et al., Passive Mixing in a Three-Dimensional Serpentine MicroChannel, J MEMS 9(2):190-197 (2000).

Lizardi et al., Mutation detection and single-molecule counting using isothermal rolling-circle amplification. Nat Genet 19(3):225-32 (1998).

Loakes and Brown, 5-Nitroindole as a universal base analogue. Nucleic Acids Res 22: 4039-4043 (1994).

Loakes et al., Stability and structure of DNA oligonucleotides containing non-specific base analogues. J. Mol. Biol 270:426-435 (1997).

Loeker et al., Colloids and Surfaces A: Physicochem. Eng. Aspects 214:143-150, (2003).

Lopez-Herrera, et al, Coaxial jets generated from electrified Taylor cones. Scaling laws, Aerosol Science, 34:535-552 (2003).

Lopez-Herrera, et al, One-Dimensional Simulation of the Breakup of Capillary Jets of Conducting Liquids Application to E.H.D. Spraying, Aerosol. Set, 30 (7): 895-912 (1999).

Lopez-Herrera, et al, The electrospraying of viscous and non-viscous semi-insulating liquids. Scalilng laws, Bulletin of the American Physical Society,40 (12):2041(1995).

Lorenceau et al, Generation of Polymerosomes from Double-Emulsions, Langmuir, 21(20): 9183-9186 (2005).

Lorenz et al, Isolation and expression of a cDNA encoding Renilla reniformis luciferase, PNAS 88(10):4438-42 (1991).

Loscertales, et al, Micro/Nano Encapsulation via Electrified Coaxial Liquid Jets, Science, 295(5560): 1695-1698 (2002).

Low N.M. et al., Mimicking somatic hypermutaion: affinity maturation of antibodies displayed on bacteriophage using a bacterila mutator strain. J Mol Biol 260(3), 359-68 (1996).

Lowe, K.C., Perfluorochemical respiratory gas carriers: benefits to cell culture systems, J Fluorine Chem 118:19-26 (2002).

Lowman et al., Selecting high affinity binding proteins by monovalent phage display, Biochemistry 30(45):10832-8 (1991).

Lu et al., Robust fluorescein-doped silica nanoparticles via dense-liquid treatment, Colloids and Surfaces A Physicachemical and Engineering Aspects, 303(3):207-210 (2007).

Luisi et al, Activity and Conformation of Enzymes in Reverse Micellar Solutions, Meth. Enzymol 136:188-216 (1987).

Lund et al., Assesment of methods for covalent binding of nucleic acids to magnetic beads, Dynabeads, and the characteristics of the bound nucleic acids in hybridization reactions, Nucleic Acids Research, Oxford University Press, 16(22) (1998).

Lunderberg et al., Solid-phase technology: magnetic beads to improve nucleic acid detection and analysis, Biotechnology Annual Review, 1:373-401 (1995).

(56) References Cited

OTHER PUBLICATIONS

Lundstrom, et al, Breakthrough in cancer therapy: Encapsulation of drugs and viruses, www.currentdrugdiscovery.com, Nov. 19-23, 2002.
Lyne, P.D., Structure-Based Virtual Screening: An Overview, Drug Discov. Today, 7(20):1047-1055 (2002).
Ma, C. et al., In vitro protein engineering using synthetic tRNA(Ala) with different anticodons, Biochemistry 32(31):7939-45 (1993).
Mackenzie et al., The application of flow microfluorimetry to biomedical research and diagnosis: a review, Dev Biol Stand 64:181-193 (1986).
Mackenzie, IABS Symposium on Reduction of Animal Usage in the Development and Control of Biological Products, London, UK, 1985.
Maclean, D. et al., Glossary of terms used in combinatorial chemistry, Pure Appl. Chem. 71(12):2349-2365 (1999).
Magdassi et al., Multiple Emulsions: HLB Shift Caused by Emulsifier Migration to External Interface, J. Colloid Interface Sci 97:374-379 (1984).
Mahajan et al., Bcl-2 and Bax Interactions in Mitochondria Probed with Green Florescent Protein and Fluorescence Resonance Energy Transfer, Nat. Biotechnol. 16(6): 547-552 (1998).
Manley et al., In vitro transcription: whole cell extract, Methods Enzymol, 101:568-82 (1983).
Manz et al., Micromachining of monocrystalline silicon and glass for chemical analysis systems a lcok into next century's technology or just a fashionable craze, Trends in Analytical Chemistry 10(5):144-149 (1991).
Mao et al., Kinetic behaviour of alpha-chymotrypsin in reverse micelles: a stopped-flow study, Eur J Biochem 208(1):165-70 (1992).
Mao, Q. et al., Substrate effects on the enzymatic activity of alphachymotrypsin in reverse micelles, Biochem Biophys Res Commun, 178(3):1105-12 (1991).
Mardis, E.R., The impact of next-generation sequencing technology on genetics, Trends Genet 24:133-141 (2008).
Margulies, M et al., Genome sequencing in microfabricated high-density picolitre reactors, Nature 437(7057):376-380 (2005).
Marques et al., Porous Flow within Concentric Cylinders, Bull Am Phys Soc Div Fluid Dyn 41:1768 (1996).
Mason, T.J. and Bibette, J. Shear Rupturing of Droplets in Complex Fluids, Langmuir, 13(17):4600-4613 (1997).
Mastrobattista et al., High-throughput screening of enzyme libraries: in vitro evolution of a beta-galactosidase by fluorescence-activated sorting of double emulsions, Chem. Biol. 12(12):1291-1300 (2005).
Masui et ai., Probing of DNA-Binding Sites of Escherichia coli RecA Protein Utilizing 1-anilinonaphthalene-8-Sulfonic Acid, Biochem 37(35):12133-12143 (1998).
Matayoshi, E.D. et al., Novel fluorogenic substrates for assaying retroviral proteases by resonance energy transfer, Science 247:954 (1990).
Mattheakis et al., An in vitro polysome display system for identifying ligands from very large peptide libraries, PNAS 91:9022-6 (1994).
Mayr, L.M., and Fuerst, P., The Future of High-Throughput Screening, JBiomol Screen 13:443-448 (2008).
Mazutis et al., Droplet-Based Microfluidic Systems for High-Throughput Single DNA Molecule Isothermal Amplification and Analysis, Anal Chem 81(12):4813-4821 (2009).
Mazutis et al., Multi-step microfluidic droplet processing: kinetic analysis of an in vitro translated enzyme, Lab Chip 9:2902-2908 (2009).
McCafferty et al., Phage antibodies: filamentous phage displaying antibody variable domains,Nature, 348: 552-4 (1990).
McDonald and Whitesides, Poly(dimethylsiloxane) as a material for fabricating microfluidic devices, Account Chem. Res. 35:491-499 (2002).
McDonald et al. Fabrication of microfluidic systems in poly(dimethylsiloxane), Electrophoresis 21(1):27-40 (2000).
Melton et al., Efficient in vitro synthesis of biologically active RNA and RNA hybridization probes from plasmids containing a bacteriophage SP6 promoter, Nucl. Acids Res. 12(18):7035-7056 (1984).
Mendel, D. et al., Site-Directed Mutagenesis with an Expanded Genetic Code, Annu Rev Biophys Biomol Struct, 24:435-62 (1995).
Menger and Yamada, Enzyme catalysis in water pools, J. Am. Chem. Soc., 101:6731-4 (1979).
Meylan and Howard, Atom/fragment contribution method for estimating octanol-water partition coefficients, J Pharm Sci. 84(1):83-92 (1995).
Miele et al., Autocatalytic replication of a recombinant RNA, J Mol Biol, 171:281-95 (1983).
Minshuil, J. and Stemmer, W.P., Protein evolution by molecular breeding, Curr Opin Chem Biol 3(3): 284-90 (1999).
Miroux and Walker, Over-production of proteins in *Escherichia coli*: mutant hosts that allow synthesis of some membrane proteins and globular proteins at high levels, J of Mol Biol 260(3):289-98 (1996).
Miyawaki et at., Fluorescent Indicators for Ca2+ Based on Green Fluorescent Proteins and Calmodulin, Nature, 388: 882-887 (1997).
Mize et al., Dual-enzyme cascade—an amplified method for the detection of alkaline phosphatase, Anal Biochem 179(2): 229-35 (1989).
Mock et al., A fluorometric assay for the biotin-avidin interaction based on displacement of the fluorescent probe 2-anilinonaphthalene-6-sulfonic acid, Anal Biochem, 151:178-81 (1985).
Moldavan, A., Photo-electric technique for the counting of microscopical cells, Science 80:188-189 (1934).
Montigiani, S. et al., Alanine substitutions in calmodulin-binding peptides result in unexpected affinity enhancement, J Mol Biol, 258:6-13 (1996).
Moore, M.J., Exploration by lamp light, Nature, 374:766-7 (1995).
Moudrianakis and Beer, Base sequence determination in nucelic acids with the electron microscope 3. Chemistry and microscopy of guanine-labeled DNA, PNAS 53:564-71 (1965).
Mueth et al., Origin of stratification in creaming emulsions, Physical Review Letters 77(3):578-581 (1996).
Mulbry, W.W. et al., Parathion hydrolase specified by the Flavobacterium opd gene: relationshio between the gene and protein. J Bacteriol, 171: 6740-6746 (1989).
Mulder et al., Characterization of two human monoclonal antibodies reactive with HLA-B12 and HLA-B60, respectively, raised by in vitro secondary immunization of peripheral blood lymphocytes, Hum. Immunol 36(3):186-192 (1993).
Nakano et al., High speed polymerase chain reaction in constant flow, Biosci Biotech and Biochem, 58:349-52 (1994).
Nakano et al., Single-molecule PCR using water-in-oil emulsion, J Biotech, 102:117-24 (2003).
Nakano et al., Single-molecule reverse transcription polymerase chain reaction using water-in-oil emulsion, J Biosci Bioeng 99:293-295 (2005).
Nametkin, S.N. et al., Cell-free translation in reversed micelles, FEB Letters, 309(3):330-32 (1992).
Narang et al, Improved phosphotriester method for the synthesis of gene fragments, Methods Enzymol, 68:90-98 (1979).
Nelson, P. S., et al., Bifunctional oligonucleotide probes synthesized using a novel CPG support are able to detect single base pair mutations, Nucl Acids Res 17(18): 7187-7194 (1989).
Nemoto et al., In vitro virus: bonding of mRNA bearing puromycin at the 3 terminal end to the C-terminal end of its encoded protein on the ribosome in vitro, Federation of European Biochemical Societies, 414:405-8 (1997).
Ness, J.E. et al., Molecular Breeding: the natural approach to protein design. Adv Protein Chem, 55: 261-292 (2000).
Ng et al., Protein crystallization by capillary counter-diffusion for applied crystallographic structure determination, J. Struct. Biol, 142:218-231(2003).
Ng, B.L. et al., Factors affecting flow karyotype resolution, Cytometry, Part A 69A: 1028-1036 (2006).
Nguyen et al., Optical detection for droplet size control in microfluidic droplet-based analysis systems, Sensors and Actuators B 117(2):431-436 (2006).

(56) References Cited

OTHER PUBLICATIONS

Nihant et al., Polylactide Microparticles Prepared by Double Emulsion/Evaporation Technique. I. Effect of Primary Emulsion Stability, Pharmaceutical Research, 11(10):1479-1484 (1994).
Nisisako et al., Controlled formulation of monodisperse double emulsions in a multiple-phase microluidic system, Sot Matter, 1:23-27 (2005).
Nisisako et al., Formation of droplets using branch channels in a microfluidic circuit, Proceedings of the SICE Annual Conference. International Session Papers,1262-1264 (2002).
Nisisako et al., Microstructured Devices for Preparing Controlled Multiple Emulsions. Chem. Eng. Technol 31(8):1091-1098 (2008).
Nisisako, Takasi et al., Droplet Formation in a MicroChannel NetWO rk, Lab on a Chip, vol. 2, 2002, pp. 24-26.
Nissim, A. et al., Antibody fragments from a single pot phage display library as immunochemical reagents, Embo J, 13:692-8 (1994).
Nof and Shea, Drug-releasing scaffolds fabricated from drug-loaded microspheres, J. Biomed Mater Res 59:349-356 (2002).
Norman, A., Flow Cytometry, Med. Phys., 7(6):609-615 (1980).
Oberholzer R. Ed., Enzymatic RNA replication in self-reproducing vesicles: an approach to a minimal cell, Biochem Biophys Res Commun 207(1):250-7 (1995).
Oberholzer et al., Polymerase chain reaction in liposomes, Chem. Biol. 2(10):677-82 (1995).
Obukowicz, M.G. et al., Secretion and export of IGF-1 in *Escerichia coli* strain JM101, Mol Gen Genet, 215:19-25 (1988).
Office Action for U.S. Appl. No. 11/246,911 dated Feb. 8, 2011.
Office Action for U.S. Appl. No. 11/360,845 dated Apr. 26, 2011.
Office Action for U.S. Appl. No. 11/360,845 dated Aug. 4, 2010.
Office Action for U.S. Appl. No. 11/698,298, dated Jun. 29, 2011.
Ogura, Y., Catalase activity at high concentrations of hydrogen peroxide, Archs Biochem Biophys, 57: 288-300 (1955).
Oh et al., Distribution of Macropores in Silica Particles Prepared by Using Multiple Emulsions, Journal of Colloid and Interface Science, 254(1): 79-86 (2002).
Okushima et al. Controlled production of monodisperse double emulsions by two-step droplet breakup in microfluidic devices, Langmuir 20(23): 9905-8 (2004).
Olsen et ai., Function-based isolation of novel enzymes from a large library, Nat Bioteoltnol 13(10):1071-4 (2000).
Omburo, G.A. et al., Characterization of the zinc binding site of bacterial phosphotriesterase, J of Biological Chem, 267:13278-83 (1992).
Oroskar et al., Detection of immobilized amplicons by ELISA-like techniques, Clin. Chem. 42:1547-1555 (1996).
Ostermeier, M. et al., A combinatorial approach to hybrid enzymes independent of DNA homology, Nat Biotechnol, 17(12):1205-9 (1999).
Ouelette, A new wave of microfluidic devices, Indust Physicist pp. 14-17 (2003).
Pabit et al., Laminar-Flow Fluid Mixer for Fast Fluorescence Kinetics Studies, Biophys J 83:2872-2878 (2002).
Paddison et al., Stable suppression of gene expression by RNAi in mammalian cells, PNAS 99(3):1443-1448 (2002).
Pannacci et al., Equilibrium and Nonequilibrium States in Microluidic Double Emulsions Physical Review Leters, 101(16):164502 (2008).
Park et al., Cylindrical compact thermal-cycling device for continuoflow polymeras chain reaction, Anal Chem, ACS, 75:6029-33 (2003).
Park et al., Model of Formation of Monodispersed Colloids, J. Phys. Chem. B 105:11630-11635 (2001).
Parker et al., Development of high throughput screening assays using fluorescence polarization: nuclear receptor-ligand-binding and kinase/phosphatase assays, J Biomol Screen, 5(2): 77-88 (2000).
Parmley et al., Antibody-selectable filamentous fd phage vectors: affinity purification of target genes. Gene 73(2):305-18 (1988).
Pedersen et al., A method for directed evolution and functional cloning of enzymes, PNAS 95(18):10523-8 (1998).
Pelham and Jackson, An efficient mRNA-dependent translation system from reticulocyte lysates, Eur J Biochem 67:247-56 (1976).
Pelletier et al., An in vivo library-verslibrary selection of optimized protein-protein interactions, Nature Biotechnology, 17:683-90 (1999).
Peng et al., Controlled Production of Emulsions Using a Crossflow Membrane, Particle & Particle Systems Characterization 15:21-25 (1998).
Perelson et al., Theorectical studies of clonal selection: minimal antibody repertoire size and relaibility of self-non-self discrimination. J Theor Biol 81(4):645-70 (1979).
Perez-Gilabert et al., Application of active-phase plot to the kinetic analysis of lipoxygenase in reverse micelles, Biochemistry J. 288:1011-1015 (1992).
Perrin, J., Polarisation de la lumiere de fluorescence vie moyenne des molecules dans letat excite, J. Phys. Rad. 1:390-401 (1926).
Petrounia, I.P. et al., Designed evolution of enzymatic properties, Curr Opin Biotechnol, 11:325-330 (2000).
Piemi et al., Transdermal delivery of glucose through hairless rat skin in vitro: effect of multiple and simple emulsions, Int J Pharm, 171:207-215 (1998).
Pirrung et al., A General Method for the Spatially Defined Immobilization of Biomolecules on Glass Surfaces Using 'Caged' Biotin, Bioconjug Chem 7: 317-321 (1996).
Ploem, In Fluorescent and Luminescent Probes for Biological Activity Mason, T. G. Ed., Academic Press, Landon, pp. 1-11, 1993.
Pluckthun, A. et al., in vitro selection and evolution of proteins, Adv Protein Chem, 55: 367-403 (2000).
Pollack et al., Electrowetting-based actuation of droplets for integrated microfluidics, Lab Chip 2:96-101 (2002).
Pollack et al., Selective chemical catalysis by an antibody, Science 234(4783):1570-3 (1986).
Pons et al, Synthesis of Near-Infrared-Emitting, Water-Soluble CdTeSe/CdZnS Core/Shell Quantum Dots, Chemistry of Materials 21(8):1418-1424 (2009).
Posner et al., Engineering specificity for folate into dihydrofolate reductase from *Escherichia coli*, Biochemistry, 35: 1653-63 (1996).
Poulin and Theil, "A priori" prediction of tissue: plasma partition coefficients of drugs to facilitate the use of physiologically-based pharmokinetic models in drug discovery, J Pharm Sci 89(1):16-35 (2000).
Priest, et al. Generation of Monodisperse Gel Emulsions in a Microfluidic Device, Applied Physics Letters, 88:024106 (2006).
Qi et al., Acid Beta-Glucosidase: Intrinsic Fluorescence and Conformational Changes Induced by Phospholipids and Saposin C, Biochem., 37(33): 11544-11554 (1998).
Raghuraman et al., Emulston Liquid Membranes for Wastewater Treatment: Equillibrium Models for Some Typical Metal-Extractant Systems,Environ. Sci. Technol 28:1090-1098 (1994).
Ralhan, Discovery and Verification of Head-and-neck Cancer Biomarkers by Differential Protein Expression Analysis Using iTRAQ Labeling, Multidimensional Liquid Chromatography, and Tandem Mass Spectrometry, Mol Cell Proteomics 7(6):1162-1173 (2008).
Ramsey, J.M., The burgeoning power of the shrinking laboratory, Nat Biotechnol 17(11):1061-2 (1999).
Ramstrom and Lehn, Drug discovery by dynamic combinatorial libraries, Nat Rev Drug Discov 1:26-36 (2002).
Raushel, F.M. et al., Phosphotriesterase: an enzyme in search of its natural substrate, Adv Enzymol Relat Areas Mol Biol, 74: 51-93 (2000).
Rech et al., Introduction of a yeast artificial chromosome vector into *Sarrachomyeces cervesia* by electroporation, Nucleic Acids Res 18:1313 (1990).
Reyes et al., Micro Total Analysis Systems. 1. Introduction, Theory and Technology, Anal Chem 74(12):2623-2636 (2002).
Riess, J.S., Fluorous micro- and nanophases with a biomedical perspective, Tetrahedron 58(20):4113-4131 (2002).
Roach et al., Controlling nonspecific protein adsorption in a plug-based microfluidic system by controlling inteifacial chemistry using fluorophase surfactants, Anal. Chem. 77:785-796 (2005).
Roberts & Ja, In vitro selection of nucleic acids and proteins: What are we learning, Curr Opin Struct Biol 9(4): 521-9 (1999).
Roberts et al., Simian virus 40 DNA directs synthesis of authentic viral polypeptides in a linked transcription-translation cell-free system 72(5):1922-1926 (1975).

(56) References Cited

OTHER PUBLICATIONS

Roberts, et al., RNA-peptide fusion for the in vitro selection of peptides and proteins, PNAS 94:12297-302 (1997).
Roberts, J.W.,Termination factor for RNA synthesis, Nature, 224: 1168-74 (1969).
Roberts, R.W. Totally in vitro protein selection using mRNA-protein fusions and ribosome display. Curr Opin Chem Biol 3(3), 268-73 (1999).
Rodriguez-Antona et al., Quantitative RT-PCR measurement of human cytochrome P-450s: application to drug induction studies. Arch. Biochem. Biophys., 376:109-116 (2000).
Rolland et al., Fluorescence Polarization Assay by Flow Cytometry, J. Immunol. Meth., 76(1): 1-10 (1985).
Rosenberg et al.,Termination of transcription in bacteriophage lambda, J Biol Chem, 250: 4755-64 (1975).
Rosenberry, T.L., Acetylcholinesterase, Adv Enzymol Relat Areas Mol Biol, 43: 103-218 (1975).
Rotman, Measurement of activities of single molecules of beta-galactosidase, PNAS, 47:1981-91 (1961).
Russon et al., Single-nucleotide polymorphism analysis by allele-specific extension of fluorescently labeled nucleotides in a microfluidic flow-through device, Electrophoresis, 24:158-61 (2003).
Sadtler et al., Achieving stable, reverse water-in-fluorocarbon emulsions. Angew Chem Int Ed 35:1976-1978 (1996).
Saiki, R.K, et al, Primer directed enzymatic amplification of DNA with a thermostable DNA polymerase. Science 239(4839):487-91 (1988).
Sakamoto, Rapid and simple quantification of bacterial cells by using a microfluidic device, Appl Env Microb. 71:2 (2005).
Sanchez et al., Breakup of Charged Capillary Jets, Bulletin of the American Physical Society Division of Fluid Dynamics 41:1768-1768 (1996).
Sano, T. et al., Immuno-PCR—Very sensitive antigen-detection by means of sepcific antibody-DNA conjugates. Science 258(5079), 120-122 (1992).
SantaLucia, A unified view of polymer, dumbbell, and oligonucleotide DNA nearest-neighbor thermodynamics, PNAS 95(4):1460-5 (1998).
Santra et al., Fluorescence lifetime measurements to determine the core-shell nanostructure of FITC-doped silica nanoparticles: An optical approach to evaluate nanoparticle photostability, J Luminescence 117(1):75-82 (2006).
Schatz et al., Screening of peptide libraries linked to lac repressor, Methods Enzymol 267: 171-91 (1996).
Schneegass et al., Miniaturized flow-through PCR with different template types in a silicone chip thermocycler, Lab on a Chip, Royal Soc of Chem, 1:42-9 (2001).
Schubert et al., Designer Capsules, Nat Med 8:1362 (2002).
Schweitzer et al., Immunoassays with rolling circle DNA amplification: A versatile platform for ultrasensitive antigen detection, PNAS 97(18), 10113-10119 (2000).
Schweitzer, B. et al., Combining nucleic acid amplification and detection. Curr Opin Biotechnol 12(1):21-7 (2001).
Scott, R.L., The Solubility of Fluorocarbons, J. Am. Chem. Soc, 70: 4090-4093 (1948).
Seethala and Menzel, Homogeneous, Fluorescence Polarization Assay for Src-Family Tyrosine Kinases, Anal Biochem 253(2):210-218 (1997).
Seiler et al., Planar glass chips for capillary electrophoresis: repetitive sample injection, quantitation, and separation efficiency, Anal Chem 65(10):1481-1488 (1993).
Selwyn M. J., A simple test for inactivation of an enzyme during assay, Biochim Biophys Acta 105:193-195 (1965).
Seo et al., Microfluidic consecutive flow-focusing droplet generators, Soft Matter, 3:986-992 (2007).
Seong and Crooks, Efficient Mixing and Reactions Within Microfluidic Channels Using Microbead-Supported Catalysts, J Am Chem Soc 124(45):13360-1 (2002).
Seong et al., Fabrication of Microchambers Defined by Photopolymerized Hydrogels and Weirs Within Microfluidic Systems: Application to DNA Hybridization, Analytical Chem 74(14):3372-3377 (2002).
Sepp et al., Microbead display by in vitro compartmentalisation: selection for binding using flow cytometry, FEBS Letters 532:455-58 (2002).
Serpersu et al., Reversible and irreversible modification of erythrocyte membranse permeability by electric field, Biochim Biophys Acta 812(3):779-785 (1985).
Shapiro, H.M., Multistation multiparameter flow cytometry: a critical review and rationale, Cytometry 3: 227-243 (1983).
Shestopalov et al., Multi-Step Synthesis of Nanoparticles Performed on Millisecond Time Scale in a Microfluidic Droplet-Based System, The Royal Society of Chemistry 4:316-321(2004).
Shtern V, and Hussain F., Hysteresis in swirling jets, J. Fluid Mech. 309:1-44 (1996).
Sia &Whitesides, Microfluidic devices fabricated in poly(dimethylsiloxane) for biological studies, Electrophoresis 24(21):3563-3576 (2003).
Sidhu, S.S., Phage display in pharmaceutical biotechnology, Curr Opin Biotech 11:610-616 (2000).
Siemering et al., Mutations that suppress the thermosensitivity of green fluorescent protein, Current Biology 6:1653-1663 (1996).
Silva-Cunha et al., W/O/W multiple emulsions of insulin containing a protease inhibitor and an absorption enhancer: biological activity after oral administration to normal and diabetic rats, Int J Pharm 169:33-44 (1998).
Sims et al., Immunopolymerase chain reaction using real-time polymerase chain reaction for detection, Anal. Biochem. 281(2):230-2 (2000).
Slappendel et al., Normal cations and abnormal membrane lipids in the red blood cells of dogs with familial stomatocytosis hypertrophic gastritis, Blood 84:904-909 (1994).
Slob et al., Structural identifiability of PBPK models: practical consequences for modeling strategies and study designs, Crit Rev Toxicol. 27(3):261-72 (1997).
Smith et al., Direct mechanical measurements of the elasticity of single DNA molecules by using magnetic beads, Science 258(5085):1122-1126 (1992).
Smith et al., Fluorescence detection in automated DNA sequence analysis, Nature 321:674-679 (1986).
Smith et al., Phage display, Chemical Reviews 97(2), 391-410 (1997).
Smith et al., The synthesis of oligonucleotides containing an aliphatic amino group at the 5' terminus: synthesis of fluorescent DNA primers for use in DNA sequence analysis, Nucl. Acid Res. 13:2399-2412 (1985).
Smith G.P., Filamentous fusion phage: novel expression vectors that display cloned antigens on the virion surface, Science 228(4705): 1315-7(1985).
Smyth et al., Markers of apoptosis: methods for elucidating the mechanism of apoptotic cell death from the nervous system, Biotechniques 32:648-665 (2000).
Sohn, et al, Capacitance cytometry: Measuring biological cells one by one, PNAS 97(20):10687-10690 (2000).
Somasundaram and Ramalingam, Gain studies of Rhodamine 6G dye doped polymer laser, J Photochem Photobiol 125(1-3):93-98 (1999).
Song et al., A microfluidic system for controlling reaction networks in time, Angew. Chem. Int. Ed. 42(7):768-772 (2003).
Song et al., Experimental Test of Scaling of Mixing by Chaotic Advection in Droplets Moving Through Microfluidic Channels, App Phy Lett 83(22):4664-4666 (2003).
Song, H. and Ismagilov, R.F., Millisecond kinetics on a microluidic chip using nanoliters of reagents, J Am Chem Soc. 125: 14613-14619 (2003).
Soni and Meller, Progress toward ultrafast DNA sequencing using solid-state nanopores, Clin Chem 53:1996-2001 (2007).
Soumillion et al., Novel concepts for the selection of catalytic activity. Curr Opin Biotechnol 12:387-394 (2001).
Soumillion et al., Selection of B-lactomase on filamentous bacteriophage by catalytic activity, J Mol Biol, 237:415-22 (1994).

(56) References Cited

OTHER PUBLICATIONS

Sproat et al., The synthesis of protected 5'-mercapto-2',5'-dideoxyribonucleoside-3'-0-phosphorainidites, uses of 5'-mercapto-oligodeoxyribonucleotides, Nucleic Acids Res 15:4837-4848 (1987).
Stauber, et a., Rapid generation of monoclonal antibody-secreting hybridomas against African horse sickness virus by in vitro immunization and the fusion/cloning technique, J. Immunol. Meth 161(2):157-168 (1993).
Stemmer, W.P., DNA shuffling by random fragmentation and reassembly: in vitro recombination for molecular evolution. PNAS 91(22):10747-51(1994).
Stemmer, W.P., Rapid evolution of a protein in vitro by DNA shuffling, Nature 370(6488):389-91 (1994).
Stober et al., Controlled growth of monodisperse silica spheres in the micron size range, J Colloid and Interface Sci 26(1):62-69 (1968).
Stofko, H.R. et al., A single step purification for recombinant proteins. Characterization of microtube associated protein (MAP2) fragment which associates with the type II cAMP-dependent protein kinase, FEBS Lett 302: 274-278 (1992).
Stone et al., Engineering flows in small devices: Microfluidics toward a lab-on-a-chip, Ann. Rev. Fluid Mech. 36:381-441 (2004).
Strizhkov et al., PCR amplification on a microarray of gel-immobilized oligonucleotides: Detection of bacterial toxin- and drug-resistant genes and their mutations, BioTechniques 29(4):844-857 (2000).
Stroock et al., Chaotic mixer for microchannels, Science 295(5555):647-651 (2002).
Studer et al., Fluorous Synthesis: A FluoroPhase Strategy for Improving Separation Efficiency in Organic Synthesis, Science 275: 823-826 (1997).
Sugiura et al., Effect of Channel Structure on MicroChannel Emuisification, Langmuir 18:5708-5712 (2002).
Sugiura et al., Interfacial tension driven monodispersed droplet formation from mtcrofabricated channel array Langmuir, 17: 5562-5566 (2001).
Sundberg et al., Spatially-Addressable Immobilisation of Macromolecules on Solid Supports, J. Am. Chem. Soc, 117:12050-12057 (1995).
Sung et al. Chip-based microfluidic devices coupled with electrospray ionization-mass spectrometry, Electrophoresis 26:1783-1791 (2005).
Suzuki et al., Random mutagenesis of thermus aquaticus DNA polmerase I: concordance of immutable sites in vivo with the crystal structure, PNAS USA, 93:96701-9675 (1996).
Tabatabai and Faghri, A New Two-Phase Flow Map and Transition Boundary Accounting for Surface Tension Effects in Horizontal Miniature and Micro Tubes, J Heat Transfer 123:958-968 (2001).
Tabatabai et al, Economic feasability study of polyelectrolyte-enhanced ultrafiltration (PEUF) for water softening, J Membrane Science 100(3):193-207 (1995).
Tabatabai et al., Reducing Surfactant Adsorption on Carbonate Reservoirs, SPE Resenroir Engineering 8(2):117-122 (1993).
Tabatabai, Water Softening Using polyelectrolyte-enhanced ultrafiltration, Separation Science Technology 30(2):211-224 (1995).
Takayama et al., Patterning Cells and Their Environments Using Multiple Laminar Fluid Flows in Capillary NetWO rks, PNAS 96:5545-5548 (1999).
Takeuchi et al., An Axisymmetric Flow-Focusing Microfluidic Device, Adv. Mater 17(8):1067-1072 (2005).
Taly et al., Droplets as Microreactors for High-Throughput Biology, Chembiochem 8(3):263-272 (2007).
Tan et al., Controlled Fission of Droplet Emulsions in Bifurcating Microfluidic Channels, Transducers Boston (2003).
Tan et al., Design of microluidic channel geometries for the control of droplet volume, chemical concentration, and sorting, Lab Chip, 4(4): 292-298 (2004).
Tan et al., Monodispersed microfluidic droplet generation by shear focusing microfluidic device, Sensors and Actuators 114:350-356 (2006).
Tan, Y.C., Microfluidic Liposome Generation from Monodisperse Droplet Emulsion-Towards the Realization of Artificial Cells, Summer Bioengineering Conference, Florida (2003).
Tan, Y.C., Monodisperse Droplet Emulsions in Co-Flow Microfluidic Channels, Micro TAS, Lake Tahoe (2003).
Tanaka et al., Ethanol Production from Starch by a Coimmobilized Mixed Culture System of Aspergillus awamori and Zymomonas mobilis, Biotechnol Bioeng XXVII:1761-1768 (1986).
Tang et al., A multi-color fast-switching microfluidic droplet dye laser, Lab Chip 9:2767-2771 (2009).
Taniguchi et al., Chemical Reactions in Microdroplets by Electrostatic Manipulation of Droplets in Liquid Media, Lab on a Chip 2:19-23 (2002).
Tawfik et al., catELISA: a facile general route to catalytic antibodies, PNAS 90(2):373-7 (1993).
Tawfik et al., Efficient and selective p-nitrophenyl-ester= hydrolyzing antibodies elicited by a p-nitrobenzyl phosphonate hapten, Eur J Biochem, 244:619-26 (1997).
Tawfik et al., Man-made cell-like compartments for molecular evolution, Nature Biotechnology, 7(16):652-56 (1998).
Tawfik, D.S. et al., 1,8-diabycyclo[5.4.0]undecane mediated transesterification of p-nitrophenyl phosphonates—a novel route to phosphono esters, Synthesis—Stuttgart, 10: 968-972 (1993).
Taylor et al., Characterization of chemisorbed monolayers by surface potential measurments, J. Phys. D. Appl. Phys. 24:1443 (1991).
Taylor, the formation of emulsions in definable field of flow, Proc R Soc London A 146(858):501-523 (1934).
Tchagang et al., Early detection of ovarian cancer using group biomarkers, Mol Cancer Ther 7:27-37 (2008).
Tencza et al., Development of a Fluorescence Polarization-Based Diagnostic Assay for Equine Infectious Anemia Virus, J Clinical Microbiol 38(5):1854-185 (2000).
Terray et al., Microfluidic Control Using Colloidal Devices,Science, 296(5574):1841-1844 (2002).
Terray, et al, Fabrication of linear colloidal structures for microfluidic applications, Applied Phys Lett 81(9):1555-1557 (2002).
Tewhey et al., Microdroplet-based PCR amplification for large scale targeted sequencing, Nat Biotechnol 27(11):1025-1031 (2009).
Theberge et al., Microdroplets in Microfluidics: An Evolving Platform for Discoveries in Chemistry and Biology, Angew. Chem. Int. Ed 49(34):5846-5868 (2010).
Thompson, L.F., Introduction to Lithography, ACS Symposium Series 219:1-13, (1983).
Thorsen et al., Dynamic pattern formation in a vesicle-generating microfluidic device, Phys Rev Lett 86(18):4163-4166 (2001).
Thorsen et al., Microfluidic Large-Scale Integration, Science 298:580-584 (2002).
Tice et al., Effects of viscosity on droplet formation and mixing in microfluidic channels, Analytica Chimica Acta 507:73-77 (2004).
Tice et al., Formation of droplets and mixing in multiphase microfluidics at low values of the reynolds and the capillary numbers, Langmuir 19:9127-9133 (2003).
Titomanlio et al., Capillary experiments of flow induced crystallization of HOPE, AIChe Journal, 36(1):13-18(1990).
Tleugabulova et al., Evaluating formation and growth mechanisms of silica particles using fluorescence anisotropy decay analysis, Langmuir 20(14):5924-5932 (2004).
Tokatlidis et al., Nascent chains: folding and chaperone intraction during elongation on ribosomes, Philos Trans R Soc Lond B Biol Sci, 348:89-95 (1995).
Tokeshi et al., ContinuoFlow Chemical Processing on a Microchip by Combining Microunit Operations and a Multiphase Flow NetWO rk, Anal Chem 74(7):1565-1571 (2002).
Tokumitsu, H. et al., Preparation of gadopentetic acid-loaded chitosan microparticles for gadolinium neutron-capture therapy of cancer by a novel emulsion-droplet coalescence technique, Chem and Pharm Bull 47(6):838-842 (1999).
Tramontano, A., Catalytic antibodies, Science 234(4783):1566-70 (1986).
Trindade, T., Nanocrystalline semiconductors: synthesis, properties, and perspectives, Chem. Mat. 13:3843-3858 (2001).
Tripet, B. et al., Engineering a de novo-designed coiled-coil heterodimerization domain off the rapid detection, purification and

(56) References Cited

OTHER PUBLICATIONS characterization of recombinantly expressed peptides and proteins, Protein Engng., 9:1029-42 (1996).
Tuerk, C. and Gold, L., Systematic Evolution of Ligands by Exponentid Enrichment: RNA Ligands to Bacteriophage T4 DNA Polymerase, Science, 249:505-10 (1990).
Umbanhowar et al., Monodisperse Emulsion Generation via Drop Break Off in a Coflowing Stream, Langmuir 16(2):347-351 (2000).
Unger et al., Monolithic microfabricated valves and pumps by multylayer soft lithography, Science 288(5463):113-116 (2000).
Utada, A. et al., Monodisperse double emulsions generated from a microcapillary device, Science, 308:537-541 (2005).
Vainshtein et al., Peptide rescue of an N-terminal truncation of the stoffel fragment of Taq DNA polymerase, Protein Science, 5:1785-92 (1996).
Van Bockstaele et al., Prognostic markers in chronic lymphocytic leukemia: a comprehensive review, Blood Rev 23(1):25-47 (2009).
Van Dilla et al., Cell Microfluorometry: A Method for Rapid Fluorescence Measurement, Science 163(3872):1213-1214 (1969).
Van Dilla et al., The fluorescent cell photometer: a new method for the rapid measurement of biological cells stained with fluorescent dyes, Annual Report of the Los Alamos Scientific Laboratory of the University of California (Los Alamos, NM), Biological and Medical Research Groupp (H-4) of the Health Division, Compiled by D. G. Ott, pp. 100-105, distributed Jan. 23, 1968.
Vanhooke et al., Three-dimensional structure of the zinc-containing phosphotrieesterase with the bound substrate analog diethy 4-methylbenzylphosphonate, Biochemistry 35:6020-6025 (1996).
Varga, J.M. et al., Mechanism of allergic cross-reactions-I. Multispecific binding of ligands to a mouse monoclonal anti-DNP IgE antibody. Mol Immunol 28(6), 641-54 (1991).
Vary, A homogeneous nucleic acid hybridization assay based on strand displacement, Nucl Acids Res 15(17):6883-6897 (1987).
Venkateswaran et al., Production of Anti-Fibroblast Growth Factor Receptor Monoclonal Antibodies by In Vitro Immunization, Hybirdoma, 11(6):729-739 (1992).
Venter et al., The sequence of the human genome, Science 291(5507):1304-51 (2001).
Vogelstein et al., Digital PCR, PNAS 96(16):9236-9241 (1999).
Voss, E.W., Kinetic measurements of molecular interactions by spectrofluorometry, J Mol Recognit, 6:51-58 (1993).
Wahler, D. et al., Novel methods for biocatalyst screening. Curr Opin Chem Biol, 5: 152-158 (2001).
Walde, P. et al., Oparin's reactions revisited: enzymatic synthesis of poly(adenylic acid) in micelles and self-reproducing vesicles. J Am Chem Soc, 116: 7541-7547 (1994).
Walde, P. et al., Spectroscopic and kinetic studies of lipases solubilized in reverse micelles, Biochemistry, 32(15):4029-34 (1993).
Walde, P. et al., Structure and activity of trypsin in reverse micelles, Eur J Biochem, 173(2):401-9 (1988).
Walker et al., Isothermal in vitro amplification of DNA by a restriction enzyme/DNA polymerase system, PNAS 89(1):392-6 (1992).
Walker et al., Strand displacement amplification—an isothermal, in vitro DNA amplification technique, Nucleic Acid Res, 20(7):1691-6 (1992).
Wang et al., DEP actuated nanoliter droplet dispensing using feedback control, Lab on a Chip 9:901-909 (2008).
Wang et al., Preparation of Titania Particles Utilizing the Insoluble Phase Interface in a MicroChannel Reactor, Chemical Communications 14:1462-1463 (2002).
Wang, A.M. et al., Quantitation of mRNA by the polymerase chain reaction. Proc natl Acad Sci USA 86(24), 9717-21 (1989).
Wang, G.T. et al., Design and synthesis of new fluorogenic HIV protease substrates based on resonance energy transfer, Tetrahedron Lett., 31:6493 (1990).
Warburton, B., Microcapsules for Multiple Emulsions, Encapsulation and Controlled Release, Spec Publ R Soc Chem, 35-51 (1993).

Wasserman et al., Structure and reactivity of allyl-siloxane monolayers formed by reaction of allcyltrichlorosilanes on silicon substrates, Langmuir 5:1074-1087 (1989).
Weil. et al., Selective and accurate initiation of transcription at the Ad2 major late promotor in a soluble system dependent on purified RNA polymerase II and DNA, Cell, 18(2):469-84 (1979).
Werle et al., Convenient single-step, one tube purification of PCR products for direct sequencing, Nucl Acids Res 22(20):4354-4355 (1994).
Wetmur et al., Molecular haplotyping by linking emulsion PCR: analysis of paraoxonase 1 haplotypes and phenotypes, Nucleic Acids Res 33(8):2615-2619 (2005).
Wick et al., Enzyme-containing liposomes can endogenously produce membrane-constituting lipids, Chem Biol 3(4):277-85 (1996).
Widersten and Mannervik, Glutathione Transferases with Novel Active Sites Isolated by Phage Display from a Library of Random Mutants, J Mol Biol 250(2):115-22 (1995).
Wiggins et al., Foundations of chaotic mixing, Philos Transact A Math Phys Eng Sci 362(1818):937-70 (2004).
Williams et al., Amplification of complex gene libraries by emulsion PCR, Nature Methods 3(7):545-550 (2006).
Williams et al., Methotrexate, a high-affinity pseudosubstrate of dihydrofolate reductase, Biochemistry, 18(12):2567-73 (1979).
Wilson, D.S. and Szostak, J.W., In vitro selection of functional nucleic acids, Ann. Rev. Biochem. 68: 611-647 (1999).
Winter et al., Making antibodies by phage display technology, Annu Rev Immunol 12:433-55 (1994).
Wittrup, K.D., Protein engineering by cell-surface display. Curr Opin Biotechnology, 12: 395-399 (2001).
Wolff et al., Integrating advanced functionality in a microfabricated high-throughput fluorescent-activated cell sorter, Lab Chip, 3(1): 22-27 (2003).
Wronski et al., Two-color, fluorescence-based microplate assay for apoptosis detection. Biotechniques, 32:666-668 (2002).
Wu et al., The ligation amplification reaction (LAR)-amplification of specific DNA sequences using sequential rounds of template-dependent ligation, Genomics 4(4):560-9 (1989).
Wyatt et al., Synthesis and purification of large amounts of RNA oligonucleotides, Biotechniques 11(6):764-9 (1991).
Xia and Whitesides, Soft Lithography, Angew. Chem. Int. Ed. 37:550-575 (1998).
Xia and Whitesides, Soft Lithography, Ann. Rev. Mat. Sci. 28:153-184 (1998).
Xu, S. et al., Generation of monodisperse particles by using microfluidics: control over size, shape, and composition, Angew. Chem. Int. Ed. 44:724-728 (2005).
Yamagishi, J. et al., Mutational analysis of structure-activity relationships in human tumor necrosis factor-alpha, Protein Eng, 3:713-9 (1990).
Yamaguchi et al., Insulin-loaded biodegradable PLGA microcapsules: initial burst release controlled by hydrophilic additives, Journal of Controlled Release, 81(3): 235-249 (2002).
Yelamos, J. et al., Targeting of non-Ig sequences in place of the V segment by somatic hypermutation. Nature 376(6537):225-9 (1995).
Yershov et al., DNA analysis and diagnostics on oligonucleotide microchips, PNAS 93(10):4913-4918 (1996).
Yonezawa et al., DNA display for in vitro selection of diverse peptide libraries, Nucleic Acids Research, 31(19): e118 (2203).
Yu et al. Responsive biomimetic hydrogel valve for microfluidics. Appl. Phys. Lett 78:2589-2591 (2001).
Yu et al., Quantum dot and silica nanoparticle doped polymer optical fibers, Optics Express 15(16):9989-9994 (2007).
Yu et al., Specifc inhibition of PCR by non-extendable oligonucleotides using a 5' to 3' exonuclease-deficient DNA polymerase, Biotechniques 23(4):714-6, 718-20 (1997).
Zaccolo, M. et al., An approach to random mutagenesis of DNA using mixtures of triphosphate derivatives of nucleoside analogues. J Mol Biol 255(4):589-603 (1996).
Zakrzewski, S.F., Preparation of tritiated dihydrofolic acid of high specific activity, Methods Enzymol, 539 (1980).
Zaug and Cech, The intervening sequence RNA of Tetrahymena is an enzyme, Science 231(4737):470-5 (1986).

(56) References Cited

OTHER PUBLICATIONS

Zaug and Cech, The Tetrahymena intervening sequence ribonucleic acid enzyme is a phosphotransferase and an acid phosphatase, Biochemistry 25(16):4478-82 (1986).
Zaug et al., The Tetrahymena ribozyme acts like an RNA restriction endonuclease, Nature 324(6096):429-33 (1986).
Zhang et al., A Simple Statistical Parameter for Use in Evaluation and Validation of High Throughput Screening Assays, Journal of Biomolecular Screening, 4(2): 67-73 (1999).
Zhang, Z.Y., Substrate specificity of the protein tyrosine phosphatases, PNAS 90: 4446-4450 (1993).
Zhao, B. et al., Control and Applications of Immiscible Liquids in Microchannels, J. Am. Chem. Soc, vol. 124:5284-5285 (2002).
Zhao, H. et al., Molecular evolution by staggered extension process (StEP) in vitro recombination. Nat Biotechnol 16(3):258-61 (1998).
Zheng et al., A Droplet-Based, Composite PDMS/Glass Capillary Microfluidic System for Evaluating Protein Crystallization Conditions by Microbatch and Vapor-Diffusion Methods with On-Chip X-Ray Diffraction, Angew. Chem.,116:1-4, (2004).
Zheng et al., A Microiuidic Approach for Screening Submicroliter Volumes against Multiple Reagents by Using Performed Arrays of Nanoliter Plugs in a Three-Phase Liquid/Liquid/Gas Flow, Angew. Chem. Int. Ed., 44(17): 2520-2523 (2005).
Zheng et al., Formation of Droplets of Alternating Composition in Microfluidic Channels and Applications to Indexing of Concentrations in Droplet-Based /Assays, Anal. Chem.,76: 4977-4982 (2004).
Zheng et al., Screening of Protein Crystallization Conditions on a Microfluidic Chip Using Nanoliter-Size Droplets, J Am Chem Soc 125(37):11170-11171 (2003).
Zimmermann et al., Dielectric Breakdown of Cell Membranes, Biophys J 14(11):881-889 (1974).
Zimmermann et al., Microscale Production of Hybridomas by Hypo-Osmolar Electrofusion, Hum. Antibod. Hybridomas, 3(1): 14-18 (1992).
Zubay, G., In vitro synthesis of protein in microbial systems, Annu Rev Genet, 7: 267-87 (1973).
Zubay, G., The isolation and properties of CAP, the catabolite gene activator, Methods Enzymol, 65: 856-77 (1980).
Zuckermann, R. et al., Efficient Methods for Attachment of Thiol-Specific Probes to the 3{-end of Synthetic Oligodeoxyribonucleotides, Nucleic Acids Res. 15:5305-5321 (1987).
Extended European Search Report for EP 10840105.0 dated Mar. 23, 2016 (7 pages).

\* cited by examiner

Panel A

MICROFLUIDIC SYSTEMS AND METHODS FOR REDUCING THE EXCHANGE OF MOLECULES BETWEEN DROPLETS

CROSS-REFERENCE TO RELATED APPLICATIONS

This application claims priority to, and the benefit of, U.S. Patent Application No. 61/289,654 filed Dec. 23, 2009, the contents of which are incorporated herein by reference in its entirety.

FIELD OF INVENTION

The present invention is directed to systems and methods to create stable emulsions with low rates of exchange of molecules between droplets.

BACKGROUND OF THE INVENTION

The manipulation of fluids to form fluid streams of desired configuration, discontinuous fluid streams, droplets, particles, dispersions, etc., for purposes of fluid delivery, product manufacture, analysis, and the like, is a relatively well-studied art. Microfluidic systems have been described in a variety of contexts, typically in the context of miniaturized laboratory (e.g., clinical) analysis. Other uses have been described as well. For example, WO 01/89788; WO 2006/040551; U.S. Patent Application Publication No. 2009/0005254; WO 2006/040554; U.S. Patent Application Publication No. 2007/0184489; WO 2004/002627; U.S. Pat. No. 7,708,949; WO 2008/063227; U.S. Patent Application Publication No. 2008/0003142; WO 2004/091763; U.S. Patent Application Publication No. 2006/0163385; WO 2005/021151; U.S. Patent Application Publication No. 2007/0003442; WO 2006/096571; U.S. Patent Application Publication No. 2009/0131543; WO 2007/089541; U.S. Patent Application Publication No. 2007/0195127; WO 2007/081385; U.S. Patent Application Publication No. 2010/0137163; WO 2007/133710 and U.S. Patent Application Publication No. 2008/0014589. Each of these patents and publications is incorporated by reference in their entireties for all purposes.

Precision manipulation of streams of fluids with microfluidic devices is revolutionizing many fluid-based technologies. Networks of small channels are a flexible platform for the precision manipulation of small amounts of fluids. However, virtually all microfluidic devices are based on flows of streams of fluids; this sets a limit on the smallest volume of reagent that can effectively be used because of the contaminating effects of diffusion and surface adsorption. As the dimensions of small volumes shrink, diffusion becomes the dominant mechanism for mixing, leading to dispersion of reactants; moreover, surface adsorption of reactants, while small, can be highly detrimental when the concentrations are low and volumes are small. As a result, current microfluidic technologies cannot be reliably used for applications involving minute quantities of reagent; for example, bioassays on single cells or library searches involving single beads are not easily performed. However, essentially all enabling technology for microfluidic systems developed thus far has focused on single phase fluid flow and there are few equivalent active means to manipulate droplets requiring the development of droplet handling technology. While significant advances have been made in dynamics at the macro-or microfluidic scale, improved techniques and the results of these techniques are still needed. For example, as the scale of these reactors shrinks, contamination effects due to surface adsorption and diffusion limit the smallest quantities that can be used. Additionally, in single phase microfluidic systems the laminar flow in microfluidic devices the concentration of reagents is continually changing in the microchannels due to diffusion and the parabolic flow profile and cross contamination from one droplet sample to another can create serious problems and limit the effectiveness of many biological and chemical assays. These limitations demand new fluid-handling technology.

An alternate approach that overcomes these limitations is the use of aqueous droplets in an immiscible carrier fluid. Droplets provide the ideal microcapsule that can isolate reactive materials, cells, or small particles for further manipulation and study. However, it is necessary that the droplets be both stable against coalescence and that exchange of molecules between droplets is prevented or limited over the time scale of the experiment. The present invention overcomes the current limitations in the field by providing apparatuses and methods for stabilizing droplets against coalescence and to prevent, or limit, the exchange of molecules between droplets to perform various biological and chemical assays efficiently and effectively, especially at high speeds.

SUMMARY OF THE INVENTION

The present invention provides a method which includes: (a) providing within a carrier fluid a plurality of microdroplets including a first microdroplet including a first biological or chemical material and a second microdroplet including a second biological or chemical material, where the carrier fluid is immiscible with the first microdroplet and second microdroplet and includes a first oil and a first surfactant at a first concentration within the first oil; (b) changing the carrier fluid, in the presence of the plurality of microdroplets, by changing (i) some or all of the first oil for a second oil, (ii) some or all of the first surfactant for a second surfactant, (iii) the first concentration to a second concentration, or any combination of (i), (ii) and/or (iii).

The method can further include step (c): providing a microfluidic device and where step (a) further includes providing the plurality of microdroplets and the carrier fluid in the microfluidic device and/or step (b) further includes changing the carrier fluid within the microfluidic device.

The first biological or chemical material and/or the second biological or chemical material can include a tissue, cell, particle, protein, antibody, amino acid, nucleotide, small molecule, pharmaceutical, and/or label.

The first concentration is sufficient to stabilize the microdroplets against coalescing with each other in the first carrier fluid. Preferably, the first concentration prevents coalescence of the microdroplets. The first concentration is determined, at least in part, based on stabilizing the microdroplets over a time frame determined by a reaction and/or detection of the one or more biological and/or chemical materials.

The second concentration is sufficient to reduce exchange of the first biological or chemical material from the first microdroplet to the second microdroplet, or of the second biological or chemical material from the second microdroplet to the first microdroplet. The second concentration is determined, at least in part, based on stabilizing the droplets over a time frame determined by generation and/or use of the first microdroplet and the second microdroplet in one or more libraries.

Step (b) can include changing the first concentration to the second concentration at least in part by providing the second oil substantially free of the first surfactant.

The present invention also provides a method including: (a) generating a plurality of aqueous microdroplets in a continuous phase in a microfluidic device, where the first continuous phase includes a high concentration of a surfactant; and (b) exchanging the first continuous phase containing the high concentration of surfactant for a second continuous phase containing no surfactant or a reduced concentration of surfactant.

Step (b) can be performed within the microfluidic device. Step (b) can be accomplished, at least in part, by shifting the microdroplets from the first continuous phase into a stream of the second continuous phase. The shifting can be accomplished by using obstacles, changing channel depth, by dielectrophoresis, or by buoyancy.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF DRAWINGS

Non-limiting embodiments of the present invention will be described by way of example with reference to the accompanying drawings, which are schematic and are not intended to be drawn to scale. In the drawings, each identical or nearly identical component illustrated is typically represented by a single numeral. For the purposes of clarity, not every component is labeled in every drawing, nor is every component of each embodiment of the invention shown where illustration is not necessary to allow those of ordinary skill in the art to understand the invention.

DETAILED DESCRIPTION OF THE INVENTION

Figure 1:
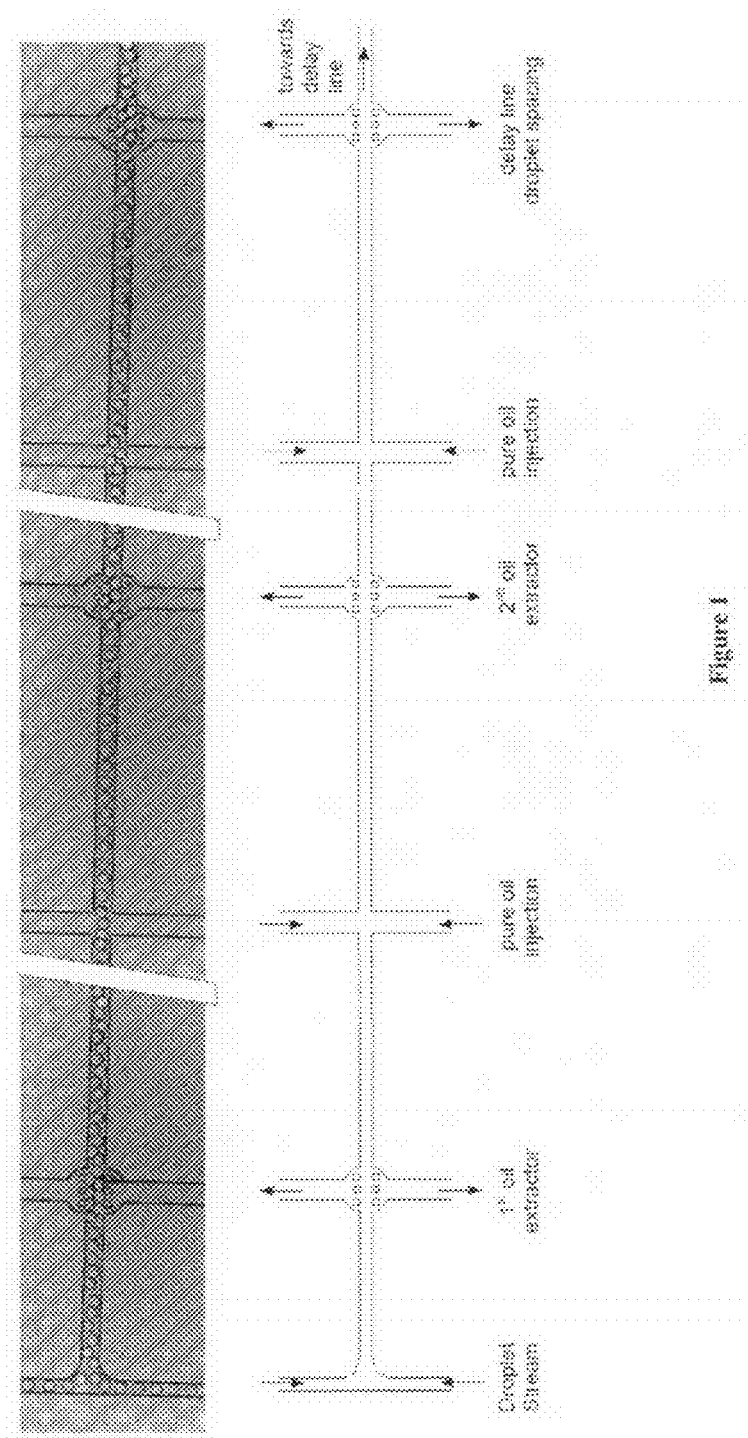
FIG. 1 contains a photograph and accompanying schematic illustrating an actively controlled oil exchange apparatus.

The compartmentalization of assays in wells makes microtitre-plates the most flexible and most widely used screening platform in use today. However, reducing assay volumes to below 1-2 µl is problematic (Mayr, L. M., and Fuerst, P., *J Biomol Screen* 13: 443-448, 2008) and the maximum throughput, even when using sophisticated (and expensive) robotic handling, is little more than 1 $s^{-1}$.

One option is to use microdroplets in water-in-oil emulsions as microrcactors: the droplets have volumes $10^3$ to $10^9$ times smaller than the smallest working volume in a microtitre plate well. In vitro compartmentalization (IVC) (Tawfik, D. S., and Griffiths, A. D., *Nat Biotechnol* 16: 652-656, 1998) of reactions in emulsions was initially developed for directed evolution and has allowed the selection of a wide range of proteins and RNAs for binding, catalytic and regulatory activities (Griffiths, A. D., and Tawfik, D. S., *Trends Biotechnol* 24: 395-402, 2006; Kelly et al., *Chem Commun* (Camb), 1773-1788, 2007; Taly et al., *Chembiochem* 8: 263-272, 2007).

Other applications rapidly followed, notably massively parallel PCR of single DNA molecules (emulsion PCR). The principle of emulsion PCR is to divide a normal PCR mixture between the aqueous droplets of a water-in-oil emulsion such that there is, in most cases, not more than one template DNA molecule per droplet (Dressman et al., *Proc Natl Acad Sci USA* 100: 8817-8822, 2003; Nakano et al., *J Biotechnol* 102: 117-124, 2003). The emulsion is then thermo-cycled and each template DNA molecules is amplified in a separate droplet. This technique for performing massive numbers of single-molecule PCRs in parallel has been used for single-molecule reverse-transcription PCR (Nakano et al., *J Biosci Bioeng* 99: 293-295, 2005), the detection and enumeration of rare genetic mutations (Dressman et al., 2003), haplotyping (Wetmur et al., *Nucleic Acids Res* 33: 2615-2619, 2005), and the high-throughput screening of transcription factor targets (Kojima et al., *Nucleic Acids Res* 33: e150, 2005). Emulsion PCR is also the system used for two commercial 'next-generation' ultra-high-throughput DNA sequencing systems, the Genome Sequencer FLX (Roche) and SOLiD (ABI) systems (Mardis, E. R., *Trends Genet* 24: 133-141, 2008).

In parallel, development of microfluidic systems have developed, which consist of networks of channels of typically 10-100 µm diameter. Small quantities of reagents can be brought together in a specific sequence, mixed and allowed to react for a specified time in a controlled region of the reactor channel network using electrokinetic and/or hydrodynamic pumping. These systems are being developed for use in several areas, including diagnostics and organic synthesis (Fletcher et al., *Tetrahedron* 58: 4735-4757, 2002) and sophisticated microfluidic array chips containing thousands of compartments separated by valves have been created for high-throughput screening (Thorsen et al., *Science* 298: 580-584, 2002). Commercial microfluidic lab-on-a chip systems already represent a serious competing technology for microtitre plates for certain types of screening applications.

However, both IVC of reactions in bulk emulsions and single phase microfluidic systems have certain limitations. The relatively high polydispersity of bulk emulsions makes quantitative experiments difficult as the microreactors (droplets) are not all the same volume. Furthermore, it is difficult to add reagents to pre-droplets (Griffiths and Tawfik, 2006), which limits the range of assays that can be performed. In single phase microfluidic systems the laminar flow in microfluidic devices creates two problems (Song et al., *Angew. Chem. Int. Ed. Engl.* 42: 767-772, 2003): first, mixing is slow; second, the concentration of reagents is changing continually in the microchannels due to diffusion and the parabolic flow profile. Additionally, cross contamination from one sample to another can create serious problems.

These problems can be overcome by combining IVC and microfluidics to create droplet-based microfluidic systems in which the individual assays are compartmentalized in droplet microreactors. Microfluidic modules have been developed which can make highly uniform microdroplets (Umbanhowar et al., *Langmuir* 16: 347-351, 2000; Thorsen et al., *Phys. Rev. Letts.* 86: 4163-4166, 2001; Anna et al., *Applied Physics Letters* 82: 364-366, 2003), fuse droplets (Song et al., 2003; Link et al., *Angew Chem Int Ed Engl* 45: 2556-2560, 2006), mix the contents (Song, H., and Ismagilov, R. F., *J Am Chem Soc* 125: 14613-14619, 2003), incubate droplets in delay lines (Song, H., and Ismagilov, R. F., 2003), split droplets (Song et al., 2003; Link et al., *Phys. Rev. Letts.* 92: 054503, 2004), detect fluorescence in droplets and sort droplets (Link et al., *Angew Chem Int Ed Engl* 45: 2556-2560, 2006; Ahn et al., *Applied Physics Letters* 88: Art. No. 024104, 2006), all at kHz frequencies. It has been shown that biological tests like enzymatic assays and even single cell experiments can be performed in droplets (Clausell-Tormos et al., *Chem Biol* 15: 427-437, 2008; Köster et al., *Lab on a Chip* 8: 1110-1115, 2008). Furthermore, integrated droplet-based microfluidic system can be created in which multiple microfluidic modules are integrated onto a single microfluidic chip (see for example (Frenz et al., *Lab on a Chip* 9: 1344-1348, 2008; Mazutis et al., *Anal Chem* 81: 4813-4821, 2009; Mazutis et al., *Lab Chip* 9: 2902-2908, 2009)).

Droplet-based microfluidic systems have potential applications in many areas, including, but not limited to, organic and inorganic synthesis, protein engineering, directed evolution, high-throughput screening for drug discovery, screening and directed evolution of antibodies and antibody fragments, diagnostics and sequencing.

However, in order to use microdroplets as independent microreactors it is essential that the microdroplets are stable over the time of the experiment and, in some cases, it is necessary to prevent or limit the exchange of molecules between droplets. For example, many biological assays are based on the generation of fluorescent molecules, which must remain within the droplet where such molecules are produced. Additionally, in the case of screening of chemical compound libraries, the chemical compounds being tested must remain within the droplet in which they are encapsulated.

In droplet-based microfluidic experiments the droplets have to be stabilized against coalescence upon first contact. This is achieved by adding surface active components, surfactants, to the mixture. The role of the surfactants is to act against the a-priori metastable state of a macro-emulsion. In the case of microfluidic-generated emulsions, stabilization of the emulsion is a function of both the time required for the surfactant molecules move to the interface and the concentration of the surfactant (Baret et al., *Langmuir* 25: 6088-6093, 2009). In contrast to classical emulsification techniques, the flow focusing junction is the singular place where droplets are formed and therefore all coalescence event afterwards are irreversible. The surfactants in use in microfluidic setups are usually solubilized in the continuous phase and their hydrophilic head group is designed to be very hydrophilic. From these specific constraints follow two consequences: first the molecules show a very low critical micellar concentration (CMC) and second they are present at high concentration to rapidly stabilize the droplet interface. Thus, it is frequently necessary to work at concentrations of about 200 times the CMC which leads to a large excess of surfactant molecules in the continuous phase. A consequence of the presence of these micelles is that small molecules, while not being soluble in the oil phase alone, may interact with the excess surfactant and therefore enter the continuous phase and eventually exchange from one droplet to another.

There are two main mechanisms for molecules to leave an aqueous droplet: the first is the simple leakage into the continuous oil phase though the surfactant membrane stabilizing the droplets against coalescence. This type of loss is referred to as partitioning and is quantified by a partitioning coefficient, log P, that is defined as the logarithm of the ratio of concentrations of compound between the two phases (usually octanol and water). It depends mainly on the hydrophilicity of the compound and thus hydrophobic compounds would easily partition into a hydrocarbon based oil phase. This mechanism usually depletes the droplet of its content but does not necessarily lead to exchange between droplets. One way to avoid this kind of leakage is to use a fluorinated oil as the continuous phase since fluorinated liquids are both hydro- and lipophobic and by suitably choosing the oil, partitioning can be completely removed. Non-fluorinated molecules are essentially completely insoluble in and immiscible in perfluorocarbon carrier oils (Hudlicky, M., and Pavlath, A. E., Chemistry of Organic Fluorine Compounds II. A Critical Review. (Washington: American Chemical Society). 52, 1997; Li et al., *Proc Natl Acad Sci USA* 103: 19243-19248, 2009).

The second mechanisms of leakage is a carrier based transport via micelles. These micelles are present above the CMC and, as they are designed to stabilize a water-oil interface, hydrophilic in their interior. All surfactants are in constant dynamic equilibrium between the droplet interface and the micelles. Small hydrophilic and even lipophilic compounds whose structure is compatible with the surfactant can thus move from the droplet to a micelle and re-enter another droplet later. This leads to considerable exchange of compounds between droplets which can be fast (e.g., 7-amino-4-methyl-coumarin, $\tau=2$ min), slow (e.g., resorufin, $\tau=1$ h) or undetectable (e.g., fluorescein) depend on the compound. This, for example, renders fluorogenic assays based on detecting coumarin impossible, and limits fluorogenic enzymatic assays based on detecting resorufin to incubation times of just a few minutes.

By limiting the surfactant concentrations to values equal or below the CMC, where simply no micelles are present, carrier-based transport of molecules between droplets can be eliminated; however, droplets produced by flow focusing in a microfluidic chip at such low surfactant concentrations are not stabilized and coalesce instantly upon contact (Barct et al., *Langmuir* 25: 6088-6093, 2009). The present invention addresses these problems in the art by providing methods and systems for removing, or at least reducing, the number of micelles in the continuous phase after surfactant-stabilized droplets have been produced by flow focusing within the microfluidic device.

Methods for Reducing Droplet Molecule Exchange

The present invention provides a method which includes:
(a) providing within a carrier fluid a plurality of microdroplets including a first microdroplet including a first biological or chemical material and a second microdroplet including a second biological or chemical material, where the carrier fluid is immiscible with the first microdroplet and second microdroplet and includes a first oil and a first surfactant at a first concentration within the first oil; (b) changing the carrier fluid, in the presence of the plurality of microdroplets, by changing (i) some or all of the first oil for a second oil, (ii) some or all of the first surfactant for a second surfactant, (iii) the first concentration to a second concentration, or any combination of (i), (ii) and/or (iii).

The method can further include step (c): providing a microfluidic device and where step (a) further includes providing the plurality of microdroplets and the carrier fluid in the microfluidic device and/or step (b) further includes changing the carrier fluid within the microfluidic device.

The first biological or chemical material and/or the second biological or chemical material can include a tissue, cell, particle, protein, antibody, amino acid, nucleotide, small molecule, pharmaceutical, and/or label.

The first concentration is sufficient to stabilize the microdroplets against coalescing with each other in the first carrier fluid. Preferably, the first concentration prevents coalescence of the microdroplets. The first concentration is determined, at least in part, based on stabilizing the microdroplets over a time frame determined by a reaction and/or detection of the one or more biological and/or chemical materials.

The second concentration is sufficient to reduce exchange of the first biological or chemical material from the first microdroplet to the second microdroplet, or of the second biological or chemical material from the second microdroplet to the first microdroplet. The second concentration is determined, at least in part, based on stabilizing the droplets over a time frame determined by generation and/or use of the first microdroplet and the second microdroplet in one or more libraries.

Step (b) can include changing the first concentration to the second concentration at least in part by providing the second oil substantially free of the first surfactant.

The present invention also provides a method including: (a) generating a plurality of aqueous microdroplets in a continuous phase in a microfluidic device, where the first continuous phase includes a high concentration of a surfactant; and (b) exchanging the first continuous phase containing the high concentration of surfactant for a second continuous phase containing no surfactant or a reduced concentration of surfactant.

Step (b) can be performed within the microfluidic device. Step (b) can be accomplished, at least in part, by shifting the microdroplets from the first continuous phase into a stream of the second continuous phase. The shifting can be accomplished by using obstacles, changing channel depth, by dielectrophoresis, or by buoyancy.

The present invention provides a method for reducing the exchange of molecules between droplets including, providing a first fluid including a plurality of biological or chemical molecules; providing a second fluid including at least one surfactant, wherein the second fluid is immiscible with the fluid; producing a plurality of droplets of the first fluid including the plurality of biological or chemical molecules within the immiscible second fluid, wherein the droplets are coated with the surfactant, wherein the surfactant prevents coalescence between the droplets; and reducing the concentration of the surfactant in the immiscible second fluid, thereby reducing the exchange of molecules between droplets.

The present invention also provides a method for reducing the exchange of molecules between droplets including, providing a microfluidic substrate including at least two channels; providing a first fluid including a plurality of biological or chemical molecules; providing a second fluid including at least one surfactant, wherein the second fluid is immiscible with the first fluid; producing a plurality of droplets of the first fluid including the plurality of biological or chemical molecules within the second fluid within a first microfluidic channel, wherein the droplets are coated with the surfactant,; and reducing the concentration of the surfactant in the second fluid, thereby reducing the exchange of molecules between droplets.

The present invention also provides method for reducing the exchange of molecules between droplets including, providing a microfluidic substrate including a channel; providing a first fluid including a plurality of biological or chemical molecules; providing a second fluid including at least one surfactant, wherein the second fluid is immiscible with the first fluid; producing a plurality of droplets of the first fluid including the plurality of biological or chemical molecules within the second fluid within the microfluidic channel, wherein the droplets are coated with the surfactant; removing the second fluid including at least one surfactant from the microfluidic channel; and providing an third fluid substantially free of surfactants to the microfluidic channel, wherein the third fluid is immiscible with the plurality of droplets of the first fluid, thereby reducing the exchange of molecules between droplets.

The present invention also provides method for reducing the exchange of molecules between droplets including, providing a microfluidic substrate including at least two channels; providing a first fluid including a plurality of biological or chemical molecules; providing a second fluid including at least one surfactant, wherein the second fluid is immiscible with the first fluid; producing a plurality of droplets of the first fluid including the plurality of biological or chemical molecules within the second fluid within a first microfluidic channel, wherein the droplets are coated with the surfactant; providing a third fluid substantially free of surfactants to within a second microfluidic channel, wherein the third fluid is immiscible with the plurality of droplets of the first fluid; providing a droplet exchange region wherein the at least first channel and the at least second channels merge, wherein the region comprises at least one obstacle; and permitting the plurality of droplets to flow from the second fluid including at least one surfactant to the third fluid substantially free of surfactants, thereby reducing the exchange of molecules between droplets.

The present invention also provides method for reducing the exchange of molecules between droplets including, providing a microfluidic substrate including at least two channels; providing a first fluid including a plurality of biological or chemical molecules; providing a second fluid including at least one surfactant, wherein the second fluid is immiscible with the first fluid; producing a plurality of droplets of the first fluid including the plurality of biological or chemical molecules within the second fluid within a first microfluidic channel, wherein the droplets are coated with the surfactant; providing a third fluid substantially free of surfactants to within a second microfluidic channel, wherein the third fluid is immiscible with the plurality of droplets of the first fluid; providing a droplet exchange region wherein the at least first channel and the at least second channels merge, wherein the region comprises a filter; and permitting the plurality of droplets to flow from the second fluid including at least one surfactant to the third fluid substantially free of surfactants, thereby reducing the exchange of molecules between droplets.

The present invention also provides method for reducing the exchange of molecules between droplets including, providing a microfluidic substrate including at least two channels; providing a first fluid including a plurality of biological or chemical molecules; providing a second fluid including at least one surfactant, wherein the second fluid is immiscible with the first fluid; producing a plurality of droplets of the first fluid including the plurality of biological or chemical molecules within the second fluid within a first microfluidic channel, wherein the droplets are coated with the surfactant; providing a third fluid substantially free of surfactants to within a second microfluidic channel, wherein the third fluid is immiscible with the plurality of droplets of the first fluid; providing a droplet exchange region wherein the at least first channel and the at least second channels merge, wherein the region comprises increased channel dimensions; and directing the plurality of droplets to flow in the increased channel dimensions from the second fluid including at least one surfactant to the third fluid substantially free of surfactants, thereby reducing the exchange of molecules between droplets.

The present invention also provides method for reducing the exchange of molecules between droplets including, providing a microfluidic substrate including at least two channels; providing a first fluid including a plurality of biological or chemical molecules; providing second fluid including at least one surfactant, wherein the second fluid is immiscible with the first fluid; producing a plurality of droplets of the first fluid including the plurality of biological or chemical molecules within the second fluid within a first microfluidic channel, wherein the droplets are coated with the surfactant; providing a third fluid substantially free of surfactants to within a second microfluidic channel, wherein the third fluid is immiscible with the plurality of droplets of the first fluid; providing a droplet exchange region wherein the at least first channel and the at least second channels merge, wherein the region comprises an electric field; and inducing dipoles within the droplets of the plurality to direct the flow of the droplets from the second fluid including at least one surfactant to the third fluid substantially free of surfactants, thereby reducing the exchange of molecules between droplets.

The present invention also provides method for reducing the exchange of molecules between droplets including, providing a microfluidic substrate including at least two channels; providing a first fluid including a plurality of biological or chemical molecules; providing a second fluid including at least one surfactant, wherein the second fluid is immiscible with the first fluid; producing a plurality of droplets of the first fluid including the plurality of biological or chemical molecules within the second fluid within a first microfluidic channel, wherein the droplets are coated with the surfactant; providing a reservoir in fluidic communication with the first microfluidic channel, wherein the reservoir comprises a third fluid substantially free of surfactants, wherein the third fluid is immiscible with the plurality of droplets of the first fluid; directing the plurality of droplets into a first end of the reservoir; continuously providing the third fluid substantially free of surfactants to the reservoir including the droplets; removing the droplets from a second end of the reservoir, wherein the first and second ends are opposing; directing the droplets from the reservoir to a second microfluidic channel within the substrate, thereby reducing the exchange of molecules between droplets.

The first fluid is preferably an aqueous fluid. The second fluid and the third fluid can be an oil. Preferably, the oil is a fluorinated oil. Each droplet in the plurality can include no more than one biological or chemical molecule. Alternatively, each droplet in the plurality includes a plurality of biological or chemical molecules. Preferably, the biological or chemical molecule is selected from the group consisting of tissues, cells, particles, proteins, antibodies, amino acids, nucleotides, small molecule compounds, and pharmaceuticals. Preferably, the biological or chemical compound is a small molecule compound of less than 2000 kDa, which is free of nucleic acids or amino acids. More preferably, the biological or chemical compound is a small molecule compound of less than 500 kDa, which is free of nucleic acids or amino acids.

The surfactant can be a fluorosurfactant. The fluorosurfactant can be a block copolymer consisting of one or more perfluorinated polyether (PFPE) blocks and one or more polyethylene glycol (PEG) blocks. Preferably, the fluorosurfactant is a triblock copolymer consisting of a PEG center block covalently bound to two PFPE blocks by amide linking groups. The fluorosurfactant can have a tail comprising a perfluorinated polyether (PFPE) and hydrophilic head comprising dimorpholinophosphate (DMP) or ammonium carboxylate R24 (See, Clausell-Tormos et al., *Chem Biol* 15: 427-437, 2008; Loeker et al., *Colloids and Surfaces A: Physicochem. Eng. Aspects* 214: 143-150, 2003). Preferably, the fluorosurfactant can have a tail comprising a perfluorinated polyether (PFPE) and hydrophilic head comprising ammonium carboxylate.

Preferably, the third fluid substantially free of surfactants contains less than 5% surfactants; more preferably, the third fluid substantially free of surfactants contains less than 1% surfactants; most preferably, the third fluid substantially free of surfactants contains less than 0.5% surfactants.

Preferably, the third fluid substantially free of surfactants contains less than 5% micelles; more preferably, the third fluid substantially free of surfactants contains less than 1% micelles; most preferably, the third fluid substantially free of surfactants contains less than 0.5% micelles.

Preferably, the amount of molecules exchanged between droplets is reduced 90%; more preferably, the amount of molecules exchanged between droplets is reduced 95%; most preferably, the amount of molecules exchanged between droplets is reduced 99%.

Microdroplets in emulsions can be used as independent microreactors to perform a range of chemical and biological reactions. However, for many applications it is critical to restrict or prevent exchange of molecules between microdroplets. The present invention is a novel system that allows the production of stable emulsions in which there is little or no exchange of molecules between microdroplets. The technique is based on generating aqueous droplets in a oil phase (water-in-oil emulsions) in a microfluidic device using a high concentration of surfactant in the oil phase in order to rapidly stabilize the droplet against coalescence and subsequently exchanging the continuous phase containing the high concentration of surfactant for a continuous phase containing no surfactant, or containing a reduced concentration of surfactant. In this way, stable emulsions can be created in which there is little or no micellar-based transport of molecules between droplets.

In first exemplary embodiment, the surfactant loaded continuous oil phase is replaced with surfactant free oil on a microfluidic chip, this process being actively controlled by pumps. Preferably, the continuous oil phase is replace at least one time, more preferably at least two times and most preferably at least three times.

In a second exemplary embodiment, the laminar flow regime in microfluidic channels is exploited to shift the droplets from the surfactant loaded oil into an adjacent surfactant free, or surfactant reduced, oil stream. Preferably, the droplets can be shifted using obstacles, deep channel sections to direct the high buoyancy droplets, or dielectrophoresis.

In a third exemplary embodiment, the droplets are directed into a reservoir outside of the microfluidic device which contains surfactant free, or surfactant reduced, oil. A continuous stream of surfactant free, or surfactant reduced, oil can be flushed through the reservoir to reduce the surfactant concentration. Preferably, the reservoir is attached to the top of the microfluidic device, the droplets enter the bottom of the reservoir and the continuous stream of surfactant free, or surfactant reduced, oil can is flowed into the top of the reservoir permitting the droplets to cream/rise to the top of the reservoir. Once the droplets have risen to the top of the reservoir, surfactant free, or surfactant reduced, oil can be added from the bottom of the reservoir to force the droplets out of the top of the reservoir where they can be rejected into the microfluidic device, where the continuous phase fluid is a surfactant free, or surfactant reduced, oil.

The oil exchanger chamber constitutes only a part of a microfluidic chip, can be combined with other microfluidic modules, and has many possible applications.

It can be useful for the generation of libraries of molecules stored in droplets in an emulsion, i.e. droplet-based compound libraries. Each droplet contains only a single type of compound from the library (or a small number of different compounds) and there must be little or no exchange of compounds between droplets. Furthermore a code that serves to identify the specific droplet content has to be introduced into each specific droplet. These codes are usually based on fluorophores and thus can exchange similarly.

It can be used to perform enzymatic or cell-based assays, either by combining with an on-chip delay-line (Song, H., and Ismagilov, R. F., *J Am Chem Soc* 125: 14613-14619, 2003; Frenz et al., *Lab on a Chip* 9: 1344-1348, 2008) or with an on- or off-chip reservoir where droplets are incubated prior to analysis (Clausell-Tormos et al., *Chem Biol* 15: 427-437, 2008; Köster et al., *Lab on a Chip* 8: 1110-1115, 2008). Such tests are usually based on the generation of fluorophores from fluorogenic substrates by enzymes. Leakage of either the substrate or the fluorophore limits the effectiveness of these assays. A leaking substrate might even render a specific assay impossible since a fast leaking substrate cannot be converted by a slow enzyme. A leaking fluorophore reduces the dynamic detection range and limits the ability to differentiate subtle differences in enzymatic activity.

The oil exchanger chamber can be coupled to surface tension measurements. In this example, droplets saturated with one type of surfactant can be transferred to an environment with different surface active components (different surfactants, nano beads, etc.) and the constitutional change of the interface can be followed.

Interfacial surfactant desorption dynamics with timescales ranging from millisecond to hours can be studied since the oil exchanger is a unique tool to instantly confront an interface, containing a controlled amount of surfactant, to a surfactant free environment, not possible with other methods.

The microfluidic device of the present invention includes one or more analysis units. An "analysis unit" is a microsubstrate, e.g., a microchip. The terms microsubstrate, substrate, microchip, and chip are used interchangeably herein. The analysis unit includes at least one inlet channel, at least one main channel and at least one inlet module. The analysis unit can further include at least one coalescence module. at least one detection module and one or more sorting modules. The sorting module can be in fluid communication with branch channels which are in fluid communication with one or more outlet modules (collection module or waste module). For sorting applications, at least one detection module cooperates with at least one sorting module to divert flow via a detector-originated signal. It shall be appreciated that the "modules" and "channels" are in fluid communication with each other and therefore may overlap; i.e., there may be no clear boundary where a module or channel begins or ends. A plurality of analysis units of the invention may be combined in one device. The dimensions of the substrate are those of typical microchips, ranging between about 0.5 cm to about 15 cm per side and about 1 micron to about 1 cm in thickness. The analysis unit and specific modules are described in further detail in WO 2006/040551; U.S. Patent Application Publication No. 2009/0005254; WO 2006/040554; U.S. Patent Application Publication No. 2007/0184489; WO 2004/002627; U.S. Pat. No. 7,708,949; WO 2004/091763; U.S. Patent Application Publication No. 2006/0163385; WO 2005/021151; U.S. Patent Application Publication No. 2007/0003442; WO 2006/096571; U.S. Patent Application Publication No. 2009/0131543; WO 2007/089541; U.S. Patent Application Publication No. 2007/0195127; WO 2007/081385; U.S. Patent Application Publication No. 2010/0137163; WO 2007/133710 and U.S. Patent Application Publication No. 2008/0014589.

A variety of materials and methods can be used to form any of the described components of the systems and devices of the invention. For example, various components of the invention can be formed from solid materials, in which the channels can be formed via molding, micromachining, film deposition processes such as spin coating and chemical vapor deposition, laser fabrication, photolithographic techniques, etching methods including wet chemical or plasma processes, and the like. See, for example, Angell, et al., Scientific American, 248:44-55, 1983. At least a portion of the fluidic system can be formed of silicone by molding a silicone chip. Technologies for precise and efficient formation of various fluidic systems and devices of the invention from silicone are known. Various components of the systems and devices of the invention can also be formed of a polymer, for example, an elastomeric polymer such as polydimethylsiloxane ("PDMS"), polytetrafluoroethylene ("PTFE") or Teflon®, or the like.

Silicone polymers are preferred, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying formation of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be formed and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in Duffy et al., "Rapid Prototyping of Microfluidic Systems and Polydimethylsiloxane," Anal. Chem., 70:474-480, 1998.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

The microfluidic substrates of the present invention include channels that form the boundary for a fluid. A "channel," as used herein, means a feature on or in a substrate that at least partially directs the flow of a fluid. In some cases, the channel may be formed, at least in part, by a single component, e.g., an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet.

The channels of the invention can be formed, for example by etching a silicon chip using conventional photolithography techniques, or using a micromachining technology called "soft lithography" as described by Whitesides and Xia, Angewandte Chemie International Edition 37, 550 (1998).

An open channel generally will include characteristics that facilitate control over fluid transport, e.g., structural characteristics (an elongated indentation) and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases.

A "main channel" is a channel of the device of the invention which permits the flow of molecules, cells, small molecules or particles past a coalescence module for coalescing one or more droplets, and, if present, a detection module for detection (identification) or measurement of a droplet and a sorting module for sorting a droplet based on the detection in the detection module. The main channel is typically in fluid communication with the coalescence, detection and/or sorting modules, as well as, an inlet channel of the inlet module. The main channel is also typically in fluid communication with an outlet module and optionally with branch channels, each of which may have a collection module or waste module. These channels permit the flow of molecules, cells, small molecules or particles out of the main channel. An "inlet channel" permits the flow of molecules, cells, small molecules or particles into the main channel. One or more inlet channels communicate with one or more means for introducing a sample into the device of the present invention. The inlet channel communicates with the main channel at an inlet module.

The microfluidic substrate can also comprise one or more fluid channels to inject or remove fluid in between droplets in a droplet stream for the purpose of changing the spacing between droplets.

The channels of the device of the present invention can be of any geometry as described. However, the channels of the device can comprise a specific geometry such that the contents of the channel are manipulated, e.g., sorted, mixed, prevent clogging, etc.

A microfluidic substrate can also include a specific geometry designed in such a manner as to prevent the aggregation of biological/chemical material and keep the biological/chemical material separated from each other prior to encapsulation in droplets. The geometry of channel dimension can be changed to disturb the aggregates and break them apart by various methods, that can include, but is not limited to, geometric pinching (to force cells through a (or a series of) narrow region(s), whose dimension is smaller or comparable to the dimension of a single cell) or a barricade (place a series of barricades on the way of the moving cells to disturb the movement and break up the aggregates of cells).

To prevent material (e.g., cells and other particles or molecules) from adhering to the sides of the channels, the channels (and coverslip, if used) may have a coating which minimizes adhesion. The surface of the channels of the microfluidic device can be coated with any anti-wetting or blocking agent for the dispersed phase. The channel can be coated with any protein to prevent adhesion of the biological/chemical sample. Channels can be coated by any means known in the art. For example, the channels are coated with Teflon®, BSA, PEG-silane and/or fluorosilane in an amount sufficient to prevent attachment and prevent clogging. In another example, the channels can be coated with a cyclized transparent optical polymer obtained by copolymerization of perfluoro (alkenyl vinyl ethers), such as the type sold by Asahi Glass Co. under the trademark Cytop. In such an example, the coating is applied from a 0.1-0.5 wt % solution of Cytop CTL-809M in CT-Solv 180. This solution can be injected into the channels of a microfluidic device via a plastic syringe. The device can then be heated to about 90° C. for 2 hours, followed by heating at 200° C. for an additional 2 hours. In another embodiment, the channels can be coated with a hydrophobic coating of the type sold by PPG Industries, Inc. under the trademark Aquapel (e.g., perfluoroalkylalkylsilane surface treatment of plastic and coated plastic substrate surfaces in conjunction with the use of a silica primer layer) and disclosed in U.S. Pat. No. 5,523,162. By fluorinating the surfaces of the channels, the continuous phase preferentially wets the channels and allows for the stable generation and movement of droplets through the device. The low surface tension of the channel walls thereby minimizes the accumulation of channel clogging particulates.

The surface of the channels in the microfluidic device can be also fluorinated by any means known in the art to prevent undesired wetting behaviors. For example, a microfluidic device can be placed in a polycarbonate dessicator with an open bottle of (tridecafluoro-1,1,2,2-tetrahydrooctyl)trichlorosilane. The dessicator is evacuated for 5 minutes, and then sealed for 20-40 minutes. The dessicator is then backfilled with air and removed. This approach uses a simple diffusion mechanism to enable facile infiltration of channels of the microfluidic device with the fluorosilane and can be readily scaled up for simultaneous device fluorination.

The microfluidic device of the present invention is capable of controlling the direction and flow of fluids and entities within the device. The term "flow" means any movement of liquid or solid through a device or in a method of the invention, and encompasses without limitation any fluid stream, and any material moving with, within or against the stream, whether or not the material is carried by the stream. For example, the movement of molecules, beads, cells or virions through a device or in a method of the invention, e.g. through channels of a microfluidic chip of the invention, comprises a flow. This is so, according to the invention, whether or not the molecules, beads, cells or virions are carried by a stream of fluid also comprising a flow, or whether the molecules, cells or virions are caused to move by some other direct or indirect force or motivation, and whether or not the nature of any motivating force is known or understood. The application of any force may be used to provide a flow, including without limitation, pressure, capillary action, electro-osmosis, electrophoresis, dielectrophoresis, optical tweezers, and combinations thereof, without regard for any particular theory or mechanism of action, so long as molecules, cells or virions are directed for detection, measurement or sorting according to the invention. Specific flow forces are described in further detail herein.

The flow stream in the main channel is typically, but not necessarily, continuous and may be stopped and started, reversed or changed in speed. A liquid that does not contain sample molecules, cells or particles can be introduced into a sample inlet well or channel and directed through the inlet module, e.g., by capillary action, to hydrate and prepare the device for use. Likewise, buffer or oil can also be introduced into a main inlet region that communicates directly with the main channel to purge the device (e.g., or "dead" air) and prepare it for use. If desired, the pressure can be adjusted or equalized, for example, by adding buffer or oil to an outlet module.

As used herein, the term "fluid stream" or "fluidic stream" refers to the flow of a fluid, typically generally in a specific direction. The fluidic stream may be continuous and/or discontinuous. A "continuous" fluidic stream is a fluidic stream that is produced as a single entity, e. g., if a continuous fluidic stream is produced from a channel, the fluidic stream, after production, appears to be contiguous with the channel outlet. The continuous fluidic stream is also referred to as a continuous phase fluid or carrier fluid. The continuous fluidic stream may be laminar, or turbulent in some cases.

Similarly, a "discontinuous" fluidic stream is a fluidic stream that is not produced as a single entity. The discontinuous fluidic stream is also referred to as the dispersed phase fluid or sample fluid. A discontinuous fluidic stream may have the appearance of individual droplets or microdroplets, optionally surrounded by a second fluid. The dispersed phase fluid can include a biological/chemical material. The terms "droplet" and "microdroplet" are used interchangeable herein. The biological/chemical material can be tissues, cells, particles, proteins, antibodies, amino acids, nucleotides, small molecules, and pharmaceuticals. The biological/chemical material can include one or more labels known in the art. The label can be an optical label, an enzymatic label or a radioactive label. The label can be any detectable label, e.g., a protein, a DNA tag, a dye, a quantum dot or a radio frequency identification tag, or combinations thereof. Preferably the label is an optical label. The label can be detected by any means known in the art. Preferably, the label is detected by fluorescence polarization, fluorescence intensity, fluorescence lifetime, fluorescence energy transfer, pH, ionic content, temperature or combinations thereof. Various labels and means for detection are described in greater detail herein.

The term "emulsion" refers to a preparation of one liquid distributed in small globules (also referred to herein as drops, droplets or NanoReactors) in the body of a second liquid. The first and second fluids are immiscible with each other. For example, the discontinuous phase can be an aqueous solution and the continuous phase can a hydrophobic fluid such as an oil. This is termed a water in oil emulsion. Alternatively, the emulsion may be a oil in water emulsion. In that example, the first liquid, which is dispersed in globules, is referred to as the discontinuous phase, whereas the second liquid is referred to as the continuous phase or the dispersion medium. The continuous phase can be an aqueous solution and the discontinuous phase is a hydrophobic fluid, such as an oil (e.g., decane, tetradecane, or hexadecane). The droplets or globules of oil in an oil in water emulsion are also referred to herein as "micelles", whereas globules of water in a water in oil emulsion may be referred to as "reverse micelles".

The fluidic droplets may each be substantially the same shape and/or size. The droplets may be uniform in size. The shape and/or size can be determined, for example, by measuring the average diameter or other characteristic dimension of the droplets. The "average diameter" of a plurality or series of droplets is the arithmetic average of the average diameters of each of the droplets. Those of ordinary skill in the art will be able to determine the average diameter (or other characteristic dimension) of a plurality or series of droplets, for example, using laser light scattering, microscopic examination, or other known techniques. The diameter of a droplet, in a non-spherical droplet, is the mathematically-defined average diameter of the droplet, integrated across the entire surface. The average diameter of a droplet (and/or of a plurality or series of droplets) may be, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The average diameter may also be at least about 1 micrometer, at least about 2 micrometers, at least about 3 micrometers, at least about 5 micrometers, at least about 10 micrometers, at least about 15 micrometers, or at least about 20 micrometers in certain cases.

As used herein, the term "NanoReactor" and its plural encompass the terms "droplet", "nanodrop", "nanodroplet", "microdrop" or "microdroplet" as defined herein, as well as an integrated system for the manipulation and probing of droplets, as described in detail herein. Nanoreactors as described herein can be 0.1-1000 μm (e.g., 0.1, 0.2 . . . 5, 10, 15, 20, 25, 30, 35, 40, 45, 50 . . . 1000), or any size within this range. Droplets at these dimensions tend to conform to the size and shape of the channels, while maintaining their respective volumes. Thus, as droplets move from a wider channel to a narrower channel they become longer and thinner, and vice versa.

The microfluidic substrate of this invention most preferably generate round, highly uniform, monodisperse droplets (<1.5% polydispersity). Droplets and methods of forming monodisperse droplets in microfluidic channels is described in WO 2006/040551; U.S. Patent Application Publication No. 2009/0005254; WO 2006/040554; U.S. Patent Application Publication No. 2007/0184489; WO 2004/002627; U.S. Pat. No. 7,708,949; WO 2004/091763; U.S. Patent Application Publication No. 2006/0163385; WO 2005/021151; U.S. Patent Application Publication No. 2007/0003442; WO 2006/096571; U.S. Patent Application Publication No. 2009/0131543; WO 2007/089541; U.S. Patent Application Publication No. 2007/0195127; WO 2007/081385; U.S. Patent Application Publication No. 2010/0137163; WO 2007/133710 and U.S. Patent Application Publication No. 2008/0014589.

The droplet forming liquid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. However, other solvents, or mixtures of solvents, which are immiscible with the oil phase, may also be used to form droplets, including but not limited to Dimethylsulfoxide (DMSO) and mixtures of water and DMSO. Any liquid or buffer that is physiologically compatible with the population of molecules, cells or particles to be analyzed and/or sorted can be used. The fluid passing through the main channel and in which the droplets are formed is one that is immiscible with the droplet forming fluid. The fluid passing through the main channel can be a non-polar solvent, decane (e.g., tetradecane or hexadecane), fluorocarbon oil, silicone oil or another oil (for example, mineral oil).

The droplet may also contain biological/chemical material (e.g., molecules, cells, or other particles) for combination, analysis and/or sorting in the device. The droplets of the dispersed phase fluid can contain more than one particle or can contain no more than one particle.

Droplets of a sample fluid can be formed within the inlet module on the microfluidic device or droplets (or droplet libraries) can be formed before the sample fluid is introduced to the microfluidic device ("off chip" droplet formation). To permit effective interdigitation, coalescence and detection, the droplets comprising each sample to be analyzed must be monodisperse. As described in more detail herein, in many applications, different samples to be analyzed are contained within droplets of different sizes. Droplet size must be highly controlled to ensure that droplets containing the correct contents for analysis and coalesced properly. As such, the present invention provides devices and methods for forming droplets and droplet libraries.

The fluids used in the invention may contain one or more additives, such as agents which reduce surface tensions (surfactants). Surfactants can include Tween, Span, fluorosurfactants, and other agents that are soluble in oil relative to water. In some applications, performance is improved by adding a second surfactant to the aqueous phase. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing. The present invention provides compositions and methods to stabilize aqueous droplets in a fluorinated oil and minimize the transport of positively charged reagents (particularly, fluorescent dyes) from the aqueous phase to the oil phase.

The droplets may be coated with a surfactant. Preferred surfactants that may be added to the continuous phase fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates). In addition, ionic surfactants such as sodium dodecyl sulfate (SDS) may also be used. However, such surfactants are generally less preferably for many embodiments of the invention. For instance, in those embodiments where aqueous droplets are used as nanoreactors for chemical reactions (including biochemical reactions) or are used to analyze and/or sort biomaterials, a water soluble surfactant such as SDS may denature or inactivate the contents of the droplet.

The carrier fluid can be an oil (e.g., decane, tetradecane or hexadecane) or fluorocarbon oil that contains a surfactant (e.g., a non-ionic surfactant such as a Span surfactant) as an additive (preferably between about 0.2 and 5% by volume, more preferably about 2%). A user can preferably cause the carrier fluid to flow through channels of the microfluidic device so that the surfactant in the carrier fluid coats the channel walls.

Fluorocarbon oil continuous phases are well-suited as the continuous phase for aqueous droplet libraries for a number of reasons. Fluorous oils are both hydrophobic and lipophobic. Therefore, they have low solubility for components of the aqueous phase and they limit molecular diffusion between droplets. Also, fluorous oils present an inert interface for chemistry and biology within droplets. In contrast to hydrocarbon or silicone oils, fluorous oils do not swell PDMS materials, which is a convenient material for constructing microfluidic channels. Finally, fluorocarbon oils have good solubility for gases, which is necessary for the viability of encapsulated cells.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Droplets formed in oil without surfactant are not stable to permit coalescence, so surfactants must be dissolved in the oil that is used as the continuous phase for the emulsion library. Surfactant molecules are amphiphilic—part of the molecule is oil soluble, and part of the molecule is water soluble. When a water-oil interface is formed at the nozzle of a microfluidic chip for example in the inlet module described herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets.

A very large body of fundamental research and commercial application development exists for non-fluorous surfactants and emulsions ranging from sub-micron droplets to very large, macroscopic emulsions. In contrast, fundamental knowledge and commercial practice with fluorinated oils and surfactants is much less common. More specifically, testing and development of fluorosurfactants and fluorous oil formulations for the application of creating large libraries of micron-scale droplets with unique composition is limited to only a few groups throughout the world. Only a few commercially-available fluorosurfactants that stabilize water-in-fluorocarbon oil emulsions exist. For instance, surfactants with short fluorotelomer-tails (typically perfluorinated $C_6$ to $C_{10}$) are available, but they do not provide sufficient long-term emulsion stability. Fluorosurfactants with longer fluorocarbon tails, such as perfluoropolyether (PFPE), are limited to molecules with ionic headgroups.

Classes of oils are available from wide variety of fluorinated oils and are available from commercial sources. The requirements for the oil are (1) immiscibility with the aqueous phase, (2) solubility of emulsion stabilizing surfactants in the oil, and (3) compatibility and/or insolubility of reagents from the droplet phase. Oils include hydrofluoroethers, which are fluorinated alkyl chains coupled with hydrocarbon chemistry through an ether bond. One supplier of this type of oil is 3M. The products are marketed as Novec Engineered Fluids or HFE-series oils. This oils include but are not limited to, HFE-7500, which is a preferred embodiment as it provides superior droplet stability seems to be higher. Other oils include HFE-7100, -7200, -7600, which are examples of other HFEs available from 3M. These can be used as stand-alone oils or components of oil mixtures to optimize emulsion properties and performance. Other hydrofluoroethers are also available from other producers, distributors, or resellers may offer hydrofluoroethers.

Another class of oil is perfluoroalkylamines, which are perfluorinated oils based on perfluoroalkyl amine structures. 3M produces these oils as Fluorinert Electronic Liquids (FC-oils). Fluorinert products differ by variations in alkyl chain length, branch structure, and combinations of different structures or pure oils. Many of them offer the potential for stand-alone oils or components of oil mixtures to optimize emulsion properties and performance. Specific examples are Fluorinert FC-3283, Fluorinert FC-40, which are a preferred embodiments. Higher viscosity and boiling point useful for applications requiring elevated temperature (e.g., thermocyling for PCR). Other Fluorinert series can be used for stand-alone oils or components of oil mixtures to optimize emulsion properties and performance. Again, other perfluoroalkylamines are available from other producers, distributors, or resellers may offer perfluoroalkylamines.

Fluorinated organics/solvents offer a number of perfluorinated or partially fluorinated solvents are available from a variety of producers, distributors, and/or resellers. Many of them offer the potential for stand-alone oils or components of oil mixtures to optimize emulsion properties and performance. Examples of fluorinated organic reagents utilized, included (but not limited to) trifluoroacetic acid and hexafluoroisopropanol, to improve droplet stability in other fluorinated oil systems. Additionally, fluoropolymers may also be used within a microfluidic system. Examples of fluoropolymers include, Krytox GPL oils, Solvay Galden oils, and other liquid fluoropolymers. Other fluorinated materials find widespread use in a variety of industries, but they are generally not well-known in the disciplines of interfacial, colloidal, physical, or synthetic organic chemistry. Therefore, a number of other candidates for oils exist in specialty and niche market applications. As such, new oils have been targeted partially that are per-fluorinated materials, which are not widely recognized.

The properties of oils selected are based upon their chemical properties, such as, among others molecular structure, fluorine content and solvating strength. Physical properties of oils examined include viscosity, boiling point, thermal expansion coefficient, oil-in-water solubility, water-in-oil solubility, dielectric constant, polarity, and oil-in-water surface tension.

Classes of surfactants include fluorosurfactants that can be categorized by the type of fluorophilic portion of the molecule, the type of hydrophilic, or polar, portion, and the chemistry used to link the different parts of the molecule. Materials developed are capable of stabilizing an emulsion or droplet library. One preferred embodiment is the EA surfactant. Specifically, the EA surfactant is a Krytox-PEG- Krytox. The EA surfactant is a nonionic tri-block copolymer surfactant was developed to avoid issues that the ionic surfactants (e.g., RR, see below) which result from the use of some other ionic surfactant. Specifically, ionic surfactants interact with charged species in the droplets and can sequester ions (e.g., magnesium required for the PCR reaction) or other reagents to the oil phase. The structure of the EA surfactant comprises a PEG—approximately 600 Da with amine end functionality, PFPE—Mn is ~5000-8000 from a Krytox FSH starting material and the linker is an amide coupling. Other fluorosurfactants include surfactants with a fluorinated tail of a commercial oil (krytox FSH) and a hydrophilic head (either dimorpholinophosphate (DMP) or ammonium carboxylate R24 (Clausell-Tormos et al., *Chem Biol* 15: 427-437, 2008; Loeker et al., *Colloids and Surfaces A: Physicochem. Eng. Aspects* 214: 143-150, 2003).

Alternative materials are alternative fluorophilic portion, i.e., PFPE (Solvay or Demnum), Poly(fluoroalkylacrylate) and other non-polymeric and partially fluorinated materials. Alternative head-group chemistry for the hydrophilic portion includes, non-ionic head groups like PEG (Mw, Mw/Mn (PDI)) and functionality (i.e., diblock, triblock and dendritic). Others include morpholino. Ionic head groups for the hydrophilic portion include anionic, such as elemental and amine salts and further cationic head portions. Other head group chemistries include zwitterionic, hybrid (e.g., PEG-ionic and zonyl FSO/FSN), lipophilic (e.g, lipophilic to promote bilayer and lipophilic spacer to hydrophile). Another alternative is alternative coupling chemistry such as, phosphoryl/Friedel-Crafts, spacer to organic handle and others.

Characteristics of surfactants are their molecular structure, determined by NMR, chromatography (e.g., HPLC, GPC/SEC), FTIR, mass spectrometry, and titrations. Purity of surfactants is another characteristic examined in addition to the fluorophile-hydrophile balance.

A preferred embodiment includes oil-surfactant formulation for the application of library emulsions is R-oil (HFE-7500) mixed with 2 wt % EA surfactant ("REA20"). Concentrations of EA or RR surfactant at 0.1 wt % or lower to 5% or greater. Other formulations of oils and surfactants and other components added to the aqueous phase are used to improved and optimized the performance of the droplets performance. Those properties of the oil-surfactant mixture include simple mixtures (i.e., one oil and one surfactant, with varied surface concentration), co-surfactants, oil mixtures and additives, such as zonyl and TFA.

Oil and surfactant mixture properties include surfactant solubility, critical micelle concentration (CMC), surfactant diffusivity, and interfacial tension, i.e., dynamic and equilibrium. Emulsion properties are also accounted for, those properties include size (absolute and size distribution), stability, transport, and biocompatibility. Stability relates directly to the coalesced droplets and their deformability/breaking and shredding ability. More particularly, the stability of the droplets in their generation, storage and shipping.

In general, production of surfactant and oils begins with the synthesis of surfactants and starting materials, such as PEG-diamine, EA and RR and also accounts for the purification processes, characterization, quality control, mixing and packaging.

In one embodiment, the fluorosurfactant can be prepared by reacting the perflourinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Flourinert (3M)), which then serves as the continuous phase of the emulsion.

In another embodiment, a quaternary ammonium salt at the terminus of a hydrophilic oligomer is linked to a perfluoropolyether tail as shown in the following formula:
PFPE-C(O)NH—$CH_2CH_2CH_2$—($OCH_2CH_2$)$_3$O—$CH_2CH_2CH_2$—N($CH_3$)$_3$+I—Some specific molecular features of the present invention include, but are not limited to, PFPE is from Krytox 157 FSH (Mn~6500), amide bond linking PFPE to hydrophile, propyl group immediately adjacent to the amide, propyl group immediately adjacent to the trimethylamino terminus Specific structural formations can alter performance relationships, for example, PFPE chain is sufficiently long for molecule to be soluble in perfluorinated oils, amide linker provides hydrolytic stability and hydrogen bonding site, and a combination of PEG and quaternary ammonium cation provide high anchoring strength to the aqueous phase as well as electrostatic repulsion and steric hindrance to minimize reagent transport.

Variables in the molecular structure include, but are not limited to, PFPE molecular weight and polydispersity, PFPE structure, alternative perfluorinated tail chemistries, PEG molecular weight and polydispersity, shorter hydrocarbon linkers (ethyl or methyl versus propyl), longer hydrocarbon spacers (C4 or higher), alternative counterions, such as monovalent anions, monovalent, polyatomic anions and di- or tri-valent counterions (to produce two or more tail fluorosurfactants). Further variables in the molecule structure include alternative linker chemistries (e.g., ether, ester, etc), alternative hydrophilic oligomers (e.g., polyalcohol, polyacrylamide, etc.), alternative quaternary ammonium cations, and alternative ionic groups (e.g., anionic terminus—carboxylate etc.; alternative cations).

The present invention is also directed to the coupling of PEG-diamines with carboxylic acid-terminated perflouropolyether (Krytox 157) to form surfactants. Specifically, the present invention is directed to a fluorosurfactant molecule made by the ionic coupling of amine-terminated polyethyleneglycol (PEG-amine) with the carboxylic acid of DuPont Krytox perfluoropolyether (PFPE). The resulting structure conveys good performance in the stabilization of aqueous droplets in fluorinated oil in a microfluidic system. Examples of preferred surfactants are described in WO 2008/021123 and U.S. Patent Application Publication No. 2010/0105112.

The present invention provides droplets with a fluorosurfactant interface separating the aqueous droplet and its contents from the surrounding immiscible fluorocarbon oil. In one example, DNA amplification reactions occurring inside these droplets generate material that does not interact with the channel walls, and collection of the DNA-containing droplets for subsequent manipulation and sequencing is straightforward. This technology provides a solution for amplification of DNA from single cells, allowing for both genotyping and whole genome amplification. In addition, use within a microfluidic device or platform as described herein achieves very high throughput, with droplets processed at rates in excess of 5000 droplets per second, enabling greater than $1 \times 10^6$ single-cell droplets to be formed and manipulated per hour.

Other examples of materials related to this invention include the formation of salts made by combination of various primary, secondary, or tertiary amines with PFPE carboxylic acid. The resulting amphiphilic structure could be useful as a stand-alone surfactant or a cosurfactant. Similarly, fluorinated materials with carboxylic acids other than Krytox PFPE could be used to form ionic fluorosurfactants with various amine containing compounds.

Alternative amine-containing compounds for use with the present invention include, but are not limited to, PEG-monoamine (molecular weights range from 200 to 1,000,000 or more), PEG-diamine (molecular weights range from 200 to 1,000,000 or more), Multifunctional PEG amines (e.g., branched or dendritic structures), other hydrophilic polymers terminated with amines. Sugars include, but are not limited to, Sugars, Peptides, Biomolecules, Ethanolamine or Alkyl amines—primary, secondary, or tertiary (e.g., triethylamine, trimethylamine, methylamine, ethylamine, butylamine)

Alternative fluorinated groups for use with the present invention include, but are not limited to, Krytox FSL and FSM (alternative molecular weights), Demnum PFPE materials, Fluolink PFPE materials or Fluorinated small molecules with carboxylic acids.

The data described herein show that the fluorosurfactants comprised of PEG amine salts provide better performance (compared to other fluorosurfactants) for stabilization of aqueous droplets in fluorinated oils in droplet-based microfluidics applications. These novel surfactants are useful either in combination with other surfactants or as a stand-alone surfactant system.

The invention can use pressure drive flow control, e.g., utilizing valves and pumps, to manipulate the flow of cells, particles, molecules, enzymes or reagents in one or more directions and/or into one or more channels of a microfluidic device. However, other methods may also be used, alone or in combination with pumps and valves, such as electro-osmotic flow control, electrophoresis and dielectrophoresis as described in Fulwyer, Science 156, 910 (1974); Li and Harrison, Analytical Chemistry 69, 1564 (1997); Fiedler, et al. Analytical Chemistry 70, 1909-1915 (1998) and U.S. Pat. No. 5,656,155. Application of these techniques according to the invention provides more rapid and accurate devices and methods for analysis or sorting, for example, because the sorting occurs at or in a sorting module that can be placed at or immediately after a detection module. This provides a shorter distance for molecules or cells to travel, they can move more rapidly and with less turbulence, and can more readily be moved, examined, and sorted in single file, i.e., one at a time.

Positive displacement pressure driven flow is a preferred way of controlling fluid flow and dielectrophoresis is a preferred way of manipulating droplets within that flow. The pressure at the inlet module can also be regulated by adjusting the pressure on the main and sample inlet channels, for example, with pressurized syringes feeding into those inlet channels. By controlling the pressure difference between the oil and water sources at the inlet module, the size and periodicity of the droplets generated may be regulated. Alternatively, a valve may be placed at or coincident to either the inlet module or the sample inlet channel connected thereto to control the flow of solution into the inlet module, thereby controlling the size and periodicity of the droplets. Periodicity and droplet volume may also depend on channel diameter, the viscosity of the fluids, and shear pressure. Examples of driving pressures and methods of modulating flow are as described in WO 2006/040551; U.S. Patent Application Publication No. 2009/0005254; WO 2006/040554; U.S. Patent Application Publication No. 2007/0184489; WO 2004/002627; U.S. Pat. No. 7,708,949; WO 2004/091763; U.S. Patent Application Publication No. 2006/0163385; WO 2005/021151; U.S. Patent Application Publication No. 2007/0003442; WO 2006/096571; U.S. Patent Application Publication No. 2009/0131543; WO 2007/089541; U.S. Patent Application Publication No. 2007/0195127; WO 2007/081385; U.S. Patent Application Publication No. 2010/0137163; WO 2007/133710; U.S. Patent Application Publication No. 2008/0014589; U.S. Pat. No. 6,540,895; U.S. Patent Application Publication No. 2001/0029983 and U.S. Patent Application Publication No. 2005/0226742

The microfluidic device of the present invention includes one or more inlet modules. An "inlet module" is an area of a microfluidic substrate device that receives molecules, cells, small molecules or particles for additional coalescence, detection and/or sorting. The inlet module can contain one or more inlet channels, wells or reservoirs, openings, and other features which facilitate the entry of molecules, cells, small molecules or particles into the substrate. A substrate may contain more than one inlet module if desired. Different sample inlet channels can communicate with the main channel at different inlet modules. Alternately, different sample inlet channels can communication with the main channel at the same inlet module. The inlet module is in fluid communication with the main channel. The inlet module generally comprises a junction between the sample inlet channel and the main channel such that a solution of a sample (i.e., a fluid containing a sample such as molecules, cells, small molecules (organic or inorganic) or particles) is introduced to the main channel and forms a plurality of droplets. The sample solution can be pressurized. The sample inlet channel can intersect the main channel such that the sample solution is introduced into the main channel at an angle perpendicular to a stream of fluid passing through the main channel. For example, the sample inlet channel and main channel intercept at a T-shaped junction; i.e., such that the sample inlet channel is perpendicular (90 degrees) to the main channel. However, the sample inlet channel can intercept the main channel at any angle, and need not introduce the sample fluid to the main channel at an angle that is perpendicular to that flow. The angle between intersecting channels is in the range of from about 60 to about 120 degrees. Particular exemplary angles are 45, 60, 90, and 120 degrees.

Embodiments of the invention are also provided in which there are two or more inlet modules introducing droplets of samples into the main channel. For example, a first inlet module may introduce droplets of a first sample into a flow of fluid in the main channel and a second inlet module may introduce droplets of a second sample into the flow of fluid in main channel, and so forth. The second inlet module is preferably downstream from the first inlet module (e.g., about 30 µm). The fluids introduced into the two or more different inlet modules can comprise the same fluid or the same type of fluid (e.g., different aqueous solutions). For example, droplets of an aqueous solution containing an enzyme are introduced into the main channel at the first inlet module and droplets of aqueous solution containing a substrate for the enzyme are introduced into the main channel at the second inlet module. Alternatively, the droplets introduced at the different inlet modules may be droplets of different fluids which may be compatible or incompatible. For example, the different droplets may be different aqueous solutions, or droplets introduced at a first inlet module may be droplets of one fluid (e.g., an aqueous solution) whereas droplets introduced at a second inlet module may be another fluid (e.g., alcohol or oil).

An important element in making libraries utilizing the microfluidic device of the present invention is to include features in the channels of the device to remove particles that may effect the microfluidic system. When emulsions are injected or re-injected onto a microfluidic device, they carry contaminants that collect at the nozzle and either clog the nozzle and/or induce uncontrolled coalescence up to the complete shredding of the emulsion. Debris/contaminants include small debris, such as dust or TCS, fibers, goop (glue and/or surfactant) and large debris such as PDMS skins/shavings. In one example, the present invention provides a post trap for large debris, a pocket trap for small debris, a serpentine trap for fibers and a step trap for large droplets/debris. EAP filters work well to filter out the contaminants.

The filter system filters out these contaminants and most importantly traps the contaminants out of the main pathway and allow the droplets to pass by so the contaminants cannot induce uncontrolled coalescence. The present invention comprises two distinct parts that specifically address two different scales. The first filters contaminants that are larger than the droplet size. The second filters contaminants that are smaller than the droplet and nozzle sizes. The large contaminants are easily trapped but are responsible for inducing uncontrolled coalescence, the small contaminants tend to stick to the nozzle and most probably induce wetting that results in the shredding of the emulsion.

To address the issue of large contaminants, a triangular shape filter is used that contains an internal-collection channel and smaller lateral channels connected to the internal-collection channel with a specific angle. On each side of the triangle are pockets to collect the contaminants that have been deflected by the triangle and directed there by the flow of the droplets due to the specific angle of the filter. In addition, the collection pockets are connected to a channel of high hydrodynamic resistance so that some of the flow will still go through and maintain the contaminants in the collection pockets. The lateral collection channels are located at a stepwise transition between a shallow layer and a deep layer. In one example, he droplets are collected in the Droplet Collection Channel through the lateral angled channels. The contaminants are deflected toward the Contaminant Collection Pocket because of the triangular shape and the droplet flow. Because of the use of high resistance channel for the Contaminants Collection Pockets, the droplets go through them only marginally, but enough to force the trapped contaminants to stay there.

To address the issue of the small contaminants, a series of posts are used, each one being offset by a half-period to the adjacent ones. This geometry intends to create a region of null-recirculation flow at the tip of each post due to the symmetry and contaminants are trapped in that region. In addition, the posts have an indentation to both increase the effect of the flow pattern described above and to trap the contaminants so that they are out of the way of the droplets. The posts can be designed just with an indentation or with a flow-through restriction of high hydrodynamic resistance so that the contaminants will be directed and trapped deep in the structure. The symmetrical design creates a region where there is almost no flow, in this region creates the conditions to trap the contaminants that are smaller than the droplets. The droplets follow the main flow because of the high hydrodynamic resistance conditions. The posts on one side of the channel have a flow-through to ensure that the contaminants stay trapped there; on the other side the posts have only an indentation. Several series of these posts, offset by half of a period are used to increase both the filter capacity and the odds of trapping any given contaminant.

Particular design embodiments of the microfluidic device described herein allow for a more reproducible and controllable interdigitation of droplets of specific liquids followed by pair-wise coalescence of these droplets, described in further detail herein. The droplet pairs can contain liquids of different compositions and/or volumes, which would then combine to allow for a specific reaction to be investigated. The pair of droplets can come from any of the following: (i) two continuous aqueous streams and an oil stream; (ii) a continuous aqueous stream, an emulsion stream, and an oil stream, or (iii) two emulsion streams and an oil stream. The term "interdigitation" as used herein means pairing of droplets from separate aqueous streams, or from two separate inlet nozzles, for eventual coalescence.

Various nozzle designs enhance the interdigitation of droplets and further improves coalescence of droplets due to the better control of the interdigitation and smaller distance between pairs of droplets. The greater control over interdigitation allows for a perfect control over the frequency of either of the droplets. To obtain the optimum operation, the spacing between droplets and coupling of the droplets can be adjusted by adjusting flow of any of the streams, viscosity of the streams, nozzle design (including orifice diameter, the channel angle, and post-orifice neck of the nozzle). Examples of preferred nozzle designs are as described in WO 2007/081385; U.S. Patent Application Publication No. 2010/0137163; WO 2008/063227 and U.S. Patent Application Publication No. 2008/0003142.

A device of the invention can include a sample solution reservoir or well or other apparatus for introducing a sample to the device, at the inlet module, which is typically in fluid communication with an inlet channel. Reservoirs and wells used for loading one or more samples onto the microfluidic device of the present invention, include but are not limited to, syringes, cartridges, vials, eppendorf tubes and cell culture materials (e.g., 96 well plates). A reservoir may facilitate introduction of molecules or cells into the device and into the sample inlet channel of each analysis unit.

The microfluidic device of the present invention also includes one or more coalescence modules. A "coalescence module" is within or coincident with at least a portion of the main channel at or downstream of the inlet module where molecules, cells, small molecules or particles comprised within droplets are brought within proximity of other droplets comprising molecules, cells, small molecules or particles and where the droplets in proximity fuse, coalesce or combine their contents. The coalescence module can also include an apparatus, for generating an electric force.

The electric force exerted on the fluidic droplet may be large enough to cause the droplet to move within the liquid. In some cases, the electric force exerted on the fluidic droplet may be used to direct a desired motion of the droplet within the liquid, for example, to or within a channel or a microfluidic channel (e.g., as further described herein), etc.

The electric field can be generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments. As used herein, "integral" means that portions of the components integral to each other are joined in such a way that the components cannot be in manually separated from each other without cutting or breaking at least one of the components.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof.

Preferred electrodes and patterned electrically conductive layers are described in WO 2007/081385; U.S. Patent Application Publication No. 2010/0137163; WO 2008/063227 and U.S. Patent Application Publication No. 2008/0003142 and can be associated with any module of the device (inlet module, coalescence module, mixing module, delay module, detection module and sorting module) to generate dielectric or electric forces to manipulate and control the droplets and their contents.

Effective control of uncharged droplets within microfluidic devices can require the generation of extremely strong dielectric field gradients. The fringe fields from the edges of a parallel plate capacitor can provide an excellent topology to form these gradients. The microfluidic device according to the present invention can include placing a fluidic channel between two parallel electrodes, which can result in a steep electric field gradient at the entrance to the electrodes due to edge effects at the ends of the electrode pair. Placing these pairs of electrodes at a symmetric channel split can allow precise bi-directional control of droplet within a device. Using the same principle, only with asymmetric splits, can allow single ended control of the droplet direction in the same manner. Alternatively, a variation on this geometry will allow precise control of the droplet phase by shifting.

Dielectrophoresis is believed to produce movement of dielectric objects, which have no net charge, but have regions that are positively or negatively charged in relation to each other. Alternating, non-homogeneous electric fields in the presence of droplets and/or particles, such as cells or molecules, cause the droplets and/or particles to become electrically polarized and thus to experience dielectrophoretic forces. Depending on the dielectric polarizability of the particles and the suspending medium, dielectric particles will move either toward the regions of high field strength or low field strength. For example, the polarizability of living cells depends on their composition, morphology, and phenotype and is highly dependent on the frequency of the applied electrical field. Thus, cells of different types and in different physiological states generally possess distinctly different dielectric properties, which may provide a basis for cell separation, e.g., by differential dielectrophoretic forces. Likewise, the polarizability of droplets also depends upon their size, shape and composition. For example, droplets that contain salts can be polarized. According to formulas provided in Fiedler, et al. Analytical Chemistry 70, 1909-1915 (1998), individual manipulation of single droplets requires field differences (inhomogeneities) with dimensions close to the droplets.

The term "dielectrophoretic force gradient" means a dielectrophoretic force is exerted on an object in an electric field provided that the object has a different dielectric constant than the surrounding media. This force can either pull the object into the region of larger field or push it out of the region of larger field. The force is attractive or repulsive depending respectively on whether the object or the surrounding media has the larger dielectric constant.

Manipulation is also dependent on permittivity (a dielectric property) of the droplets and/or particles with the suspending medium. Thus, polymer particles, living cells show negative dielectrophoresis at high-field frequencies in water. For example, dielectrophoretic forces experienced by a latex sphere in a 0.5 MV/m field (10 V for a 20 micron electrode gap) in water are predicted to be about 0.2 piconewtons (pN) for a 3.4 micron latex sphere to 15 pN for a 15 micron latex sphere (Fiedler, et al. Analytical Chemistry, 70, 1909-1915 (1998)). These values are mostly greater than the hydrodynamic forces experienced by the sphere in a stream (about 0.3 pN for a 3.4 micron sphere and 1.5 pN for a 15 micron sphere). Therefore, manipulation of individual cells or particles can be accomplished in a streaming fluid, such as in a cell sorter device, using dielectrophoresis. Using conventional semiconductor technologies, electrodes can be microfabricated onto a substrate to control the force fields in a microfabricated sorting device of the invention. Dielectrophoresis is particularly suitable for moving objects that are electrical conductors. The use of AC current is preferred, to prevent permanent alignment of ions. Megahertz frequencies are suitable to provide a net alignment, attractive force, and motion over relatively long distances. See U.S. Pat. No. 5,454,472.

The electric field generator can be constructed and arranged (e.g., positioned) to create an electric field applicable to the fluid of at least about 0.01 V/micrometer, and, in some cases, at least about 0.03 V/micrometer, at least about 0.05 V/micrometer, at least about 0.08 V/micrometer, at least about 0.1 V/micrometer, at least about 0.3 V/micrometer, at least about 0.5 V/micrometer, at least about 0.7 V/micrometer, at least about 1 V/micrometer, at least about 1.2 V/micrometer, at least about 1.4 V/micrometer, at least about 1.6 V/micrometer, or at least about 2 V/micrometer. In some embodiments, even higher electric field intensities may be used, for example, at least about 2 V/micrometer, at least about 3 V/micrometer, at least about 5 V/micrometer, at least about 7 V/micrometer, or at least about 10 V/micrometer or more.

As described, an electric field may be applied to fluidic droplets to cause the droplets to experience an electric force. The electric force exerted on the fluidic droplets may be, in some cases, at least about $10^{-16}$ N/micrometer$^3$. In certain cases, the electric force exerted on the fluidic droplets may be greater, e.g., at least about $10^{-15}$ N/micrometer$^3$, at least about $10^{-14}$ N/micrometer$^3$, at least about $10^{-13}$ N/micrometer$^3$, at least about $10^{-12}$ N/micrometer$^3$, at least about $10^{-11}$ N/micrometer$^3$, at least about $10^{-10}$ N/micrometer$^3$, at least about $10^{-9}$ N/micrometer$^3$, at least about $10^{-8}$ N/micrometer$^3$, or at least about $10^{-7}$ N/micrometer$^3$ or more. The electric force exerted on the fluidic droplets, relative to the surface area of the fluid, may be at least about $10^{-15}$ N/micrometer$^2$, and in some cases, at least about $10^{-14}$ N/micrometer$^2$, at least about $10^{-13}$ N/micrometer$^2$, at least about $10^{-12}$ N/micrometer$^2$, at least about $10^{-11}$ N/micrometer$^2$, at least about $10^{-10}$ N/micrometer$^2$, at least about $10^{-9}$ N/micrometer$^2$, at least about $10^{-8}$ N/micrometer$^2$, at least about $10^{-7}$ N/micrometer$^2$, or at least about $10^{-6}$ N/micrometer$^2$ or more. In yet other embodiments, the electric force exerted on the fluidic droplets may be at least about $10^{-9}$ N, at least about $10^{-8}$ N, at least about $10^{-7}$ N, at least about $10^{-6}$ N, at least about $10^{-5}$ N, or at least about $10^{-4}$ N or more in some cases.

In preferred embodiments described herein, droplet coalescence is presently carried out by having two droplet forming nozzles emitting droplets into the same main channel. The size of the nozzles allow for one nozzle to form a large drop that fills the exhaust line while the other nozzle forms a drop that is smaller than the first. The smaller droplet is formed at a rate that is less than the larger droplet rate, which insures that at most one small droplet is between big droplets. Normally, the small droplet will catch up to the larger one over a relatively short distance, but sometimes the recirculation zone behind the large drop causes the small drop to separate from the large drop cyclically. In addition, the small drop occasionally does not catch up with the large one over the distance between the nozzles and the coalescing electrodes. Thus, in some situations is a need for a more robust coalescence scheme.

Geometric alterations in the coalescence module can create a more robust, reliable coalescence or fusing of droplets over a wider range of sizes and flows. The solution to improve the performance is to place an expansion in the main channel between the electrodes. Optionally, a small constriction (neckdown) just before this expansion can be used to better align the droplets on their way into the coalescence point. This optional neckdown can help center the small droplet in the channel stream lines, reducing the chance that it will flow around the larger droplet prior to coalescing in the expansion. The electrode pair may be placed on either one side of the channel or on both sides.

The expansion in the coalescing region allows for a dramatic catching up of the small drop to the large drop, as shown through micrographs taken on an operating device. The volume of the expansion is big enough to slow the large droplet down so that the small drop always catches up to the large drop, but doesn't allow the next large drop to catch up and make contact with the pair to be coalesced. The electrodes allow for coalescence to take place when the drops are in contact with each other and passing through the field gradient.

The microfluidic device of the present invention can also include one or more detection modules. A "detection module" is a location within the device, typically within the main channel where molecules, cells, small molecules or particles are to be detected, identified, measured or interrogated on the basis of at least one predetermined characteristic. The molecules, cells, small molecules or particles can be examined one at a time, and the characteristic is detected or measured optically, for example, by testing for the presence or amount of a reporter. For example, the detection module is in communication with one or more detection apparatuses. The detection apparatuses can be optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at the sorting module. However, other detection techniques can also be employed The terms "detecting" or "determining," as used herein, generally refers to the analysis or measurement of a species, for example, quantitatively or qualitatively, and/or the detection of the presence or absence of the species. "Detecting or "determining" may also refer to the analysis or measurement of an interaction between two or more species, for example, quantitatively or qualitatively, or by detecting the presence or absence of the interaction. Examples of suitable techniques include, but are not limited to, spectroscopy such as infrared, absorption, fluorescence, UV/visible, FTIR ("Fourier Transform Infrared Spectroscopy"), or Raman; gravimetric techniques; ellipsometry; piezoelectric measurements; immunoassays; electrochemical measurements; optical measurements such as optical density measurements; circular dichroism; light scattering measurements such as quasielectric light scattering; polarimetry; refractometry; or turbidity measurements as described further herein.

A detection module is within, communicating or coincident with a portion of the main channel at or downstream of the inlet module and, in sorting embodiments, at, proximate to, or upstream of, the sorting module or branch point. The sorting module may be located immediately downstream of the detection module or it may be separated by a suitable distance consistent with the size of the molecules, the channel dimensions and the detection system. Precise boundaries for the detection module are not required, but are preferred.

One or more detections sensors and/or processors may be positioned to be in sensing communication with the fluidic droplet. "Sensing communication," as used herein, means that the sensor may be positioned anywhere such that the fluidic droplet within the fluidic system (e.g., within a channel), and/or a portion of the fluidic system containing the fluidic droplet may be sensed and/or determined in some fashion. For example, the sensor may be in sensing communication with the fluidic droplet and/or the portion of the fluidic system containing the fluidic droplet fluidly, optically or visually, thermally, pneumatically, electronically, or the like. The sensor can be positioned proximate the fluidic system, for example, embedded within or integrally connected to a wall of a channel, or positioned separately from the fluidic system but with physical, electrical, and/or optical communication with the fluidic system so as to be able to sense and/or determine the fluidic droplet and/or a portion of the fluidic system containing the fluidic droplet (e.g., a channel or a microchannel, a liquid containing the fluidic droplet, etc.). For example, a sensor may be free of any physical connection with a channel containing a droplet, but may be positioned so as to detect electromagnetic radiation arising from the droplet or the fluidic system, such as infrared, ultraviolet, or visible light. The electromagnetic radiation may be produced by the droplet, and/or may arise from other portions of the fluidic system (or externally of the fluidic system) and interact with the fluidic droplet and/or the portion of the fluidic system containing the fluidic droplet in such as a manner as to indicate one or more characteristics of the fluidic droplet, for example, through absorption, reflection, diffraction, refraction, fluorescence, phosphorescence, changes in polarity, phase changes, changes with respect to time, etc. As an example, a laser may be directed towards the fluidic droplet and/or the liquid surrounding the fluidic droplet, and the fluorescence of the fluidic droplet and/or the surrounding liquid may be determined "Sensing communication," as used herein may also be direct or indirect. As an example, light from the fluidic droplet may be directed to a sensor, or directed first through a fiber optic system, a waveguide, etc., before being directed to a sensor.

Non-limiting examples of detection sensors useful in the invention include optical or electromagnetically-based systems. For example, the sensor may be a fluorescence sensor (e.g., stimulated by a laser), a microscopy system (which may include a camera or other recording device), or the like. As another example, the sensor may be an electronic sensor, e.g., a sensor able to determine an electric field or other electrical characteristic. For example, the sensor may detect capacitance, inductance, etc., of a fluidic droplet and/or the portion of the fluidic system containing the fluidic droplet. In some cases, the sensor may be connected to a processor, which in turn, cause an operation to be performed on the fluidic droplet, for example, by sorting the droplet.

Characteristics determinable with respect to the droplet and usable in the invention can be identified by those of ordinary skill in the art. Non-limiting examples of such characteristics include fluorescence, spectroscopy (e.g., optical, infrared, ultraviolet, etc.), radioactivity, mass, volume, density, temperature, viscosity, pH, concentration of a substance, such as a biological substance (e.g., a protein, a nucleic acid, etc.), or the like.

A corresponding signal is then produced, for example indicating that "yes" the characteristic is present, or "no" it is not. The signal may correspond to a characteristic qualitatively or quantitatively. That is, the amount of the signal can be measured and can correspond to the degree to which a characteristic is present. For example, the strength of the signal may indicate the size of a molecule, or the potency or amount of an enzyme expressed by a cell, or a positive or negative reaction such as binding or hybridization of one molecule to another, or a chemical reaction of a substrate catalyzed by an enzyme. In response to the signal, data can be collected and/or a control system in the sorting module, if present, can be activated to divert a droplet into one branch channel or another for delivery to the collection module or waste module. Thus, in sorting embodiments, molecules or cells within a droplet at a sorting module can be sorted into an appropriate branch channel according to a signal produced by the corresponding examination at a detection module. The means of changing the flow path can be accomplished through mechanical, electrical, optical, or some other technique as described herein.

A preferred detector is an optical detector, such as a microscope, which may be coupled with a computer and/or other image processing or enhancement devices to process images or information produced by the microscope using known techniques. For example, molecules can be analyzed and/or sorted by size or molecular weight. Enzymes can be analyzed and/or sorted by the extent to which they catalyze chemical reaction of a substrate (conversely, substrate can be analyzed and/or sorted by the level of chemical reactivity catalyzed by an enzyme). Cells can be sorted according to whether they contain or produce a particular protein, by using an optical detector to examine each cell for an optical indication of the presence or amount of that protein. The protein may itself be detectable, for example by a characteristic fluorescence, or it may be labeled or associated with a reporter that produces a detectable signal when the desired protein is present, or is present in at least a threshold amount. There is no limit to the kind or number of characteristics that can be identified or measured using the techniques of the invention, which include without limitation surface characteristics of the cell and intracellular characteristics, provided only that the characteristic or characteristics of interest for sorting can be sufficiently identified and detected or measured to distinguish cells having the desired characteristic(s) from those which do not. For example, any label or reporter as described herein can be used as the basis for analyzing and/or sorting molecules or cells, i.e. detecting molecules or cells to be collected.

As described herein, the biological/chemical entity to be analyzed may itself be detectable, for example by a characteristic fluorescence, or it may be labeled or associated with a reporter that produces a detectable signal when the desired protein is present, or is present in at least a threshold amount.

Luminescent colloidal semiconductor nanocrystals called quantum dots or q-dots (QD) are inorganic fluorophores that have the potential to circumvent some of the functional limitations encountered by organic dyes. In particular, CdSe—ZnS core-shell QDs exhibit size-dependent tunable photoluminescence (PL) with narrow emission bandwidths (FWHM ~30 to 45 nm) that span the visible spectrum and broad absorption bands. These allow simultaneous excitation of several particle sizes (colors) at a common wavelength. This, in turn, allows simultaneous resolution of several colors using standard instrumentation. CdSe—ZnS QDs also have high quantum yields, are resistant to photodegradation, and can be detected optically at concentrations comparable to organic dyes.

Quantum dots are nano-scale semiconductors typically consisting of materials such as crystalline cadmium selenide. The term 'q-dot' emphasizes the quantum confinement effect of these materials, and typically refers to fluorescent nanocrystals in the quantum confined size range. Quantum confinement refers to the light emission from bulk (macroscopic) semiconductors such as LEDs which results from exciting the semiconductor either electrically or by shining light on it, creating electron-hole pairs which, when they recombine, emit light. The energy, and therefore the wavelength, of the emitted light is governed by the composition of the semiconductor material. If, however, the physical size of the semiconductor is considerably reduced to be much smaller than the natural radius of the electron-hole pair (Bohr radius), additional energy is required to "confine" this excitation within the nanoscopic semiconductor structure leading to a shift in the emission to shorter wavelengths. Three different q-dots in several concentrations each can be placed in a microdroplet, and can then be used with a microfluidic device to decode what is in the drop. The Q-dot readout extension to the fluorescence station can be incorporated into the design of the microfluidic device. A series of dichroic beamsplitters, emission filters, and detectors can be stacked onto the system, allowing measurement of the required five emission channels (two fluorescence polarization signals and three q-dot bands).

Fluorescence Polarization (FP) detection technology enables homogeneous assays suitable for high throughput screening assays in the Drug Discovery field. The most common label in the assays is fluorescein. In FP-assay the fluorophore is excited with polarized light. Only fluorophores parallel to the light absorb and are excited. The excited state has a lifetime before the light emission occurs. During this time the labeled fluorophore molecule rotates and the polarization of the light emitted differs from the excitation plane. To evaluate the polarization two measurements are needed: the first using a polarized emission filter parallel to the excitation filter (S-plane) and the second with a polarized emission filter perpendicular to the excitation filter (P-plane). The Fluorescence Polarization response is given as mP (milli-Polarization level) and is obtained from the equation:

$$\text{Polarization (mP)} = 1000 * (S - G*P)/(S + G*P)$$

Where S and P are background subtracted fluorescence count rates and G (grating) is an instrument and assay dependent factor.

The rotational speed of a molecule is dependent on the size of the molecule, temperature and viscosity of the solution. Fluorescein has a fluorescence lifetime suitable for the rotation speeds of molecules in bio-affinity assays like receptor-ligand binding assays or immunoassays of haptens. The basic principle is that the labeled compound is small and rotates rapidly (low polarization). When the labeled compound binds to the larger molecule, its rotation slows down considerably (polarization changes from low to high polarization). Thus, FP provides a direct readout of the extent of tracer binding to protein, nucleic acids, and other biopolymers.

Fluorescence polarization technology has been used in basic research and commercial diagnostic assays for many decades, but has begun to be widely used in drug discovery only in the past six years. Originally, FP assays for drug discovery were developed for single-tube analytical instruments, but the technology was rapidly converted to high-throughput screening assays when commercial plate readers with equivalent sensitivity became available. These assays include such well-known pharmaceutical targets such as kinases, phosphatases, proteases, G-protein coupled receptors, and nuclear receptors. Other homogeneous technologies based on fluorescence intensity have been developed. These include energy transfer, quenching, and enhancement assays. FP offers several advantages over these. The assays are usually easier to construct, since the tracers do not have to respond to binding by intensity changes. In addition, only one tracer is required and crude receptor preparations may be utilized. Furthermore, since FP is independent of intensity, it is relatively immune to colored solutions and cloudy suspensions. FP offers several advantages in the area of instrumentation. Because FP is a fundamental property of the molecule, and the reagents are stable, little or no standardization is required. FP is relatively insensitive to drift in detector gain settings and laser power.

The dyes chosen for FP are commonly used in most cell- and enzyme-based assays and are designed not to overlap significantly with the q-dots. The dyes are evaluated both independently and together with the q-dots (at first off-instrument) to assess the cross-talk. Preferably, the liquid q-dot labels are read outside a spectral wavelength band currently used in FACS analysis and sorting (i.e., the dyes flourescein, Cy3, Cy5, etc). This permits the use of currently-available assays (dependent on these dyes). Using specific q-dots, crosstalk is minimized.

Accordingly, the present invention provides methods to label droplets and/or nanoreactors formed on a microfluidic device by using only a single dye code to avoid cross-talk with other dyes during FP. Additionally, the present invention provides methods to create FP dye codes to label compounds contained within liquids (including droplets and/or nanoreactors) where the compound is designed to be differentiated by FP on a microfluidic device. In this manner, dye codes having the same color, absorption, and emission could be used to label compounds within liquids.

In one aspect, the present invention is directed to the use of fluorescence polarization to label liquids. Droplets can be labeled using several means. These labeling means include, but are not limited to, the use of different dyes, quantum dots, capacitance, opacity, light scattering, fluorescence intensity (FI), fluorescence lifetime (FL), fluorescence polarization (FP), circular dichroism (CD), fluorescence correlation and combinations of all of these previous labeling means. The following disclosure describes the use of FP and FI as a means to label droplets on a microfluidic device. In addition, the use of FL as a means to adjust the overall FP of a solution, and by varying the concentration of the total FI, to create a 2-dimensional encoding scheme is demonstrated.

In general, molecules that take up more volume will tumble slower than a smaller molecule coupled to the same fluorophore. FP is independent of the concentration of the dye; liquids can have vastly different concentrations of FITC in them yet still have identical FP measurements.

In a preferred embodiment, a FP dye is an organic dye that does not interfere with the assay dye is used. Furthermore, since the total intensity of the FP dye can be quantified, a second dimension in which to label the droplet is provided. Thus, one can exploit the differences in FP to create an encoding scheme of dye within a liquid solution, including droplets. Examples of ways to exploit the differences in FP are described in WO 2007/081385; U.S. Patent Application Publication No. 2010/0137163; WO 2008/063227 and U.S. Patent Application Publication No. 2008/0003142. In a single dimension, FP can be used to create an encoding scheme. However, the present invention can also use Fluorescence Intensity (FI) of the overall solution to create even more labels in a second dimension. Interestingly, the differences of the fluorescence lifetime (FL) of two dyes with spectral overlap in the detected emission wavelength to change the overall FP of the combined solution can also be exploited.

Although the use of multiple compounds to which a dye molecule is attached to span a range of FP can be utilized, it is also possible to span the range using a high and low molecular weight compound set. For example, a dye can be attached to a large compound (for example streptavidin) and kept at a fixed concentration, to which a smaller compound (for example, a free dye molecule) would be titrated into the same solution. The FP of the solution can be adjusted to be in discernable increments from the value of the large molecule to somewhere slightly greater than the FP of the smaller molecule. The [total] dye intensity can be varied by varying the concentration of the mixture of the two dye-attached compounds. By varying total dye concentration and the FP, two dimensions can be used to generate the FP dye codes (FPcodes). Accordingly, many FPcodes can be generated using only two compounds.

This could also include use of large fluorescent proteins such as GFP and the phycobiliproteins combined with a smaller molecule.

In another aspect, the present invention is directed labeling solids using properties other than dye emission and dye concentration. In one embodiment the solid can include, for example, a bead or location on a solid support or chip. As demonstrated above for liquids, FI and FL can be two of many dimensions of characteristics used as labels. By way of non-limiting example, it is possible to use two dyes with different FL to change the overall FP for a solid such as a bead or other mobile solid support.

In another embodiment, a linker can be used to couple the dye to the bead. The linker can be varied so as to allow the dye to have differing degrees of freedom in which to rotate (i.e., tumble). Varying the linker in this manner can change the FP of the attached dye, which in unique combinations can be used as a label. In some embodiments, the beads can be swollen in organic solvent and the dyes held in place by hydrophobic forces. In this case, the FP, FI, FL methods described above for liquid labeling can also be used as a means for labeling the beads. A quenching molecule can also be used to change the characteristics of a dye. Such quenching can be continuous or brought about through the interaction of a molecule, such as a peptide or nucleic acid linker, with differing means of bringing molecules together depending on the strength of linker-internal interaction (e.g., a nucleotide stem loop structure of varying lengths).

The reactions analyzed on the virtual, random and non-random arrays (discussed briefly below) can be also increased beyond the two (cy3 and cy5 intensities) commonly used for multiplexing. For example, different FP, FI, etc can be used as a read-out.

Random array decoding: Beads of the prior art use one or more pre-attached oligonucleotide-coupled beads that are held in place in a fiber-optic faceplate (for example, those used by Illiumina). The oligos on the beads are decoded using sequential hybridization of a labeled complementary oligo. The assay of the prior art uses a separate oligonucleotide complementary zipcode ('Illumacode') attached to each type of bead.

The invention described herein is superior to the methods of the prior art in that the FP, FI, FL-labeled bead or mobile solid support can be placed into a random array (e.g., a chip as manufactured by Illumina) and the FP, FI, FL used to decode the bead. The FP, FI, FL of the bead can be decoded before using the chip and the different beads 'mapped' as to their specific locations. Alternatively, the bead can be decoded during attachment of the assay read-out. Significantly, the methods described by the present invention can be used to pre-determine the location of each bead-type either before, or during analysis.

Virtual array decoding: Methods of the prior art use 2 lasers and 3 detectors to differentiate a set of 100 bead-types. The beads-types are differentiated by the FI of two different dyes present in 1 of 10 concentrations (per dye) contained within the bead, and the assay detector is used to measure fluorescein concentration on the bead. The dyes, which are added to organic-solvent swollen beads, are not directly attached to the beads, but remain held within the bead by hydrophobic forces.

Using the methods of the present invention as described herein, a second detector to the machines of the prior art used to measure FP can be added, thereby adding a third dimension and extending the encoding scheme beyond the 100 available in the prior art.

Non-random array decoding: In chips of the prior art (such as those used by Affymetrix) oligonucleotides are synthesized directly on the chip. Decoding is simply a matter of knowing the location of the assay on the chip.

The methods as described herein can be advantageously used in conjunction with such chips to increase the number of things that can be simultaneously analyzed (i.e., multiplexed) on the chip. By way of non-limiting example, Cy3, Cy5, FL and FP can be used as analysis markers for hybridization reactions.

The present invention can include also provides methods for labeling micro or nano-sized droplets using Radio Frequency Identification (RFID). RFID tags can improve the identification of the contents within the droplets. Preferably, the droplets are utilized within a microfluidic device.

RFID is an automatic identification method, relying on storing and remotely retrieving data using devices called RFID tags or transponders. An RFID tag is an object that can be attached to or incorporated into a product, animal, or person for the purpose of identification using radio waves. Chip-based RFID tags contain silicon chips and antennae. Passive tags require no internal power source, whereas active tags require a power source. Hitachi has "powder" 0.05 mm×0.05 mm RFID chips. The new chips are 64 times smaller than the previous record holder, the 0.4 mm×0.4 mm mu-chips, and nine times smaller than Hitachi's last year prototype, and have room for a 128-bit ROM that can store a unique 38-digit ID number.

In one embodiment, a solution containing RFID tags are emulsified into droplets and are used as a label for the identification of the material within the droplet solution. Applications include, but are not limited to; genetics, genomics, proteomics, chemical synthesis, biofuels, and others.

Lasers

To detect a reporter or determine whether a molecule, cell or particle has a desired characteristic, the detection module may include an apparatus for stimulating a reporter for that characteristic to emit measurable light energy, e.g., a light source such as a laser, laser diode, light emitting diode (LED), high-intensity lamp, (e.g., mercury lamp), and the like. Where a lamp is used, the channels are preferably shielded from light in all regions except the detection module. Where a laser is used, the laser can be set to scan across a set of detection modules from different analysis units. In addition, laser diodes or LED's may be microfabricated into the same chip that contains the analysis units. Alternatively, laser diodes or LED's may be incorporated into a second chip (i.e., a laser diode chip) that is placed adjacent to the analysis or microchip such that the laser light from the diodes shines on the detection module(s).

An integrated semiconductor laser and/or an integrated photodiode detector can be included on the substrate in the vicinity of the detection module. This design provides the advantages of compactness and a shorter optical path for exciting and/or emitted radiation, thus minimizing distortion and losses.

Fluorescence produced by a reporter is excited using a laser beam focused on molecules (e.g., DNA, protein, enzyme or substrate) or cells passing through a detection region. Fluorescent reporters can include, but are not limited to, rhodamine, fluorescein, Texas red, Cy 3, Cy 5, phycobiliprotein (e.g., phycoerythrin), green fluorescent protein (GFP), YOYO-1 and PicoGreen. In molecular fingerprinting applications, the reporter labels can be fluorescently labeled single nucleotides, such as fluorescein-dNTP, rhodamine-dNTP, Cy3-dNTP, etc.; where dNTP represents dATP, dTTP, dUTP or dCTP. The reporter can also be chemically-modified single nucleotides, such as biotin-dNTP. The reporter can be fluorescently or chemically labeled amino acids or antibodies (which bind to a particular antigen, or fragment thereof, when expressed or displayed by a cell or virus).

The device can analyze and/or sort cells based on the level of expression of selected cell markers, such as cell surface markers, which have a detectable reporter bound thereto, in a manner similar to that currently employed using fluorescence-activated cell sorting (FACS) machines. Proteins or other characteristics within a cell, and which do not necessarily appear on the cell surface, can also be identified and used as a basis for sorting. The device can also determine the size or molecular weight of molecules such as polynucleotides or polypeptides (including enzymes and other proteins) or fragments thereof passing through the detection module. Alternatively, the device can determine the presence or degree of some other characteristic indicated by a reporter. If desired, the cells, particles or molecules can be sorted based on this analysis. The sorted cells, particles or molecules can be collected from the outlet channels in collection modules (or discarded in wasted modules) and used as needed. The collected cells, particles or molecules can be removed from the device or reintroduced to the device for additional coalescence, analysis and sorting.

As used herein, a "processor" or a "microprocessor" is any component or device able to receive a signal from one or more sensors, store the signal, and/or direct one or more responses (e.g., as described above), for example, by using a mathematical formula or an electronic or computational circuit. The signal may be any suitable signal indicative of the environmental factor determined by the sensor, for example a pneumatic signal, an electronic signal, an optical signal, a mechanical signal, etc.

The device of the present invention can comprise features, such as integrated metal alloy components and/or features patterned in an electrically conductive layer, for detecting droplets by broadcasting a signal around a droplet and picking up an electrical signal in proximity to the droplet.

The device of the present invention also comprises the use of beads and methods for analyzing and sorting beads (i.e., bead reader device). The device can read and either sort or not sort droplets containing one or more of a set of two or more beads. Each bead can be differentiated from each other bead within a set. Beads can be separated by several tags including, but not limited to, quantum dyes, fluorescent dyes, ratios of fluorescent dyes, radioactivity, radio-tags, etc. For example, a set of beads containing a ratio of two dyes in discrete amounts with an apparatus for detecting and differentiating beads containing one discrete ratio from the other beads in this set having a different ratio of the two dyes. The microfluidic device can include paramagnetic beads. The paramagnetic beads can introduce and remove chemical components from droplets using droplet coalescence and breakup events. The paramagnetic beads can also be used for sorting droplets.

The present invention provides methods of screening molecular libraries on beads through limited-dilution-loading and then chemical or optical release inside of droplets. Provided are methods for chemical synthesis on a bead and releasing said chemical attached to the bead using a releasing means (chemical, UV light, heat, etc) within a droplet, and then combining a second droplet to the first droplet for further manipulation. For example, tea-bag synthesis of chemicals on a bead simultaneously with a means for identifying said bead (using, for example, a mass spec tag). Using the resulting mixed-chemistry beads in a droplet within a fluid flow, and exposing the beads to UV light to release the chemical synthesized from the bead into the droplet environment. Combining the droplet containing the released chemical with a droplet containing a cell, and performing a cell-based assay. Sorting droplets having the desired characteristics (for example, turn on of a reporter gene), and then analyzing the sorted beads using mass spectroscopy.

The device of the present invention can comprise column separation prior to bead sorting. A device containing a channel loaded with a separating means for chromatographically sorting the sample prior to droplet formation. Such separating means could include size, charge, hydrophobicity, atomic mass, etc. The separating can be done isocratic or by use of a means for generating a gradient chemically, (for example using salt or hydrophobicity), electrically, by pressure, or etc. For example, a channel is preloaded with Sepharose size exclusion media. A sample is loaded at one end, and the droplets are formed at an opposing end. The sample separates by size prior to becoming incorporated within a droplet.

The microfluidic device of the present invention can further include one or more sorting modules. A "sorting module" is a junction of a channel where the flow of molecules, cells, small molecules or particles can change direction to enter one or more other channels, e.g., a branch channel for delivery to an outlet module (i.e., collection or waste module), depending on a signal received in connection with an examination in the detection module. Typically, a sorting module is monitored and/or under the control of a detection module, and therefore a sorting module may "correspond" to such detection module. The sorting region is in communication with and is influenced by one or more sorting apparatuses. A sorting apparatus comprises techniques or control systems, e.g., dielectric, electric, electro-osmotic, (micro-) valve, etc. A control system can employ a variety of sorting techniques to change or direct the flow of molecules, cells, small molecules or particles into a predetermined branch channel. A "branch channel" is a channel which is in communication with a sorting region and a main channel. The main channel can communicate with two or more branch channels at the sorting module or "branch point", forming, for example, a T-shape or a Y-shape. Other shapes and channel geometries may be used as desired. Typically, a branch channel receives molecules, cells, small molecules or particles depending on the molecule, cells, small molecules or particles characteristic of interest as detected by the detection module and sorted at the sorting module. A branch channel can have an outlet module and/or terminate with a well or reservoir to allow collection or disposal (collection module or waste module, respectively) of the molecules, cells, small molecules or particles. Alternatively, a branch channel may be in communication with other channels to permit additional sorting.

The device of the present invention can further include one or more outlet modules. An "outlet module" is an area of the device that collects or dispenses molecules, cells, small molecules or particles after coalescence, detection and/or sorting. The outlet module can include a collection module and/or a waste module. The collection module can be connected to a means for storing a sample. The collection module can be a well or reservoir for collecting and containing droplets detected to have a specific predetermined characteristic in the detection module. The collection module can be temperature controlled. The waste module can be connected to a means for discarding a sample. The waste module can be a well or reservoir for collecting and containing droplets detected to not have a specific predetermined characteristic in the detection module. The outlet module is downstream from a sorting module, if present, or downstream from the detection module if a sorting module is not present. The outlet module may contain branch channels or outlet channels for connection to a collection module or waste module. A device can contain more than one outlet module.

A characteristic of a fluidic droplet may be sensed and/or determined in some fashion, for example, as described herein (e.g., fluorescence of the fluidic droplet may be determined), and, in response, an electric field may be applied or removed from the fluidic droplet to direct the fluidic droplet to a particular region (e.g. a channel). A fluidic droplet is preferably sorted or steered by inducing a dipole in the uncharged fluidic droplet (which may be initially charged or uncharged), and sorting or steering the droplet using an applied electric field. The electric field may be an AC field, a DC field, etc. Methods of sorting or steering droplets in an electric field are as described in WO 2006/040551; U.S. Patent Application Publication No. 2009/0005254; WO 2006/040554; U.S. Patent Application Publication No. 2007/0184489; WO 2004/002627; U.S. Pat. No. 7,708,949; WO 2004/091763; U.S. Patent Application Publication No. 2006/0163385; WO 2005/021151; U.S. Patent Application Publication No. 2007/0003442; WO 2006/096571; U.S. Patent Application Publication No. 2009/0131543; WO 2007/089541; U.S. Patent Application Publication No. 2007/0195127; WO 2007/081385; U.S. Patent Application Publication No. 2010/0137163; WO 2007/133710 and U.S. Patent Application Publication No. 2008/0014589. Improvements in the efficiency, accuracy, and reliability of the preferred dielectric droplet sorting technique described above are possibly by utilizing additional channel and electrode geometries, as described in WO 2007/081385; U.S. Patent Application Publication No. 2010/0137163; WO 2008/063227 and U.S. Patent Application Publication No. 2008/0003142.

Alternately, a fluidic droplet may be directed by creating an electric charge (e.g., as previously described) on the droplet, and steering the droplet using an applied electric field, which may be an AC field, a DC field, etc. As an example, an electric field maybe selectively applied and removed (or a different electric field may be applied) as needed to direct the fluidic droplet to a particular region. The electric field may be selectively applied and removed as needed, in some embodiments, without substantially altering the flow of the liquid containing the fluidic droplet. For example, a liquid may flow on a substantially steady-state basis (i.e., the average flowrate of the liquid containing the fluidic droplet deviates by less than 20% or less than 15% of the steady-state flow or the expected value of the flow of liquid with respect to time, and in some cases, the average flowrate may deviate less than 10% or less than 5%) or other predetermined basis through a fluidic system of the invention (e.g., through a channel or a microchannel), and fluidic droplets contained within the liquid may be directed to various regions, e.g., using an electric field, without substantially altering the flow of the liquid through the fluidic system.

In some embodiments, the fluidic droplets may be sorted into more than two channels. Alternately, a fluidic droplet may be sorted and/or split into two or more separate droplets, for example, depending on the particular application. Any of the above-described techniques may be used to spilt and/or sort droplets. As a non-limiting example, by applying (or removing) a first electric field to a device (or a portion thereof), a fluidic droplet may be directed to a first region or channel; by applying (or removing) a second electric field to the device (or a portion thereof), the droplet may be directed to a second region or channel; by applying a third electric field to the device (or a portion thereof), the droplet may be directed to a third region or channel; etc., where the electric fields may differ in some way, for example, in intensity, direction, frequency, duration, etc. In a series of droplets, each droplet may be independently sorted and/or split; for example, some droplets may be directed to one location or another, while other droplets may be split into multiple droplets directed to two or more locations.

In some cases, high sorting speeds may be achievable using certain systems and methods of the invention. For instance, at least about 1 droplet per second may be determined and/or sorted in some cases, and in other cases, at least about 10 droplets per second, at least about 20 droplets per second, at least about 30 droplets per second, at least about 100 droplets per second, at least about 200 droplets per second, at least about 300 droplets per second, at least about 500 droplets per second, at least about 750 droplets per second, at least about 1000 droplets per second, at least about 1500 droplets per second, at least about 2000 droplets per second, at least about 3000 droplets per second, at least about 5000 droplets per second, at least about 7500 droplets per second, at least about 10,000 droplets per second, at least about 15,000 droplets per second, at least about 20,000 droplets per second, at least about 30,000 droplets per second, at least about 50,000 droplets per second, at least about 75,000 droplets per second, at least about 100,000 droplets per second, at least about 150,000 droplets per second, at least about 200,000 droplets per second, at least about 300,000 droplets per second, at least about 500,000 droplets per second, at least about 750,000 droplets per second, at least about 1,000,000 droplets per second may be determined and/or sorted in such a fashion.

The present invention proposes methods for recovering aqueous phase components from aqueous emulsions that have been collected on a microfluidic device in a minimum number of steps and in a gentle manner so as to minimize potential damage to cell viability.

In one aspect, a stable aqueous sample droplet emulsion containing aqueous phase components in a continuous phase carrier fluid is allowed to cream to the top of the continuous phase carrier oil. By way of nonlimiting example, the continuous phase carrier fluid can include a perfluorocarbon oil that can have one or more stabilizing surfactants. The aqueous emulsion rises to the top or separates from the continuous phase carrier fluid by virtue of the density of the continuous phase fluid being greater than that of the aqueous phase emulsion. For example, the perfluorocarbon oil used in one embodiment of the device is 1.8, compared to the density of the aqueous emulsion, which is 1.0.

The creamed emulsion is then placed onto a second continuous phase carrier fluid which contains a de-stabilizing surfactant, such as a perfluorinated alcohol (e.g., 1H,1H, 2H,2H-Perfluoro-1-octanol). The second continuous phase carrier fluid can also be a perfluorocarbon oil. Upon mixing, the aqueous emulsion begins to coalesce, and coalescence is completed by brief centrifugation at low speed (e.g., 1 minute at 2000 rpm in a microcentrifuge). The coalesced aqueous phase can now be removed (cells can be placed in an appropriate environment for further analysis).

Additional destabilizing surfactants and/or oil combinations can be identified or synthesized to be useful with this invention.

The microfluidic devices of the present invention can further include one or more mixing modules, one or more delay modules, one or more acoustic actuators and/or UV-release modules, as described in WO 2007/081385; U.S. Patent Application Publication No. 2010/0137163; WO 2008/063227 and U.S. Patent Application Publication No. 2008/0003142.

The terms used in this specification generally have their ordinary meanings in the art, within the context of this invention and in the specific context where each term is used. Certain terms are discussed below, or elsewhere in the specification, to provide additional guidance to the practitioner in describing the devices and methods of the invention and how to make and use them. It will be appreciated that the same thing can typically be described in more than one way. Consequently, alternative language and synonyms may be used for any one or more of the terms discussed herein. Synonyms for certain terms are provided. However, a recital of one or more synonyms does not exclude the use of other synonyms, nor is any special significance to be placed upon whether or not a term is elaborated or discussed herein. All publications, patent applications, patents, and other references mentioned herein are incorporated by reference. In the case of conflict, the present specification, including definitions, will control. In addition, the materials, methods, and examples are illustrative only and are not intended to be limiting.

The invention is also described by means of particular examples. However, the use of such examples anywhere in the specification, including examples of any terms discussed herein, is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

As used herein, "about" or "approximately" shall generally mean within 20 percent, preferably within 10 percent, and more preferably within 5 percent of a given value or range.

The term "molecule" means any distinct or distinguishable structural unit of matter comprising one or more atoms, and includes for example polypeptides and polynucleotides.

The term "polymer" means any substance or compound that is composed of two or more building blocks ('mers') that are repetitively linked to each other. For example, a "dimer" is a compound in which two building blocks have been joined together.

The term "polynucleotide" as used herein refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded RNA and DNA, and backbone modifications thereof, for example, methylphosphonate linkages.

Thus, a "polynucleotide" or "nucleotide sequence" is a series of nucleotide bases (also called "nucleotides") generally in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The polynucleotides herein may be flanked by natural regulatory sequences, or may be associated with heterologous sequences, including promoters, enhancers, response elements, signal sequences, polyadenylation sequences, introns, 5'- and 3'- non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The term "dielectrophoretic force gradient" means a dielectrophoretic force is exerted on an object in an electric field provided that the object has a different dielectric constant than the surrounding media. This force can either pull the object into the region of larger field or push it out of the region of larger field. The force is attractive or repulsive depending respectively on whether the object or the surrounding media has the larger dielectric constant.

"DNA" (deoxyribonucleic acid) means any chain or sequence of the chemical building blocks adenine (A), guanine (G), cytosine (C) and thymine (T), called nucleotide bases, that are linked together on a deoxyribose sugar backbone. DNA can have one strand of nucleotide bases, or two complimentary strands which may form a double helix structure. "RNA" (ribonucleic acid) means any chain or sequence of the chemical building blocks adenine (A), guanine (G), cytosine (C) and uracil (U), called nucleotide bases, that are linked together on a ribose sugar backbone. RNA typically has one strand of nucleotide bases.

A "polypeptide" (one or more peptides) is a chain of chemical building blocks called amino acids that are linked together by chemical bonds called peptide bonds. A "protein" is a polypeptide produced by a living organism. A protein or polypeptide may be "native" or "wild-type", meaning that it occurs in nature; or it may be a "mutant", "variant" or "modified", meaning that it has been made, altered, derived, or is in some way different or changed from a native protein, or from another mutant.

An "enzyme" is a polypeptide molecule, usually a protein produced by a living organism, that catalyzes chemical reactions of other substances. The enzyme is not itself altered or destroyed upon completion of the reaction, and can therefore be used repeatedly to catalyze reactions. A "substrate" refers to any substance upon which an enzyme acts.

As used herein, "particles" means any substance that may be encapsulated within a droplet for analysis, reaction, sorting, or any operation according to the invention. Particles are not only objects such as microscopic beads (e.g., chromatographic and fluorescent beads), latex, glass, silica or paramagnetic beads, but also includes other encapsulating porous and/or biomaterials such as liposomes, vesicles and other emulsions. Beads ranging in size from 0.1 micron to 1 mm can be used in the devices and methods of the invention and are therefore encompassed with the term "particle" as used herein. The term particle also encompasses biological cells, as well as beads and other microscopic objects of similar size (e.g., from about 0.1 to 120 microns, and typically from about 1 to 50 microns) or smaller (e.g., from about 0.1 to 150 nm). The devices and methods of the invention are also directed to sorting and/or analyzing molecules of any kind, including polynucleotides, polypeptides and proteins (including enzymes) and their substrates and small molecules (organic or inorganic). Thus, the term particle further encompasses these materials.

The particles (including, e.g., cells and molecules) are sorted and/or analyzed by encapsulating the particles into individual droplets (e.g., droplets of aqueous solution in oil), and these droplets are then sorted, combined and/or analyzed in a microfabricated device. Accordingly, the term "droplet" generally includes anything that is or can be contained within a droplet.

A "small molecule" or "small molecule chemical compound" as used herein, is meant to refer to a composition that has a molecular weight of less than 500 Daltons. Small molecules are distinguished from polynucleotides, polypeptides, carbohydrates and lipids.

As used herein, "cell" means any cell or cells, as well as viruses or any other particles having a microscopic size, e.g. a size that is similar to or smaller than that of a biological cell, and includes any prokaryotic or eukaryotic cell, e.g., bacteria, fungi, plant and animal cells. Cells are typically spherical, but can also be elongated, flattened, deformable and asymmetrical, i.e., non-spherical. The size or diameter of a cell typically ranges from about 0.1 to 120 microns, and typically is from about 1 to 50 microns. A cell may be living or dead. Since the microfabricated device of the invention is directed to sorting materials having a size similar to a biological cell (e.g. about 0.1 to 120 microns) or smaller (e.g., about 0.1 to 150 nm) any material having a size similar to or smaller than a biological cell can be characterized and sorted using the microfabricated device of the invention. Thus, the term cell shall further include microscopic beads (such as chromatographic and fluorescent beads), liposomes, emulsions, or any other encapsulating biomaterials and porous materials. Non-limiting examples include latex, glass, orparamagnetic beads; and vesicles such as emulsions and liposomes, and other porous materials such as silica beads. Beads ranging in size from 0.1 micron to 1 mm can also be used, for example in sorting a library of compounds produced by combinatorial chemistry. As used herein, a cell may be charged or uncharged. For example, charged beads may be used to facilitate flow or detection, or as a reporter. Biological cells, living or dead, may be charged for example by using a surfactant, such as SDS (sodium dodecyl sulfate). The term cell further encompasses "virions", whether or not virions are expressly mentioned.

A "virion", "virus particle" is the complete particle of a virus. Viruses typically comprise a nucleic acid core (comprising DNA or RNA) and, in certain viruses, a protein coat or "capsid". Certain viruses may have an outer protein covering called an "envelope". A virion may be either living (i.e., "viable") or dead (i.e., "non-viable"). A living or "viable" virus is one capable of infecting a living cell. Viruses are generally smaller than biological cells and typically range in size from about 20-25 nm diameter or less (parvoviridae, picornoviridae) to approximately 200-450 nm (poxviridae). However, some filamentous viruses may reach lengths of 2000 nm (closterviruses) and are therefore larger than some bacterial cells. Since the microfabricated device of the invention is particularly suited for sorting materials having a size similar to a virus (i.e., about 0.1 to 150 nm), any material having a size similar to a virion can be characterized and sorted using the microfabricated device of the invention. Non-limiting examples include latex, glass or paramagnetic beads; vesicles such as emulsions and liposomes, and other porous materials such as silica beads. Beads ranging in size from 0.1 to 150 nm can also be used, for example, in sorting a library of compounds produced by combinatorial chemistry. As used herein, a virion may be charged or uncharged. For example, charged beads may be used to facilitate flow or detection, or as a reporter. Biological viruses, whether viable or non-viable, may be charged, for example, by using a surfactant, such as SDS.

A "reporter" is any molecule, or a portion thereof, that is detectable, or measurable, for example, by optical detection. In addition, the reporter associates with a molecule, cell or virion or with a particular marker or characteristic of the molecule, cell or virion, or is itself detectable to permit identification of the molecule, cell or virion's, or the presence or absence of a characteristic of the molecule, cell or virion. In the case of molecules such as polynucleotides such characteristics include size, molecular weight, the presence or absence of particular constituents or moieties (such as particular nucleotide sequences or restrictions sites). In the case of cells, characteristics which may be marked by a reporter includes antibodies, proteins and sugar moieties, receptors, polynucleotides, and fragments thereof. The term "label" can be used interchangeably with "reporter". The reporter is typically a dye, fluorescent, ultraviolet, or chemiluminescent agent, chromophore, or radio-label, any of which may be detected with or without some kind of stimulatory event, e.g., fluoresce with or without a reagent. In one embodiment, the reporter is a protein that is optically detectable without a device, e.g. a laser, to stimulate the reporter, such as horseradish peroxidase (HRP). A protein reporter can be expressed in the cell that is to be detected, and such expression may be indicative of the presence of the protein or it can indicate the presence of another protein that may or may not be coexpressed with the reporter. A reporter may also include any substance on or in a cell that causes a detectable reaction, for example by acting as a starting material, reactant or a catalyst for a reaction which produces a detectable product. Cells may be sorted, for example, based on the presence of the substance, or on the ability of the cell to produce the detectable product when the reporter substance is provided.

A "marker" is a characteristic of a molecule, cell or virion that is detectable or is made detectable by a reporter, or which may be coexpressed with a reporter. For molecules. a marker can be particular constituents or moieties, such as restrictions sites or particular nucleic acid sequences in the case of polynucleotides. For cells and virions, characteristics may include a protein, including enzyme, receptor and ligand proteins, saccharides, polynucleotides, and combinations thereof, or any biological material associated with a cell or virion. The product of an enzymatic reaction may also be used as a marker. The marker may be directly or indirectly associated with the reporter or can itself be a reporter. Thus, a marker is generally a distinguishing feature of a molecule, cell or virion, and a reporter is generally an agent which directly or indirectly identifies or permits measurement of a marker. These terms may, however, be used interchangeably.

The invention is further described below, by way of the following examples. The examples also illustrate useful methodology for practicing the invention. These examples do not limit the claimed invention.

EXAMPLES

Material and Methods

Microfluidic devices were prepared by standard soft lithography techniques (Xia, Y. N., and Whitesides, G. M., *Ann. Rev. Mat. Sci.* 28: 153-184, 1998) in poly(dimethylsiloxane) (PDMS) with channel depths of 20 μm. The PDMS was treated in an oxygen plasma oven (Gala Instrumente)

and bound to a glass slide. The surface was treated with Trichloro(1H,1H,2H,2H-perfluorooctyl)silane from Aldrich, 20 µl dissolved in 1 ml HFE-7100 (3M). The channels where then flushed with a commercial fluorinated oil (FC40, 3M, density F=1.9 $10^3$ kg/m$^3$) and subsequently dried with $N_2$ prior to use was used to decrease the wettability of aqueous phase on the channel walls. All devices consisted of one (for all test devices) or two (for the exchange experiment) classical flow focusing nozzles of 10 µm cross-section, enabling the production of water droplets in a continuous oil phase (Anna et al., *Applied Physics Letters* 82: 364-366, 2003) followed by a thin channel of width w=40 µm and variable length L in which the droplets are separated to prevent collision for a time τ~L, and finally an exchange part in which droplets can collide and the continuous oil phase is exchanged. The aqueous phase was pure water (Milli-Q grade, 18MΩ), the oil phase was FC40, which (i) does not cause PDMS swelling and (ii) does not solubilize most nonfluorinated organic molecules and thereby hinders the exchange of molecules between droplets through phase partitioning.

Two different amphiphilic molecule with a fluorinated tail of a commercial oil (krytox FSH) and a hydrophilic head (either dimorpholinophosphate (DMP) or ammonium carboxylate R24 (Clausell-Tormos et al., *Chem Biol* 15: 427-437, 2008; Loeker et al., *Colloids and Surfaces A: Physicochem. Eng. Aspects* 214: 143-150, 2003) were used as a surfactant, solublized in the oil at a concentration C(w/w) =5%. Volumetric flow rates were controlled using syringe pumps (PHD22/2000, Harvard Apparatus). This device is interfaced with an optical setup to measure droplet fluorescence in an epifluorescence geometry. For the exchange experiments, the aqueous phase was doped with resorufin at micromolar concentration in PBS buffer solution.

Example 1

The continuous stream of droplets in surfactant loaded oil is subsequently subjected to several actively controlled extractions of the continuous fluorinated oil phase and injections of pure oil (See, FIG. 1). This apparatus and method first reduces the volume fraction of surfactant loaded oil, thus densifying the droplets in the main channel after the extraction. Subsequent injection of pure oil dilutes the surfactant in the continuous phase. This injection of pure oil also serves to respace the droplets. This can be repeated several times, which reduces the micellar concentration considerably. Additional oil extractions can be added to control the droplet density in the delay line. (See, the right margin of FIG. 1).

Figure 2:
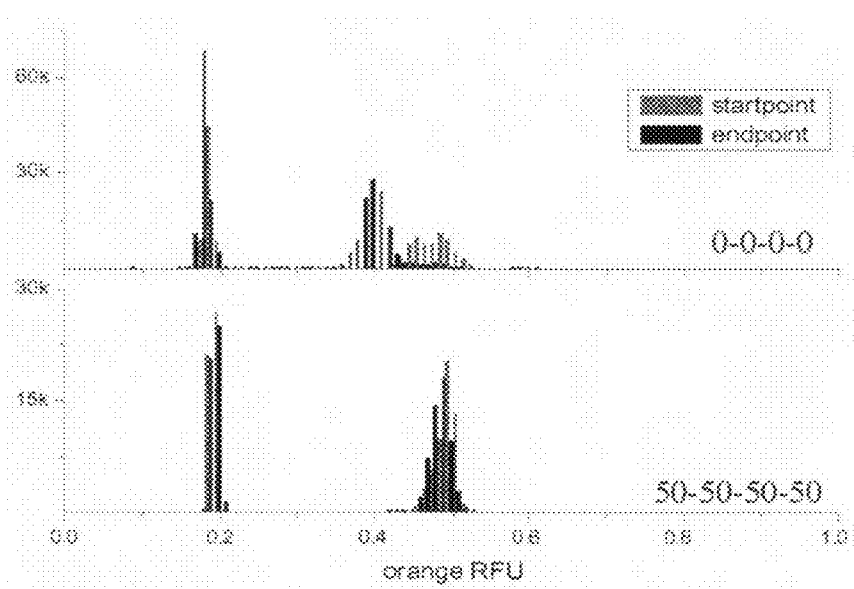
FIG. 2 contains a graph showing the exchange of small fluorescent molecules between droplets within a microfluidic device.

The effect of such an actively controlled oil exchange on the exchange of small fluorescent molecules between droplets was monitored in a delay line on chip (See, FIG. 2). The fluorophore under investigation was resorufin. Two droplet populations with different concentrations of 10 and 4 µM were created and merged (See, leftmost margin of FIG. 1). The exchange was monitored by measuring the fluorescent intensity at two points on chip: a start point right after the merging of the two populations and an endpoint after a delay line of approx. 10 minutes. The result is shown in FIG. 2. Exchange flow rates [µl/h] are given on the right side, the coding is: 1st oil extractor—pure oil injection—2nd oil extractor—pure oil injection.

A statistical analysis over 100,000 droplets was performed and the data were scaled to the start point lower intensity (4 µM). A shifting of the higher fluorescent intensity peak towards lower values at the endpoint (black bars) thus shows an exchange of fluorophore between droplets in the delay line. This is the case for resorufin when the continuous oil phase is not exchanged and therefore filled with micelles (See, top portion of FIG. 2). However, when the continuous oil phase is exchanged by activating the pumps at the extractors and injectors (See, FIG. 1), the exchange between droplets can be dramatically reduced and effectively eliminated (See, bottom portion of FIG. 2). For flow rates of 50 µl/h for the four pumps of the $1^{st}$ and $2^{nd}$ oil extractor and the two pure oil injectors the higher fluorescent intensity peak and the endpoint does not change with respect to its value at the start point which means that both droplet populations did not exchange any resorufin.

Example 2

Figure 3:
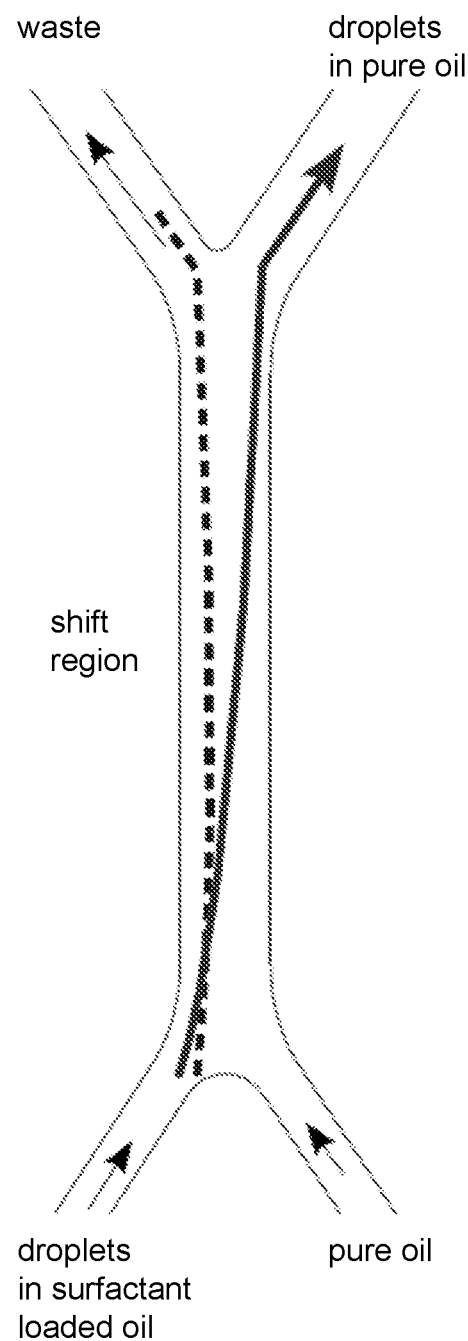
FIG. 3 contains a schematic illustrating a passive droplet shifting exchange chamber.

In this example, droplets are produced and then transferred from the surfactant loaded oil stream into a surfactant free oil stream making use of the laminar flow conditions in a microfluidic device. The focus is to switch the droplets in an exchange chamber from one laminar oil stream to an adjacent laminar stream. In this way, the aqueous droplets leave the surfactant loaded oil stream after a period of time sufficiently long to stabilize the interface and enter a surfactant free oil stream. The droplets are now in a completely micelle free environment and even if surfactant detaches from the interface and enters the continuous phase, this process is slow and will end when the CMC is reached. A schematic design of the exchange chamber is illustrated in FIG. 3. The droplets enter the chamber from the lower left and their stream (surfactant loaded oil and aqueous droplets) is paralleled by a stream of pure oil, entering from the lower right. Due to the laminar flow regime the surfactant is not mixed with the pure oil as its diffusion perpendicular to the flow lines is limited. The laminar flow (dotted line) is generated and the flow rates of the two stream are adjusted such that a considerable amount of pure oil enters the "waste" channel (upper left) to avoid a transfer of the surfactant loaded oil stream into the droplet/surfactant free stream extraction channel (upper right). The desired pathway of the droplets is shown as by the solid arrow.

The actual switching of the droplets from one stream to another can be achieved by various means, including, but not limited to, obstacles (e.g. pillars), 3D structures (e.g. vertical traps), and electrical fields (e.g. by dielectrophoresis).

Figure 4:
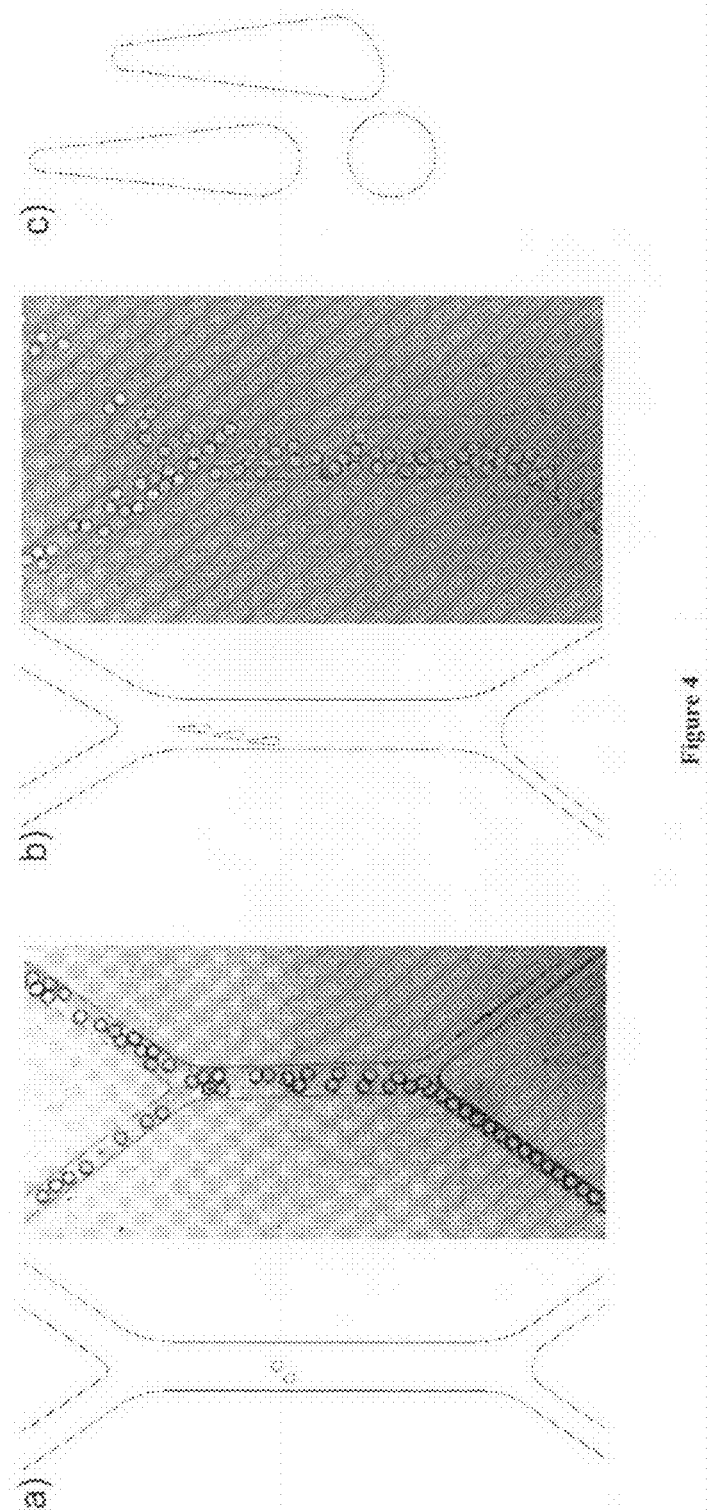
FIG. 4 contains several schematics and accompanying photographs illustrating several different obstacle/pillar designs for passive droplet shifting.

The concept of pillars is shown in FIG. 4. Two simple pillars within the microfluidic channel serve as obstacles in the surfactant loaded oil stream and randomize the droplet flow such that about 50% of droplets enter the extraction channel (See, FIG. 4, Panel A). Limitations of the simple pillar concept are that large droplets tend to split. This splitting can be reduced by either reducing the velocities of the droplets (which is limited by the geometry of the flow focusing apparatus) or the use of more sophisticated pillar shapes with a design analogous to those used in aerodynamics where the pressure profiles are less pronounced at the edges (See, FIG. 4, Panels B and C). The photograph in Panel A shows surfactant oil flowing at 20 µl/h, aqueous droplets flowing at 20 µl/h and pure oil flowing at 100 µl/h. The photograph in Panel B shows surfactant oil flowing at 50 µl/h, aqueous droplets flowing at 50 µl/h and pure oil flowing at 300 µl/h.

Figure 5:
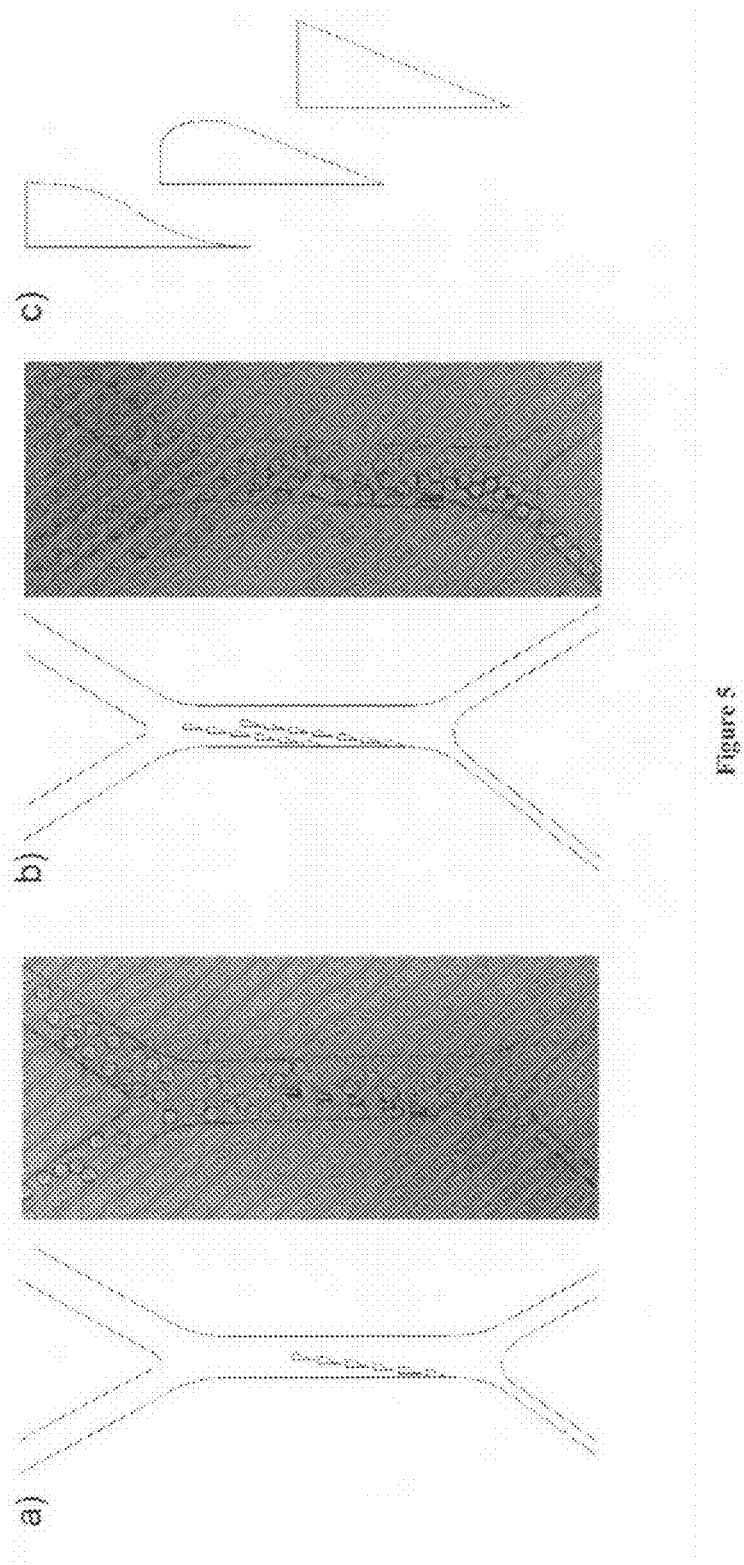
FIG. 5 contains several schematics and accompanying photographs illustrating several different obstacle/pillar ladder designs for passive droplet shifting.

In another embodiment to address the problem of wasted/lost droplets and droplet breakup at higher flow rates, obstacles arranged in a ladder-like fashion with smoother shapes was tested (See, FIG. 5). FIG. 5, Panel A shows a single ladder design. The photograph in Panel A shows surfactant oil flowing at 50 µl/h, aqueous droplets flowing at 20 µl/h and pure oil flowing at 100 µl/h. FIG. 5, Panel B shows a double ladder design to increase efficiency and minimize loss. The photograph in Panel B shows surfactant oil flowing at 50 µl/h, aqueous droplets flowing at 50 µl/h and pure oil flowing at 300 µl//h. FIG. 5, Panel C shows additional ladder element designs. The number of wasted droplets and droplet breakup can indeed be reduced with this design, especially in the case of double ladder arrangements.

Figure 6:
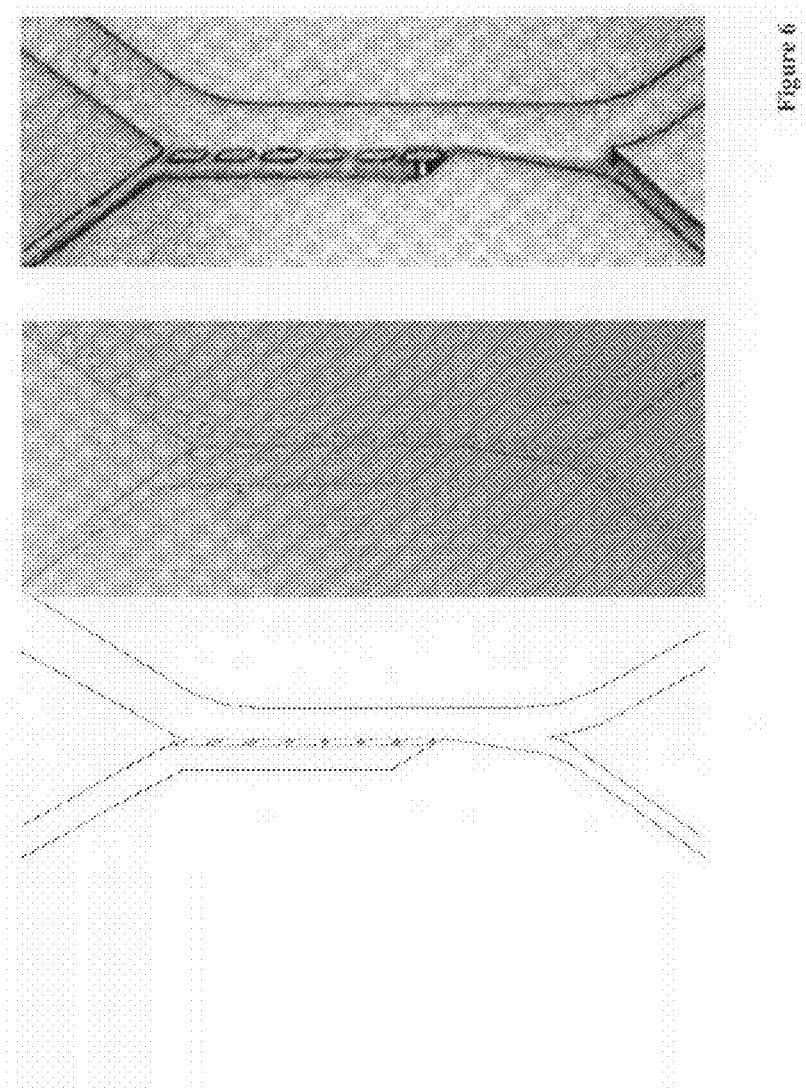
FIG. 6 contains a schematic and accompanying photographs illustrating a surfactant filter design for passive droplet shifting.

In another embodiment to address the problem of wasted/lost droplets and droplet breakup at higher flow rates, a surfactant filter was designed (See, schematic in FIG. 6, Left Panel). In FIG. 6, the surfactant loaded oil stream is gently evacuated and where the droplets are not subjected to a pathway that induces multiple shear forces on the droplets as is the case for obstacles. Specifically, droplets shift with no loss (middle Panel) and the surfactant is completely filtered (dark flow lines in the right Panel, the flow lines made visible by ink in the water. The photograph in Panel B shows surfactant oil flowing at 70 µl/h, aqueous droplets flowing at 50 µl/h and pure oil flowing at 800 µl/h. The photograph in Panel C shows ink in the water flowing at 70 µl/h and pure oil flowing at 400 µl/h. This design completely eliminates the loss of droplets into the waste channel even at high flow rates and when using large droplets while the surfactant loaded oil stream is completely evacuated.

Figure 7:
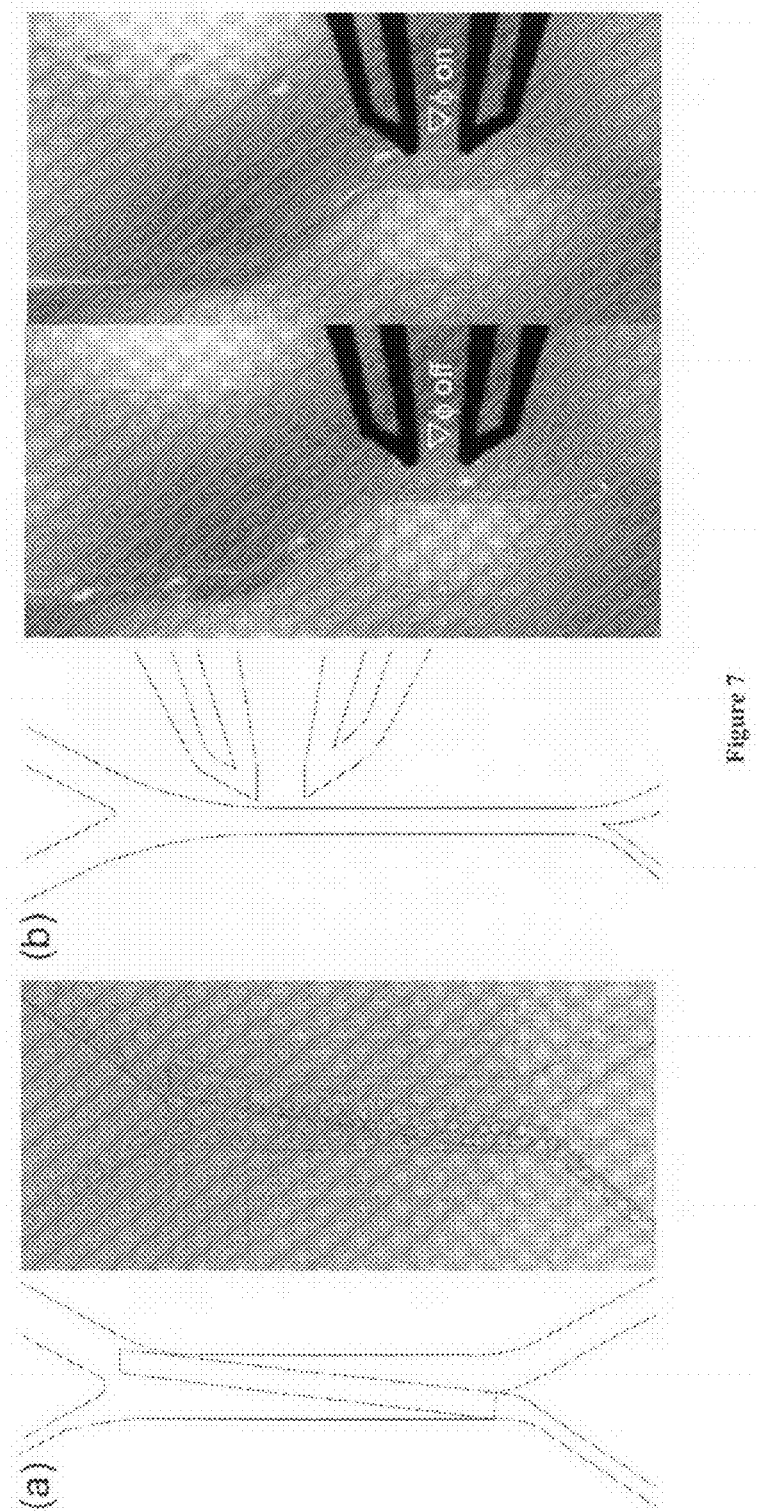
FIG. 7 contains several schematics and accompanying photographs illustrating a three-dimensional shifting design (Panel A) and a dielectrophoresis shifting design for passive droplet shifting.

A 3D shifter where the droplets follow a deeper part of the channel due to high buoyancy forces was also tested (See, FIG. 7, Panel A). Results show that in this design droplets do not split and utilizing lower flow rates of the pure oil stream will minimize the loss of droplets into the waste channel. The photograph in Panel A shows surfactant oil flowing at 70 µl/h, aqueous droplets flowing at 50 µl/h and pure oil flowing at 200 µl/h.

Finally, an electrical field gradient (Ahn et al., *Applied Physics Letters* 88: Art. No. 024104, 2006; Baret et al., *Lab on a Chip* 9: 1850-1858, 2009) was used to move droplets across the streamlines by dielectrophoresis (See, FIG. 7, Panel B). The results showed that application of an AC electric field of 1-1.4 $kV_{p-p}$ across the electrodes leads to a deflection of the droplets into the surfactant free arm. The photograph in Panel B shows surfactant oil flowing at 1000 µl/h, aqueous droplets flowing at 200 µl/h and pure oil flowing at 4000 µl/h.

Example 3

Figure 8:
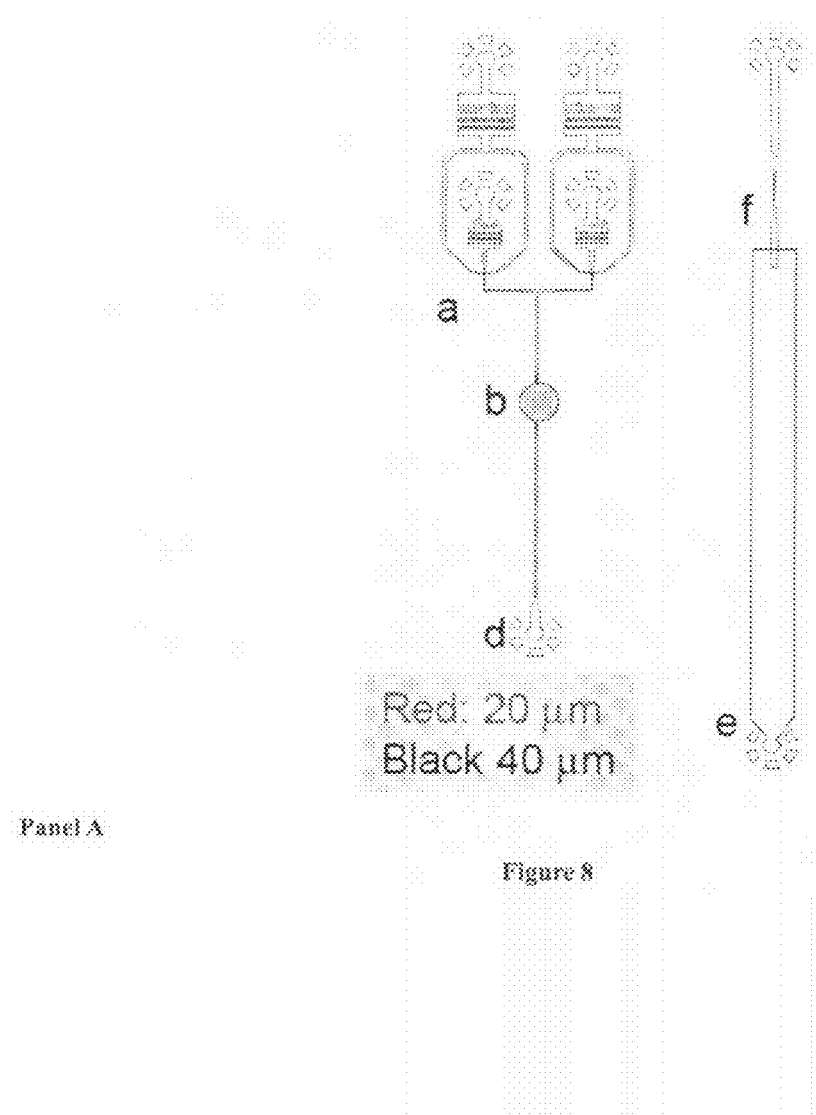
FIG. 8 contains several schematics illustrating an external reservoir design for passive droplet shifting.
Figure 8:
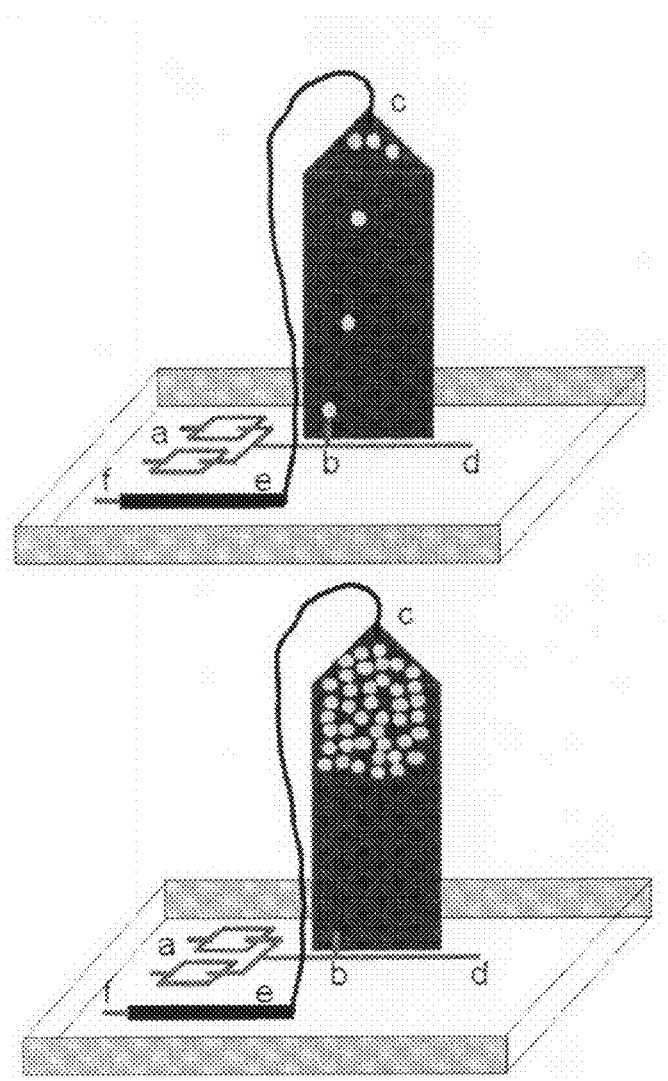

In this example, droplets are created and directed into a reservoir (e.g., vial or other container) that is mounted on top of the microfluidic device (See, FIG. 8). This reservoir is filled with pure oil and thus the aqueous droplets will cream/rise towards the top of the reservoir due to the high buoyancy force of water in fluorinated oil (the density difference is about 1.7). Additionally, pure oil is injected from the top of the reservoir which creates a stream of pure oil in the inverse direction of the creaming droplets. The outlet of the reservoir, necessary to avoid an over pressure, is also at the bottom. The principle of this device is to transfer the droplets to a surfactant free environment and to continuously wash them in this environment. The emulsion can be stored in this reservoir for long periods of time (longer than in on-chip delay lines) and be reinjected. The reinjection is achieved by inverting the flow directions: pure oil is pushed from both bottom inlets of the reservoir and the emulsion leaves the reservoir via the top tubing. Specifically as shown in FIG. 8, Panel B, droplets are created at point A and leave the microfluidic channel through a hole to enter the reservoir at point B. The reservoir is filled with surfactant free, or surfactant reduced, oil and a constant flow of oil maintained during the droplet production from top to bottom by injection oil at point F through the tubing that connects points E and C. As shown in FIG. 8, Panel C, droplets rise to the top of the reservoir and a pressure exit is maintained at point D. For reinjection of the droplets, all inlets in point A are blocked and pure oil, is injected at point D. The droplets are then injected into the tubing at point C and re-introduced to the microfluidic device at an opening at point E. Additional analysis of the droplets can occur at point F.

What is claimed is:

1. A method of stabilizing a plurality of microdroplets for introduction into a delay line, comprising the steps of:
    (a) flowing in a main microfluidic channel a first emulsion comprising a plurality of microdroplets in an immiscible carrier fluid, wherein the plurality of microdroplets comprise a first microdroplet and a second microdroplet, and wherein the first microdroplet comprises a first biological or chemical material and the second microdroplet comprises a second biological or chemical material, and the carrier fluid comprises a surfactant at a first concentration within the carrier fluid;
    (b) exchanging a portion of the immiscible carrier fluid by removing a portion of the carrier fluid from the main microfluidic channel via a first side microfluidic channel, and adding a second fluid into the main microfluidic channel via a second side microfluidic channel immediately downstream from the first side microfluidic channel to generate a second emulsion, wherein the second fluid is immiscible with the plurality of microdroplets and comprises a second concentration of the surfactant, thereby changing the first concentration to a second concentration, wherein the second concentration is lower than the first concentration; and
    (c) introducing the second emulsion into a delay line.

2. The method of claim 1, wherein the first biological or chemical material and/or the second biological or chemical material comprises a tissue, cell, particle, protein, antibody, amino acid, nucleotide, small molecule, pharmaceutical, and/or label.

3. The method of claim 1, wherein the first concentration is sufficient to stabilize the microdroplets against coalescing with each other in the first carrier fluid.

4. The method of claim 3, wherein the first concentration is determined, at least in part, based on stabilizing the microdroplets over a time frame determined by a reaction and/or detection of the one or more biological and/or chemical materials.

5. The method of claim 1, wherein the second concentration is sufficient to reduce exchange of the first biological or chemical material from the first microdroplet to the second microdroplet, or of the second biological or chemical material from the second microdroplet to the first microdroplet.

6. The method of claim 5, wherein the second concentration is determined, at least in part, based on stabilizing the microdroplets over a time frame determined by generation and/or use of the first microdroplet and the second microdroplet in one or more libraries.

7. The method of claim 5, wherein the second fluid is substantially free of the first surfactant.

8. A method of adjusting a carrier fluid before introduction to a delay line in a microfluidic network, comprising the steps of:

(a) flowing a first emulsion comprising a plurality of microdroplets in an immiscible first carrier fluid in a main microfluidic channel, wherein the first carrier fluid comprises a first concentration of a surfactant;

(b) introducing a second carrier fluid to the main microfluidic channel via a first side microfluidic channel and removing a portion of the carrier fluid from the main microfluidic channel via a second side microfluidic channel immediately downstream from the first side microfluidic channel, thereby exchanging the portion of the first carrier fluid for the second carrier fluid to generate a second emulsion, wherein the second carrier fluid contains no surfactant or a second concentration of the surfactant that is lower than the first concentration; and (c) introducing the second emulsion into a delay line.

9. The method of claim 8, wherein step (b) is accomplished in a region of the main microfluidic channel comprising at least one obstacle.

10. The method of claim 8, wherein step (b) is accomplished, at least in part, by shifting the microdroplets from the first carrier fluid into a stream of the second carrier fluid.

11. The method of claim 10, wherein the shifting is accomplished by using one or more obstacles, changing channel depth, by dielectrophoresis, or by buoyancy.

12. The method of claim 1, wherein the carrier fluid is a fluorinated oil.

13. The method of claim 1, wherein the second fluid is the same as the carrier fluid.

14. The method of claim 8, wherein step (b) is accomplished in a region of the main microfluidic channel comprising a filter.

15. The method of claim 1, wherein the first microdroplet contains no more than one biological or chemical molecule and the second microdroplet contains no more than one biological or chemical molecule.

16. The method of claim 1, wherein the first microdroplet contains no more than one biological or chemical molecule and the second microdroplet contains a plurality of biological or chemical molecules.

17. The method of claim 1, wherein the first microdroplet contains a plurality of biological or chemical molecules and the second microdroplet contains a plurality of biological or chemical molecules.

18. The method of claim 1, further comprising directing the microdroplets into a reservoir outside of the main microfluidic channel.

19. The method of claim 18, wherein the reservoir contains a third carrier fluid, wherein the third carrier fluid contains no surfactant or a concentration of the surfactant that is lower than the first concentration.

20. The method of claim 19, wherein the reservoir is attached to the top of the main microfluidic channel.

21. The method of claim 20, further comprising adding the third carrier fluid from the bottom of the reservoir, thereby causing the microdroplets to rise out of the top of the reservoir.

22. The method of claim 1, wherein the second concentration of the surfactant is zero.

* * * * *